United States Patent
Chow et al.

(10) Patent No.: US 9,522,282 B2
(45) Date of Patent: Dec. 20, 2016

(54) POWERING MULTIPLE IMPLANTABLE MEDICAL THERAPY DELIVERY DEVICES USING FAR FIELD RADIATIVE POWERING AT MULTIPLE FREQUENCIES

(71) Applicant: CYBERONICS, INC., Houston, TX (US)

(72) Inventors: Eric Y. Chow, Houston, TX (US); Jonathan D. Rowell, Houston, TX (US)

(73) Assignee: CYBERONICS, INC., Houston, TX (US)

( * ) Notice: Subject to any disclaimer, the term of this patent is extended or adjusted under 35 U.S.C. 154(b) by 279 days.

(21) Appl. No.: 13/869,848

(22) Filed: Apr. 24, 2013

(65) Prior Publication Data

US 2013/0261703 A1    Oct. 3, 2013

Related U.S. Application Data

(63) Continuation-in-part of application No. 13/434,240, filed on Mar. 29, 2012, now Pat. No. 9,402,994, and
(Continued)

(51) Int. Cl.
*A61N 1/372* (2006.01)
*A61N 1/378* (2006.01)
(Continued)

(52) U.S. Cl.
CPC ............ *A61N 1/3787* (2013.01); *A61N 1/3605* (2013.01); *A61N 1/37223* (2013.01); *A61N 1/40* (2013.01); *A61B 2560/0219* (2013.01)

(58) Field of Classification Search
CPC .... A61N 1/40; A61N 1/3787; A61N 1/37217; A61N 1/37223; A61B 2560/0219
See application file for complete search history.

(56) References Cited

U.S. PATENT DOCUMENTS

| 3,867,950 A | 2/1975 | Fischell |
| 5,591,217 A | 1/1997 | Barreras |

(Continued)

FOREIGN PATENT DOCUMENTS

| CA | 2802936 | 1/2012 |
| WO | WO-2010/104569 | 9/2010 |

OTHER PUBLICATIONS

"Part 15—Radio Frequency Devices (47 CFR 15), Title 47 of the Code of Federal Regulations," *Federal Communications Commission*, current as of Dec. 22, 2011; found at: http://www.ecfr.gov/cgi-bin/text-idx?node=47:1.0.1.1.16.
(Continued)

*Primary Examiner* — Tammie K Heller
(74) *Attorney, Agent, or Firm* — Foley & Lardner LLP

(57) ABSTRACT

A system includes a first implantable medical device configured to receive a first far field radiative signal at a first frequency from an external transmitter to charge a first charge storage device. The first implantable medical device includes a first therapy delivery unit powered by the first charge storage device. The first therapy delivery unit delivers a first therapy to a first target tissue of a patient. The system also includes a second implantable medical device configured to receive a second far field radiative signal at a second frequency from the external transmitter to charge a second charge storage device. The second implantable medical device includes a second therapy delivery unit powered by the second charge storage device. The second therapy delivery unit delivers a second therapy to a second target tissue of the patient.

23 Claims, 22 Drawing Sheets

Related U.S. Application Data a continuation-in-part of application No. 13/433,907, filed on Mar. 29, 2012, and a continuation-in-part of application No. 13/434,119, filed on Mar. 29, 2012, now Pat. No. 8,989,867.

(51) Int. Cl.
  *A61N 1/40* (2006.01)
  *A61N 1/36* (2006.01)

(56) References Cited

U.S. PATENT DOCUMENTS

| | | | |
|---|---|---|---|
| 6,289,238 B1 | 9/2001 | Besson | |
| 6,321,067 B1 | 11/2001 | Suga et al. | |
| 7,245,117 B1 | 7/2007 | Joy | |
| 7,481,771 B2 | 1/2009 | Fonseca | |
| 7,725,195 B2 | 5/2010 | Lima et al. | |
| 8,014,865 B2 | 9/2011 | Najafi et al. | |
| 8,634,928 B1 | 1/2014 | O'Driscoll et al. | |
| 8,989,867 B2 | 3/2015 | Chow et al. | |
| 2003/0171792 A1 | 9/2003 | Zarinetchi et al. | |
| 2004/0172083 A1* | 9/2004 | Penner | 607/35 |
| 2005/0134435 A1 | 6/2005 | Koyama et al. | |
| 2006/0232408 A1 | 10/2006 | Nycz et al. | |
| 2007/0055308 A1 | 3/2007 | Haller et al. | |
| 2007/0118187 A1 | 5/2007 | Denker et al. | |
| 2007/0145830 A1 | 6/2007 | Lee et al. | |
| 2008/0108915 A1 | 5/2008 | Penner | |
| 2008/0143531 A1 | 6/2008 | Tadokoro | |
| 2009/0069648 A1 | 3/2009 | Irazoqui et al. | |
| 2009/0105782 A1 | 4/2009 | Mickle et al. | |
| 2009/0253960 A1 | 10/2009 | Takenaka et al. | |
| 2009/0270948 A1 | 10/2009 | Nghiem et al. | |
| 2010/0010565 A1 | 1/2010 | Lichtenstein et al. | |
| 2010/0179449 A1 | 7/2010 | Chow et al. | |
| 2010/0228308 A1 | 9/2010 | Cowan et al. | |
| 2010/0256710 A1* | 10/2010 | Dinsmoor | A61N 1/3787 607/61 |
| 2011/0068766 A1 | 3/2011 | Nag et al. | |
| 2011/0234012 A1 | 9/2011 | Yi et al. | |
| 2012/0095531 A1* | 4/2012 | Derbas et al. | 607/68 |
| 2013/0018438 A1 | 1/2013 | Chow et al. | |
| 2013/0018439 A1 | 1/2013 | Chow et al. | |
| 2013/0018440 A1 | 1/2013 | Chow et al. | |
| 2013/0257167 A1 | 10/2013 | Singh | |
| 2013/0261703 A1 | 10/2013 | Chow et al. | |
| 2014/0055088 A1* | 2/2014 | Joshi | H02J 7/025 320/108 |
| 2015/0018728 A1* | 1/2015 | Gross et al. | 601/46 |

OTHER PUBLICATIONS

"Solx, Inc.," found at: http:www.solx.com/; 2011; printed on Aug. 14, 2014.

Akkermans, J.A.G. et al., "Analytical models for low-power rectenna design," Antennas and Wireless Propagation Letters, IEEE, vol. 4, No., pp. 187-190, 2005; doi: 10.1109/LAWP.2005.850798; found at: http://ieeexplore.ieee.org/stamp/stamp.jsp?tp=&arnumber=1435362&isnumber=30362.

Baker, M.W. et al., "Feedback Analysis and Design of RF Power Links for Low-Power Bionic Systems," Biomedical Circuits and Systems, IEEE Transactions on , vol. 1, No. 1, pp. 28-38, Mar. 2007; doi 10.1109/TBCAS.2007.893180; found at: http://ieeexplore.ieee.org/stamp/stamp.jsp?tp=&arnumber=4156129&isnumber=4156127.

Balanis, C. A., *Advanced Engineering Electromagnetics*. New York: Wiley, 1989, pp. 39-98, and 123-258.

Brown, W.C., "The History of Power Transmission by Radio Waves," *Microwave Theory and Techniques, IEEE Transactions on*, vol. 32, pp. 1230-1242, 1984.

Chaimanonart, N.; et al., "Remote RF powering system for wireless MEMS strain sensors," Sensors Journal, IEEE , vol. 6, No. 2, pp. 484-489, Apr. 2006; doi: 10.1109/JSEN.2006.870158; found at: http://ieeexplore.ieee.org/stamp/stamp.jsp?tp=&arnumber=1608093&isnumber=33774.

Chen, Z.N. et al., "Small Printed Ultrawideband Antenna With Reduced Ground Plane Effect," *Antennas and Propagation, IEEE Transactions on*, vol. 55, pp. 383-388, 2007.

Cheng, S. et al., "Printed Slot Planar Inverted Cone Antenna for Ultrawideband Applications," *Antennas and Wireless Propagation Letters, IEEE*, vol. 7, pp. 18-21, 2008.

Chow, E. et al., "Evaluation of Cardiovascular Stents as Antennas for Implantable Wireless Applications," *Microwave Theory and Techniques, IEEE Transactions on*, vol. 57, pp. 2523-2532, 2009.

Chow, E. Y. et al., "A Miniature-Implantable RF-Wireless Active Glaucoma Intraocular Pressure Monitor," *Biomedical Circuits and Systems, IEEE Transactions on*, vol. 4, pp. 340-349, 2010.

Chow, E. Y. et al., "Fully Wireless Implantable Cardiovascular Pressure Monitor Integrated with a Medical Stent," *Biomedical Engineering, IEEE Transactions on*, vol. 57, pp. 1487-1496, 2010.

Chow, E. Y. et al., "High Data-Rate 6.7 GHz Wireless ASIC Transmitter for Neural Prostheses," in *Engineering in Medicine and Biology Society, 2007. EMBS 2007. 29th Annual International Conference of the IEEE*, 2007, pp. 6580-6583.

Chow, E. Y. et al., "High frequency transcutaneous transmission using stents configured as a dipole radiator for cardiovascular implantable devices," in *Microwave Symposium Digest, 2009. MTT '09. IEEE MTT-S International*, 2009, pp. 1317-1320.

Chow, E. Y. et al., "Implantable Wireless Telemetry Boards for In Vivo Transocular Transmission," *Microwave Theory and Techniques, IEEE Transactions on*, vol. 56, pp. 3200-3208, 2008.

Chow, E. Y. et al., "Miniature antenna for RF telemetry through ocular tissue," in *Microwave Symposium Digest, 2008 IEEE MTT-S International*, 2008, pp. 1309-1312.

Chow, E. Y. et al., "Mixed-signal integrated circuits for self-contained sub-cubic millimeter biomedical implants," in *Solid-State Circuits Conference Digest of Technical Papers (ISSCC), 2010 IEEE International*, 2011, pp. 236-237.

Chow, E. Y. et al., "Toward an Implantable Wireless Cardiac Monitoring Platform Integrated with an FDA-Approved Cardiovascular Stent," *Journal of Interventional Cardiology*, vol. 22, pp. 479-487, 2009.

Chow, E. Y. et al.,, "Sub-cubic millimeter intraocular pressure monitoring implant to enable genetic studies on pressure-induced neurodegeneration," in *Engineering in Medicine and Biology Society (EMBC), 2010 Annual International Conference of the IEEE*, 2010, pp. 6429-6432.

Chow, E. Y. et al.; "Chapter 9: Wireless Powering and Propagation of Radio Frequencies through Tissue," in *Wireless Power Transfer*, J. Agbinya, Ed., Aalborg, Denmark: River Publishers, Jul. 2012, pp. 301-336.

Chow, E.Y. et al., "Wireless Powering and the Study of RF Propagation Through Ocular Tissue for Development of Implantable Sensors," *Antennas and Propagation, IEEE Transactions on*, vol. 59, pp. 2379-2387, 2011.

Curty, Jari-Pascal et al., A Model for—Power Rectifier Analysis and Design, IEEE Transactions On Circuits and Systems—I: Regular Papers, vol. 52, No. 12, Dec. 2005, pp. 2771-2779.

Dolgov, A.; et al., "Power Management System for Online Low Power RF Energy Harvesting Optimization," Circuits and Systems I: Regular Papers, IEEE Transactions on , vol. 57, No. 7, pp. 1802-1811, Jul. 2010; doi: 10.1109/TCSI.2009.2034891; found at: http://ieeexplore.ieee.org/stamp/stamp.jsp?tp=&arnumber=5395599&isnumber=5512812.

Douyere, A. et al., "High efficiency microwave rectenna circuit: modelling and design," Electronics Letters , vol. 44, No. 24, pp. 1409-1410, Nov. 20, 2008 doi: 10.1049/el:20081794 URL: http://ieeexplore.ieee.org/stamp/stamp.jsp?tp=&arnumber=4689488&isnumber=4689470.

Everhart, E. et al. ;The Cockcroft Walton Voltage Multiplying Circuit Rev. Sci. Instrum. 25, 394 (1954); found at: http://rsi.aip.org/resource/1/rsinak/v25/i4/p394_s1?isAuthorized=no.

Fischell, R.E., "The retrospectroscope—the invention of the rechargeable cardiac pacemaker: vignette #9," *Engineering in Medicine and Biology Magazine, IEEE*, vol. 9, pp. 77-78, 1990.

(56) References Cited

OTHER PUBLICATIONS

Gabriel, C. et al., "Compilation of the dielectric properties of body tissues at RF and microwave frequencies," *Report N.AL/OE-TR-1996-0037, Occupational and environmental health directorate, Radiofrequency Radiation Division, Brooks Air Force Base, Texas (USA)*, 1996.

Gabriel, C. et al., "The dielectric properties of biological tissues: I. Literature survey." vol. 41, 1996, p. 2231.

Gabriel, S. et al., "The dielectric properties of biological tissues: II. Measurements in the frequency range 10 Hz to 20 GHz." vol. 41, 1996, p. 2251.

Gabriel, S. et al., "The dielectric properties of biological tissues: III. Parametric models for the dielectric spectrum of tissues." vol. 41, 1996, p. 2271.

Glaser, P., "Satellite solar power station and microwave transmission to earth," *Journal of Microwave Power*, vol. 5, 1970.

Hagerty, J.A. et al., "Recycling ambient microwave energy with broad-band rectenna arrays," Microwave Theory and Techniques, IEEE Transactions on , vol. 52, No. 3, pp. 1014-1024, Mar. 2004 doi: 10.1109/TMTT.2004.823585 found at: http://ieeexplore.ieee.org/stamp/stamp.jsp?tp=&arnumber=1273745&isnumber=28503.

Humayun, M.S., et al., "Visual perception in a blind subject with a chronic microelectronic retinal prosthesis," *Vision Research*, vol. 43, pp. 2573-2581, 2003.

Icnirp, "Guidelines for limiting exposure to time-varying electric, magnetic and electromagnetic fields (up to 200 GHz)," *Health Physics*, vol. 74, pp. 494-522, 1998.

Icnirp, "Guidelines for limiting exposure to time-varying electric and magnetic fields (1 Hz to 100 kHz)," *Health Physics*, vol. 99, pp. 818-836, 2010.

Icnirp, "Guidelines for limiting exposure to time-varying electric, magnetic, and electromagnetic fields (up to 300 GHz)," *Health Phys.*, vol. 74, pp. 494-522, 1998.

Joshi, R. K. et al., "Printed wideband variable strip width loop antenna," in *Antennas and Propagation Society International Symposium, 2007 IEEE*, 2007, pp. 4793-4796.

Karacolak, T. et al., "Design of a Dual-Band Implantable Antenna and Development of Skin Mimicking Gels for Continuous Glucose Monitoring," *Microwave Theory and Techniques, IEEE Transactions on*, vol. 56, pp. 1001-1008, 2008.

Knapp, J.P., "ANSYS Inc. Request for Waiver of 47 C.F.R. § 1.1307(b)(2) of Commission Rules, DA 11-192," Federal Communications Commission, 2011.

Lin, Yi-Cheng. et al., "Compact Ultrawideband Rectangular Aperture Antenna and Band-Notched Designs," *Antennas and Propagation, IEEE Transactions on*, vol. 54, pp. 3075-3081, 2006.

Ling, Ching-Wei et al., "A Simple Printed Ultrawideband Antenna With a Quasi-Transmission Line Section," *Antennas and Propagation, IEEE Transactions on*, vol. 57, pp. 3333-3336, 2009.

Margalit, E., et al., "Retinal Prosthesis for the Blind," *Survey of Ophthalmology*, vol. 47, pp. 335-356, 2002.

Means, D. L. et al., "Evaluating Compliance with FCC Guidelines for Human Exposure to Radiofrequency Electromagnetic Fields," *OET Bulletin 65 (Edition 97-01) Supplement C (Edition 01-01)*, Federal Communications Commission Office of Engineering & Technology, 2001.

Najafi, N. et al., "Initial Animal Studies of a Wireless, Batteryless, MEMS Implant for Cardiovascular Applications " *Biomedical Microdevices*, vol. 6, pp. 61-65, 2004.

Nazli, H. et al., "An Improved Design of Planar Elliptical Dipole Antenna for UWB Applications," *Antennas and Wireless Propagation Letters, IEEE*, vol. 9, pp. 264-267, 2010.

Ogden, C. L., et al., "Mean Body Weight, Height, and Body Mass Index, United States 1960-2002," *Centers for Disease Control and Prevention*, vol. 347, 2004.

Ojaroudi, M. et al., "Small Square Monopole Antenna With Enhanced Bandwidth by Using Inverted T-Shaped Slot and Conductor-Backed Plane," *Antennas and Propagation, IEEE Transactions on*, vol. 59, pp. 670-674, Feb. 2011.

Oraizi, H. et al., "Miniaturized UWB Monopole Microstrip Antenna Design by the Combination of Giusepe Peano and Sierpinski Carpet Fractals," *Antennas and Wireless Propagation Letters, IEEE*, vol. 10, pp. 67-70, 2011.

Paing, T. et al., "Resistor Emulation Approach to Low-Power RF Energy Harvesting," Power Electronics, IEEE Transactions on , vol. 23, No. 3, pp. 1494-1501, May 2008 doi: 10.1109/TPEL.2008.921167; found at: http://ieeexplore.ieee.org/stamp/stamp.jsp?tp=&arnumber=4492966&isnumber=4509502.

Ramo, S. et al., *Fields and Waves in Communication Electronics*, 3rd ed.: John Wiley & Sons, Inc., 1994, pp. 274-313, 584-668, 667-733.

Ren, Yu-Jiun et al., "5.8-GHz circularly polarized dual-diode rectenna and rectenna array for microwave power transmission," Microwave Theory and Techniques, IEEE Transactions on , vol. 54, No. 4, pp. 1495-1502, Jun. 2006; doi: 10.1109/TMTT.2006.871362; found at: http://ieeexplore.ieee.org/stamp/stamp.jsp?tp=&arnumber=1618568&isnumber=33917.

Ritzema, J. et al., "Direct Left Atrial Pressure Monitoring in Ambulatory Heart Failure Patients," *Circulation*, vol. 116, pp. 2952-2959, 2007.

Ryu, K. S. et al., "UWB Dielectric Resonator Antenna Having Consistent Omnidirectional Pattern and Low Cross-Polarization Characteristics," *Antennas and Propagation, IEEE Transactions on*, vol. 59, pp. 1403-1408, Apr. 2011.

Soontornpipit, P. et al., "Design of implantable microstrip antenna for communication with medical implants," *Microwave Theory and Techniques, IEEE Transactions on*, vol. 52, pp. 1944-1951, 2004.

Sun, X. et al.; "Design of Several Key Circuits of UHF Passive RFID Tag"; *China Integrated Circuit*, vol. 16, 2007 (Institute of Microelectronics of Tsinghua University); found at: http://en.cnki.com.cn/Articie_en/CJFDTOTAL-JCDI200701009.htm.

Sze, Jia-Yi et al., "Design of Band-Notched Ultrawideband Square Aperture Antenna With a Hat-Shaped Back-Patch," *Antennas and Propagation, IEEE Transactions on*, vol. 56, pp. 3311-3314, 2008.

Tesla, Nikola; Colorado Springs Notes 1899-1900; found at: http://www.scribd.com/doc/41567714/Nikola-Tesla-Colorado-Springs-Notes-1899-1900.

Thomas, K. G., et al., "A Simple Ultrawideband Planar Rectangular Printed Antenna With Band Dispensation," *Antennas and Propagation, IEEE Transactions on*, vol. 58, pp. 27-34, Jan. 2010.

Yanai, D., et al., "Visual Performance Using a Retinal Prosthesis in Three Subjects With Retinitis Pigmentosa," *American Journal of Ophthalmology*, vol. 143, pp. 820-827.e2, 2007.

Yazdanboost, K. Y. et al., "Ultra wideband L-loop antenna," in *Ultra-Wideband, 2005. ICU 2005. 2005 IEEE International Conference on*, 2005, pp. 201-205.

Zbitou, J.; et al. , "Hybrid rectenna and monolithic integrated zero-bias microwave rectifier," Microwave Theory and Techniques, IEEE Transactions on , vol. 54, No. 1, pp. 147-152, Jan. 2006 doi: 10.1109/TMTT.2005.860509 found at: URL: http://ieeexplore.ieee.org/stamp/stamp.jsp?tp=&arnumber=1573807&isnumber=33279.

Zhang, Jin-Ping. et al., "Microstrip-Fed Semi-Elliptical Dipole Antennas for Ultrawideband Communications," *Antennas and Propagation, IEEE Transactions on*, vol. 56, pp. 241-244, 2008.

Bowditch, N., The American Practice Navigator, National Imagery and Mapping Agency, Bethesda Maryland, 2002, 1 page.

Extended European Search Report for EP Application No. 15189806.1, mail date Feb. 10, 2016, 5 pages.

International Search Report & Written Opinion for PCT Application No. PCT/US2014/035309, dated Jul. 23, 2014, 11 pages.

Office Action for Canadian Patent Application No. 2841406, dated Jun. 30, 2016, 5 pages.

\* cited by examiner

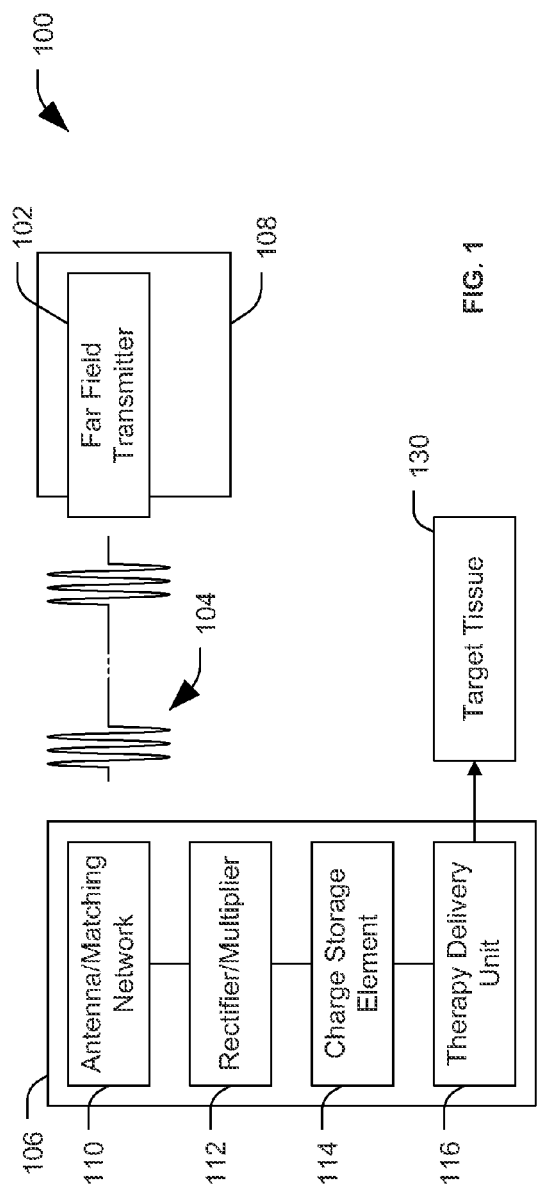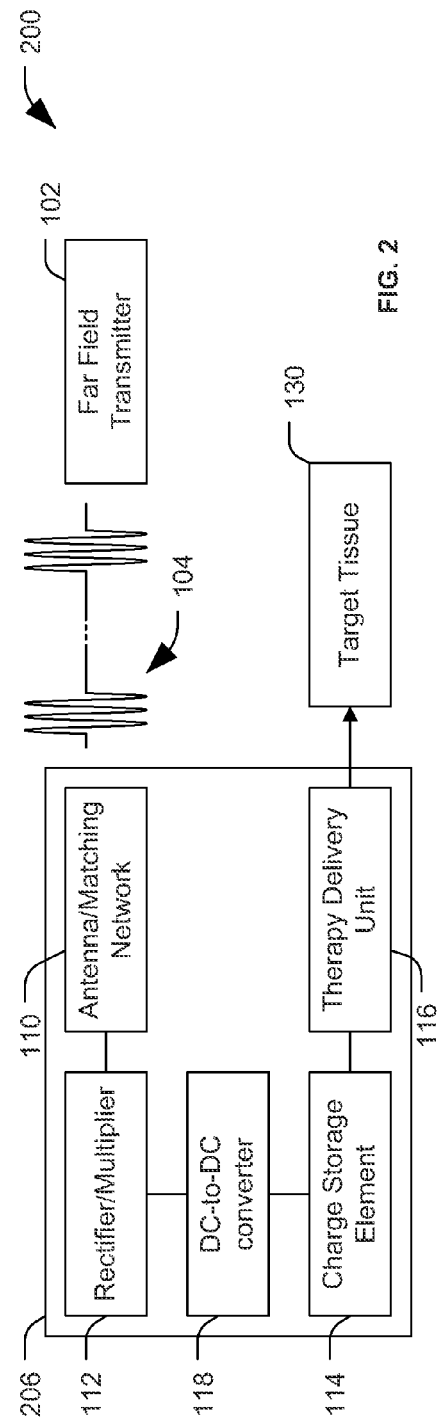

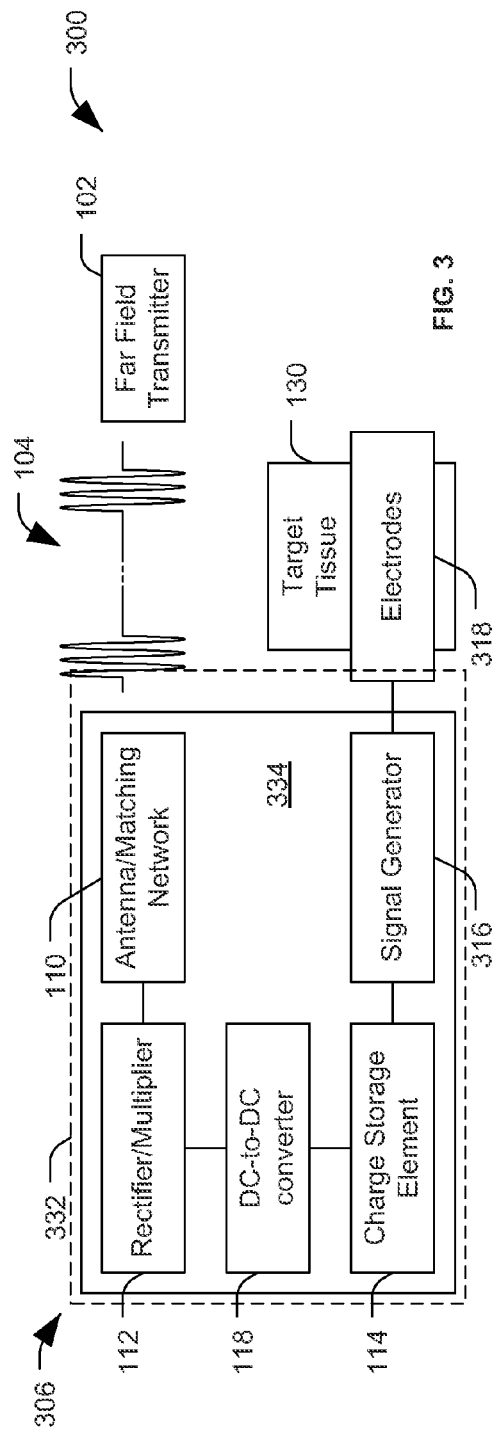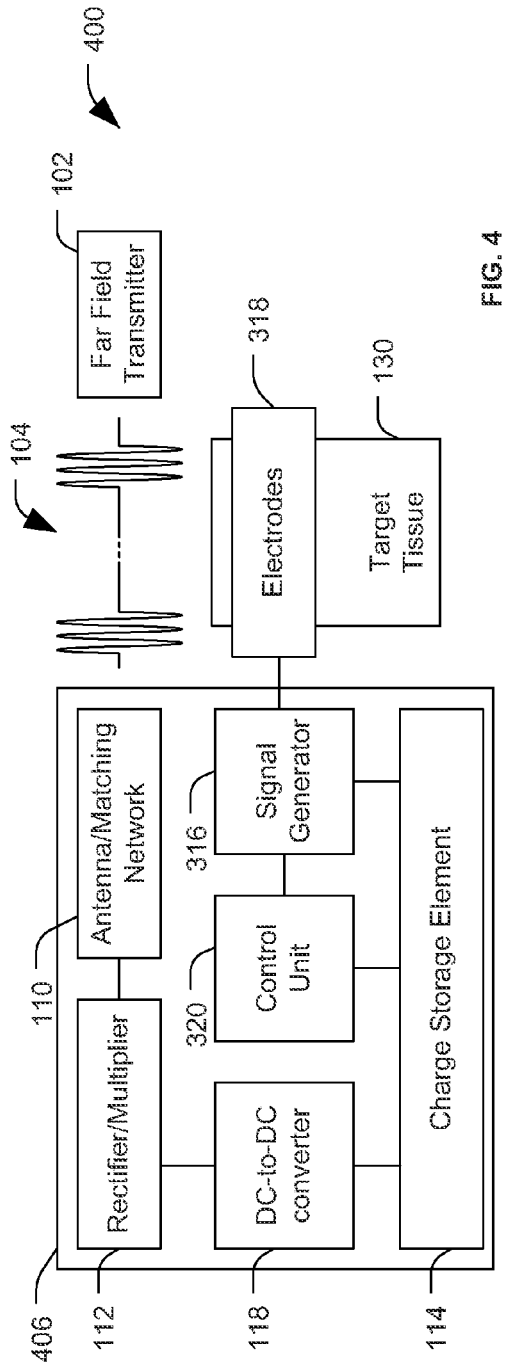

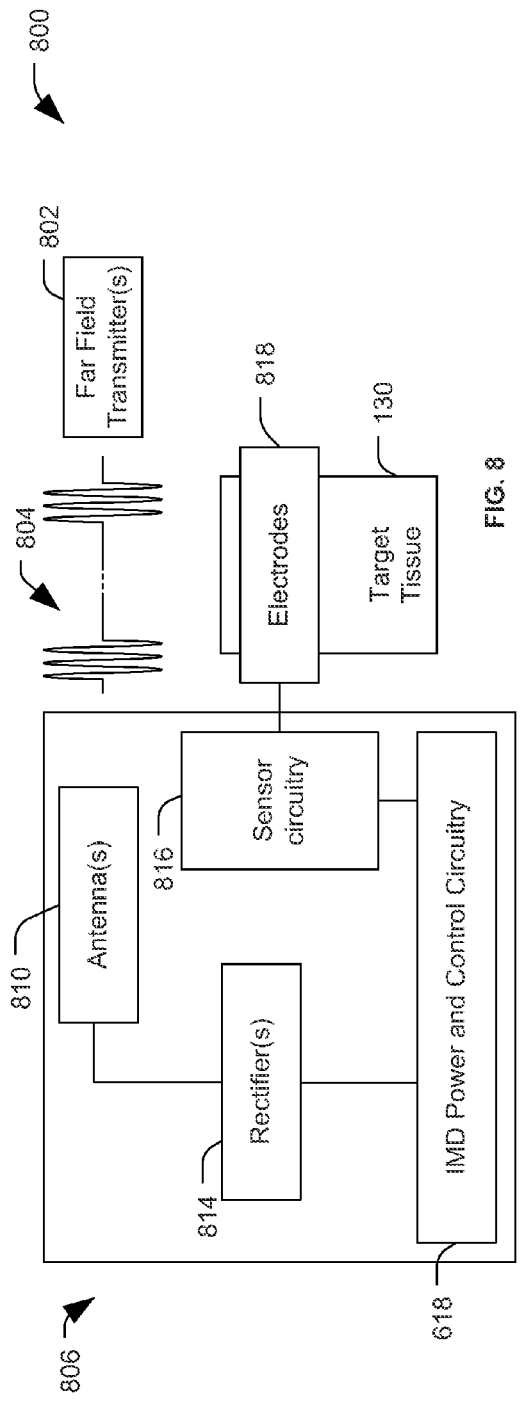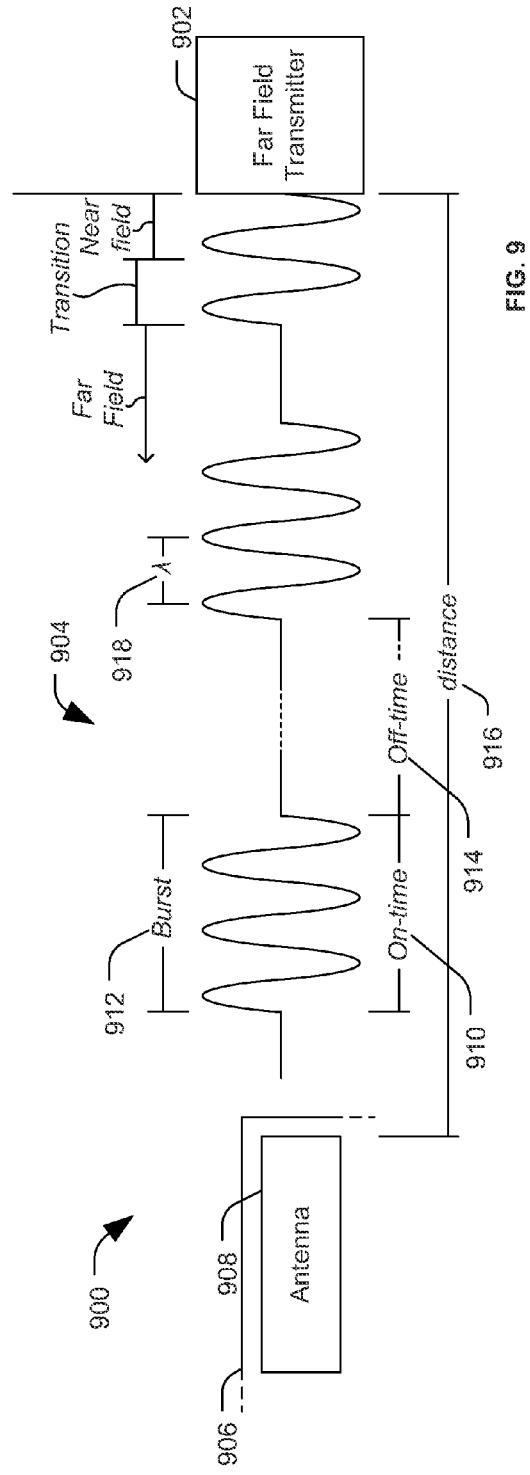

POWERING MULTIPLE IMPLANTABLE MEDICAL THERAPY DELIVERY DEVICES USING FAR FIELD RADIATIVE POWERING AT MULTIPLE FREQUENCIES

CROSS-REFERENCE TO RELATED APPLICATIONS

This application is a continuation-in-part of and claims priority to U.S. patent application Ser. No. 13/434,240, entitled "Powering Of An Implantable Medical Therapy Delivery Device Using Far Field Radiative Powering At Multiple Frequencies," filed on Mar. 29, 2012; U.S. patent application Ser. No. 13/433,907, entitled "Far Field Radiative Powering Of Implantable Medical Therapy Delivery Devices" filed Mar. 29, 2012; and U.S. patent application Ser. No. 13/434,119, entitled "Implantable Nerve Wrap For Nerve Stimulation Configured For Far Field Radiative Powering," filed Mar. 29, 2012, now U.S. Pat. No. 8,989,867, all of which are hereby incorporated by reference in their entirety.

FIELD OF THE DISCLOSURE

The present disclosure is generally related to far field radiative powering of implantable medical devices.

BACKGROUND

Powering implantable medical devices can be problematic. Many implantable medical devices include a battery. If the battery is rechargeable, the implantable medical device may include charging components to receive power from an external source to recharge the battery. For example, the implantable medical device may include a coil that is operative to inductively couple with an external coil. Providing power via inductive coupling may require that the coil of the implantable medical device and the external coil be relatively close to one another (e.g., within a distance over which a magnetic field is relatively strong). Further, inductive coupling may be less efficient when the coil of the implantable medical device and the external coil are not aligned or oriented properly.

SUMMARY

In one embodiment, a system may include a first implantable medical device configured to receive a first far field radiative signal at a first frequency from an external transmitter. The first implantable medical device may charge a first charge storage device using the first far field radiative signal. The first implantable medical device may include a first therapy delivery unit powered by the first charge storage device. The first therapy delivery unit may be configured to deliver a first therapy to a first target tissue of a patient, where the first therapy includes delivery of a first electrical stimulation signal to the first target tissue. The system may also include a second implantable medical device configured to receive a second far field radiative signal at a second frequency from the external transmitter. The second implantable medical device may charge a second charge storage device using the second far field radiative signal. The second implantable medical device may include a second therapy delivery unit powered by the second charge storage device. The second therapy delivery unit may be configured to deliver a second therapy to a second target tissue of the patient, where the second therapy includes delivery of a second electrical stimulation signal to the second target tissue.

In one embodiment, a system may include an external transmitter that transmits a first far field radiative signal at a first frequency and a second far field radiative signal at a second frequency different from the first frequency. The system may also include a first implantable medical device configured to receive the first far field radiative signal from an external transmitter and to charge a first charge storage device using the first far field radiative signal. The first implantable medical device may include a first therapy delivery unit powered by the first charge storage device and configured to deliver a first therapy to a first target tissue of a patient. The first therapy may include delivery of a first electrical stimulation signal to the first target tissue. The system may also include a second implantable medical device configured to receive a second far field radiative signal from the external transmitter and to charge a second charge storage device using the second far field radiative signal. The second implantable medical device may include a second therapy delivery unit powered by the second charge storage device and configured to deliver a second therapy to a second target tissue of the patient. The second therapy may include delivery of a second electrical stimulation signal to the second target tissue.

In one embodiment, an external device may include a first external transmitter configured to transmit a first far field radiative charging signal at a first frequency to a first implantable medical device according to a treatment protocol. The first far field radiative charging signal may be configured to charge the first implantable medical device. The first implantable medical device may be configured to deliver a first therapy to a first target tissue of a patient. The external device may also include a second external transmitter configured to transmit a second far field radiative charging signal at a second frequency to a second implantable medical device according to the treatment protocol. The second far field radiative charging signal may be configured to charge the second implantable medical device. The second implantable medical device may be configured to deliver a second therapy to a second target tissue of the patient.

In a particular embodiment, an implantable medical device may include a first antenna configured to receive a first far field radiative signal in a first frequency band and may include a second antenna configured to receive a second far field radiative signal in a second frequency band. The implantable medical device may also include a voltage rectifier configured to rectify the received first far field radiative signal and the received second far field radiative signal to provide a rectified voltage signal. The implantable medical device may further include a charge storage element operative to receive the rectified voltage signal and to store charge responsive to the rectified voltage signal. The implantable medical device may also include a therapy delivery unit powered by the charge storage element. The therapy delivery unit may be operative to deliver a therapy to a patient.

In a particular embodiment, a method includes receiving a first far field radiative signal and a second far field radiative signal at an implantable medical device. The method may include rectifying the received first far field radiative signal and the received second far field radiative signal to provide a voltage. The method may also include charging a charge storage element of the implantable medical device responsive to the voltage. The method may further include providing a therapy to a patient using a therapy delivery unit of the implantable medical device. The therapy delivery may receive power from the charge storage element.

In a particular embodiment, an implantable medical device may include a multiband antenna configured to receive a first far field radiative signal in a first frequency band and to receive a second far field radiative signal in a second frequency band. The implantable medical device may also include a voltage rectifier configured to rectify the first far field radiative signal and the second radiative received by the multiband antenna to provide a rectified voltage signal. The implantable medical device may further include a charge storage element operative to receive the rectified voltage signal and to store charge responsive to the rectified voltage signal. The implantable medical device may also include a therapy delivery unit powered by the charge storage element. The therapy delivery unit may be operative to deliver a therapy to a patient.

In a particular embodiment, a system includes a first external transmitter configured to transmit a first far field radiative signal and a second external transmitter configured to transmit a second far field radiative signal. The system includes an implantable medical device configured to receive the first far field radiative signal and the second far field radiative signal. The implantable medical device may include a charge storage element that is operative to store a charge responsive to the received first far field radiative signal and the received second far field radiative signal. The implantable medical device may include a pulse generator powered by the charge storage element. The pulse generator may be operative to generate an electrical stimulation signal to stimulate a target tissue of a patient.

The features, functions, and advantages that have been described can be achieved independently in various embodiments or may be combined in yet other embodiments, further details of which are disclosed with reference to the following description and drawings.

BRIEF DESCRIPTION OF THE DRAWINGS

FIG. 1 is a block diagram of a first particular embodiment of a system including an implantable medical device and a far field transmitter;

FIG. 2 is a block diagram of a second particular embodiment of a system including an implantable medical device and a far field transmitter;

FIG. 3 is a block diagram of a third particular embodiment of a system including an implantable medical device and a far field transmitter;

FIG. 4 is a block diagram of a fourth particular embodiment of a system including an implantable medical device and a far field transmitter;

FIG. 8 is a block diagram of an eighth particular embodiment of a system including an implantable medical device and a far field transmitter;

FIG. 9 is diagram illustrating a particular embodiment of powering an implantable medical device using a far field transmitter;

DETAILED DESCRIPTION

Figure 5:
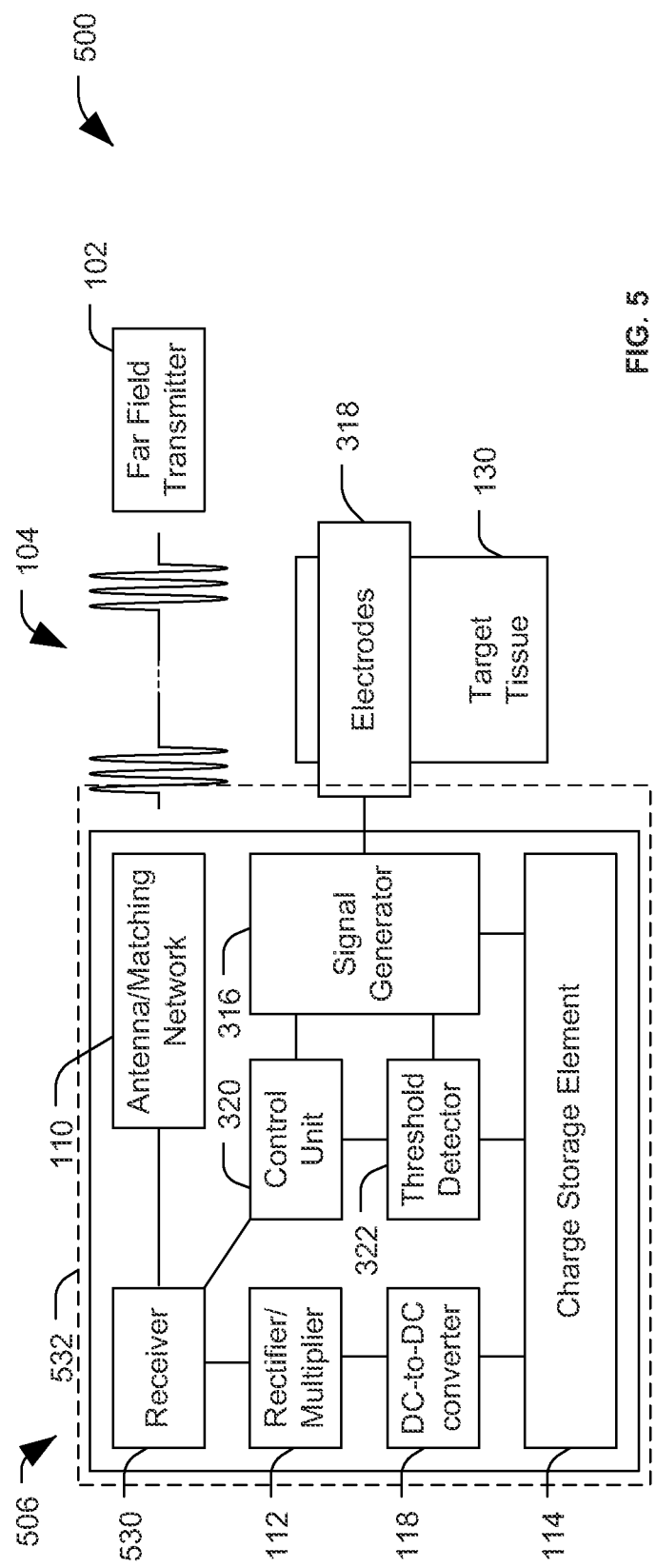
FIG. 5 is a block diagram of a fifth particular embodiment of a system including an implantable medical device and a far field transmitter.

Disclosed systems, methods and devices enable powering of implantable medical devices using far-field radiative signals. Using far field radiative signals to power an implantable medical device may enable miniaturization of the implantable medical device since no onboard power storage (or no long-term onboard power storage) is required. Far field radiative powering, especially in combination with miniaturization of the implantable medical device, may enable use of reduced complexity procedures to implant the implantable medical device and may enable use of the implantable medical device in new areas of the body. Particular embodiments may provide effective screening tools to determine whether a particular type of treatment will be effective for a particular patient.

Disclosed implantable medical devices may be used to treat various conditions by applying treatment to one or more tissues of a patient's body. To illustrate, an implantable medical device may be used to target neural tissue by inducing efferent or afferent action potentials in the neural tissue or by blocking intrinsic efferent or afferent action potentials in the neural tissue. For example, the implantable medical device may be used to target a vagus or trigeminal nerve to treat one or more conditions, such as epilepsy or other seizure inducing conditions. In another example, the implantable medical device may target an optic nerve to treat a vision condition or to supplement or facilitate use of a visual prosthesis for sight restoration. In another example, the implantable medical device may target a hypoglossal nerve to treat one or more conditions, such as sleep apnea. Although the examples above each relate to cranial nerves, the implantable medical device may be used to target another nerve or set of nerves rather than or in addition to a cranial nerve. For example, the implantable medical device may be used to target a sacral nerve to treat one or more conditions, such as to facilitate bladder control. In another example, the implantable medical device may be used to target a phrenic nerve to treat one or more conditions, such as to facilitate diaphragm or respiration control. In another example, the implantable medical device may be used to target one or more nerves of the spinal cord to treat one or more conditions, such as to facilitate pain management. Further, in addition to or instead of targeting a neural tissue, the implantable medical device may be used to target other tissue of a patient's body. For example, the implantable medical device may be used to stimulate a muscle to induce muscle contraction. To illustrate, the implantable medical device may target a heart muscle to act as a pacemaker. Other examples of conditions that may be treated using an implantable medical device that is at least partially powered by far field radiative power include, but are not limited to, traumatic brain injury and depression.

FIG. 1 is a block diagram of a first particular embodiment of a system 100 including an implantable medical device 106 and an external device 108. The implantable medical device 106 may be wirelessly powered by the external device 108. For example, the external device 108 may emit electromagnetic energy by transmitting radio-frequency signals using an external antenna (e.g., the far field transmitter 102). At least a portion of the electromagnetic energy may be received by an antenna of the implantable medical device 106 as far field radiative signals 104. In another example, the implantable medical device 106 may receive energy via near-field signals (e.g., by inductive coupling of the antenna of the implantable medical device 106 and an antenna of the far field transmitter 102). In yet another example, the implantable medical device 106 may receive energy via near-field signals and via far field radiative signals 104, either simultaneously or at different times.

Electromagnetic energy may be described as propagating through a near field region in which the magnetic fields are relatively strong, a far field region in which the magnetic fields are relatively weak, and a transition region between the near field region and the far field region. Although there is no generally accepted firm boundary between these regions, as used herein, and as illustrated in FIG. 9, the near field region refers to a region within about one wavelength of a source of the electromagnetic energy (e.g., a transmitting antenna), and the far field region refers to a region two wavelength or more from the source of the electromagnetic energy. Thus, a magnetic field is likely to be insignificant in the far field region. Conversely, the magnetic field may dominate in the near field region. Non-radiative mechanisms, such as inductive or capacitive coupling, operate over a relatively short distance and may be used to transfer energy in the near field region. Non-radiative mechanisms generally operate based on the principle that a circulating current can produce a magnetic field component which can induce an opposing current in a nearby structure. The magnetic field dissipates rapidly with distance. Near-field interactions can be extremely complex because they are reactive. That is, a transmit structure and transmitted electromagnetic fields react to receive structures and electromagnetic absorption in the vicinity. Approximate relationships descriptive of the near field region indicate that the near-field magnetic field strength decreases with the inverse-cube of distance and the near-field electric field decreases with the inverse-square, and thus, the power density in the near field region decreases as the inverse of the distance to the fifth power. Accordingly, for sufficient distances (typically around a wavelength or greater) the power quickly reduces to negligible levels. In contrast, for far-field radiative power transfer, the receive structure and its absorption does not affect the transmitter structure or the power output from the transmitter structure. The electric and magnetic fields from far-field radiative power transfer are better understood and both are inversely proportional to the distance and thus, the power is inversely proportional to the distance squared in the far field region.

From a clinical perspective, using non-radiative energy transfer may place limitations on the mobility of the patient and may lead to user error in patient populations. For example, non-radiative energy transfer mechanisms operate over a relatively short range and therefore require relatively short distances between an implanted medical device and an external charging device, which may limit patient mobility. Further, power may only be efficiently transferred via a non-radiative mechanism when a receiving component of the implanted medical device has a particular orientation with respect to a transmitting component of the external charging device. Maintaining this orientation can be difficult when the patient is moving (even breathing), which may further limit the patient's mobility.

Far field radiative signals 104 may be used to transfer power over a greater distance using radiative mechanisms. For example, the far field radiative signals 104 may transmit energy through free space using electrical fields propagating between a broad-beam external antenna and an internal antenna of the implantable medical device 106. This arrangement may allow greater freedom of placement for the external device 108 with respect to the patient. To illustrate, the external device 108 may be worn by or carried by the patient or may be positioned near the patient. As an illustrative example, when the implantable medical device 106 is implanted in the neck of the patient, the external device 108 may be worn by the patient, such as near the patient's upper arm or around the patient's neck. In another illustrative example, the external device 108 may include or be included within a mounted or table top power source.

As further described below, the implantable medical device 106 may include an antenna to receive the far field radiative signals 104, a matching network to impedance match the antenna with other components of the implantable medical device 106, power processing elements (e.g., a rectifier, a voltage multiplier, a step-up regulator, etc.), a charge storage element 114, and a therapy deliver unit 116. The implantable medical device 106 may use power derived at least partially from the far field radiative signals 104 to deliver therapy to a patient.

In a particular embodiment, the implantable medical device 106 includes an antenna and an associated matching network. In the embodiment illustrated in FIG. 1, the antenna and the matching network are illustrated as a single antenna/matching network 110 component; however, in other embodiments, the antenna and the matching network may be separate components. Thus, the antenna may include, be included within, or be coupled to the matching network. The antenna may be a dipole antenna, a monopole antenna, a serpentine antenna, a slot antenna, a patch antenna, a plane-inverted-F antenna (PIFA), a helical antenna, a fractal antenna, a loop antenna, or an antenna with another form factor configured to receive the far field radiative signals 104. The matching network may be adapted to match impedance of the antenna to other components of the implantable medical device 106 to achieve high efficiency power transfer. For example, the resistance of the antenna may be relatively low (e.g., on the order of a few ohms for electrically-small antennas and up to 50 ohms for electrically-large antennas) and one or more other components of the implantable medical device 106 may have a comparatively high resistance (e.g., on the order of KOhms). To illustrate, the antenna may have an impedance with a real part of approximately 10 ohms or less. In another illustrative example, the antenna may have an impedance with a real part of approximately 50 ohms or less. The matching network may facilitate impedance matching from the relatively low resistance of the antenna to a relatively high resistance of some other components of the implantable medical device 106. For example, conjugate matching, i.e. equal real impedance (resistance) and equal in magnitude but opposite in sign imaginary impedance (reactance), may achieve optimal power transfer.

The far field radiative signals 104 may be relatively weak when received at the antenna of the implantable medical device 106. For example, due to regulatory and safety constraints, the far field radiative signals 104 may be transmitted at a relatively low transmission power, such as an instantaneous transmission power of 1 watt or less, or an instantaneous transmission power of 5 watts or less. In a particular embodiment, an amount of power transferred via the far field radiative signal 104 to the implantable medical device 106 can be increased by delivering the power using multiple frequencies or frequency bands, and/or by using multiple far field transmitters 102.

As explained above, the far field radiative signals 104 may be transmitted over a distance of at least twice a wavelength of the far field radiative signals 104. For example, the far field radiative signals 104 may be transmitted over a distance of several meters or less, such as one meter or less. The free-space path loss (FSPL) of the far field radiative signals 104 may be estimated as a function of the transmission power of the far field transmitter 102; the distance, d, between the far field transmitter 102 and the patient; and the frequency, f, of the far field radiative signals 104. In a particular embodiment, the far field radiative signals 104 have a frequency within a range of approximately 100 MHz to approximately 5.8 GHz. For example, the far field radiative signal may have a frequency at, or in a frequency band centered at, approximately 433 MHz, approximately 900 MHz, approximately 2.4 GHz, approximately 5.8 GHz, or another frequency within an unlicensed or licensed frequency spectrum.

Thus, free-space path loss of the far field radiative signals 104 may be significant. To illustrate, when the distance, d, between the far field transmitter 102 and the patient is about 1 meter and the far field radiative signals 104 have a frequency, f, of about 2.4 GHz, the free-space path loss (FSPL), assuming two isotropic antennas, may be approximately described by the following equation:

$$FSPL = \left(\frac{4\pi df}{c}\right)^2 = (32\pi d)^2 = (10,000).$$

Therefore, the FSPL is proportional to the square of the distance between the far field transmitter 102 and the patient. The power transfer efficiency is inversely proportional to the square of the distance between the far field transmitter 102 and the patient. The FSPL can also be provided in decibels as shown by the following equation:

$$FSPL(\text{dB}) = 10\log\left(\frac{4\pi df}{c}\right)^2$$
$$= 10\log(32\pi d)^2$$
$$= 10\log(10,000)$$
$$= 40 \text{ dB}$$

In a near-field region where magnetic fields are relatively strong, power transferred via a non-radiative mechanism, such as magnetic fields used by an inductive coil, may dissipate with distance. Further, power transfer via non-radiative mechanisms that rely on near-field interactions may react to receive structures and electromagnetic absorption in the vicinity. Magnetic fields used by an inductive coil may have a power transfer efficiency that is inversely proportional to the third power of the distance between the inductive coil and the patient. In contrast, power transfer by far field interactions is inversely proportional to the square of the distance between a far field transmitter and a patient. Therefore, far field power transfer enables greater efficiency of transfer of power across a far field region such that a transmitter structure or power output from the transmitter structure are not affected by a receive structure and its electromagnetic absorption.

Additionally, the implantable medical device 106 may be implanted under several centimeters of tissue of the patient, which may further attenuate the far field radiative signals 104. For example, when the implantable medical device 106 is implanted under one inch of fat, attenuation and impedance mismatch may result in approximately 6 dB of power loss. Thus, as the tissue losses become greater, the power received at the antenna decreases significantly.

Additionally, components of the implantable medical device 106 may further reduce power received via the far field radiative signals 104 that is available to provide therapeutic stimulation. For example, losses at the antenna may be expected to reduce the power by about 5-10 dB, and losses at a rectifier may be expected to reduce the power by about 10-20 dB. Efficient design of the components of the implantable medical device 106 may enable use of the far field radiative signals 104 to provide power for therapeutic stimulation. For example, as explained further below, efficiency of the antenna and the matching network may be increased by using accurate human body simulation models, RF phantoms, or animal or human models (ex vivo and/or in vivo) to test various proposed designs. In another example, efficiency of the rectifier may be increased by sending the far field radiative signals 104 as pulsed signals, by using Schottky diodes, or both.

The implantable medical device 106 may include one or more voltage rectifiers to rectify the far field radiative signals 104 to generate a rectified voltage. The implantable medical device 106 may include one or more voltage multipliers configured to multiply the far field radiative signals 104 received by the antenna 110 to provide a multiplied voltage signal. In the embodiment illustrated in FIG. 1, the voltage rectifier and the voltage multiplier are illustrated as a single rectifier/multiplier 112 component; however, in other embodiments, the voltage rectifier and the voltage multiplier may be separate components. For example, the voltage rectifier may include, be included within, or be coupled to the voltage multiplier.

In a particular embodiment, the voltage rectifier is a multi-stage rectifier, such as a multi-stage complementary rectifier. The voltage rectifier may include Schottky diodes. In a different implementation, diode functionality can be implemented using complementary metal-oxide-semiconductor (CMOS) devices, such as a transistor having the gate and drain shorted together, a p-n junction diode, or a Schottky diode. Schottky diodes generally have high frequency performance and low forward-bias voltage. For example, the Schottky diodes may have a forward bias voltage of 0.4 volts or less, 0.15 volts or less, or 0.1 volts or less at a frequency of interest (such as a frequency of the far field radiative signals 104). Low forward bias voltage of the voltage rectifier may enable rectification at lower input biases which may be desirable for low power operation. Low forward bias voltage of the voltage rectifier may also improve the efficiency of the power conversion at the implanted medical device as less power will be consumed forward biasing the voltage rectifier.

The charge storage element 114 may be operative to receive rectified voltage, multiplied voltage, or rectified and multiplied voltage and to store charge responsive to the received voltage. The charge storage element 114 may include a capacitor, a capacitor array, a rechargeable battery, a thin film battery, another charge storage element, or a combination thereof. The charge storage element 114 may provide power to other elements of the implantable medical device 106.

The therapy delivery unit 116 may be powered by the charge storage element 114. The therapy delivery unit 116 may be operative to deliver therapy to a target tissue 130 of the patient. For example, therapy delivery unit 116 may include a signal generator that is operative to apply electrical stimulation to the target tissue 130. In another example, the therapy delivery unit 116 is a drug delivery unit that is operative to deliver a drug as the therapy to the patient. The target tissue 130 may include neural tissue (e.g., one or more areas of the brain, the spinal cord, a cranial nerve, or another nerve), muscular tissue (e.g., a heart muscle), or other tissue. In a particular embodiment, the target tissue 130 includes one or more of a vagus nerve, a trigeminal nerve, a glossopharyngeal nerve, and a hypoglossal nerve.

In a particular embodiment, the charge storage element 114 may be sized or configured to store only enough charge to deliver the therapy during a short time period relative to typically implantable medical device batteries. To illustrate, the charge storage element 114 may store enough charge to deliver the therapy during a period of 3 days or less. In another example, the charge storage element 114 may store enough charge to deliver the therapy during a period of 24 hours or less. In other examples, the charge stored by the charge storage element 114 is sufficient to deliver the therapy during a period of 12 hours or less, during a period of 6 hours or less, during a period of 3 hour or less, during a period of 2 hour or less, during a period of 1 hour or less, during a period of 30 minutes or less, during a period of 15 minutes or less, during a period of 10 minutes or less, during a period of 5 minutes or less, during a period of 2 minutes or less, during a period of 1 minutes or less, during a period of 30 seconds or less, or even during a period of 15 seconds or less. In a particular embodiment, the charge storage element 114 stores enough charge to deliver only a single treatment. The single treatment may be a single electrical pulse, or a burst including a plurality of electrical pulses.

Thus, the implantable medical device 106 may be relatively small, since the large high capacity power storage requirement is alleviated. Further, the implantable medical device 106 may be provided power via far field radiative powering, which may increase patient compliance and mobility relative to near-field and/or inductive powering.

FIG. 2 is a block diagram of a second particular embodiment of a system 200 including a second embodiment of an implantable medical device 206. The implantable medical device 206 includes a number of elements in common with the implantable medical device 106 of FIG. 1. For example, in the embodiment illustrated in FIG. 2, the implantable medical device 206 includes the antenna and matching network 110, the voltage rectifier and voltage multiplier 112, the charge storage element 114 and the therapy delivery unit 116, each of which operates as explained with reference to FIG. 1

The implantable medical device 206 may include a DC-to-DC converter 118 coupled to the voltage rectifier, coupled to the voltage multiplier, or coupled to the rectifier/multiplier 112. In one instance, the DC-to-DC converter 118 can be a boost converter used to step-up the voltage. In a further instance, the DC-to-DC converter 118 can be a step-up regulator. The DC-to-DC converter 118 may be configured to receive output of the rectifier, the voltage multiplier, or the rectifier/multiplier 112 to which the DC-to-DC converter 118 is coupled.

The DC-to-DC converter 118 may have a relatively low input resistance and a relatively high output resistance, which may facilitate impedance matching between the antenna and other components of the implantable medical device 206, such as the charge storage element 114. For example, the resistance of the antenna may be relatively low (e.g., from a few ohms up to about 50 ohms). A matching network to match from this low resistance to a very high resistance (e.g., 1000 Ohms) may have large losses. The DC-to-DC converter 118 may bridge the gap between this resistance mismatch by providing a relatively low input resistance but high output resistance with high efficiency (e.g., about 90% or more). For example, the high output resistance may be greater than the low input resistance by at least 40 times, may be greater than the low input resistance by at least 20 times, may be greater than the low input resistance by at least 10 times, may be greater than the low input resistance by at least 6.25 times, may be greater than the low input resistance by at least 4 times, may be greater than the low input resistance by at least 3 times, or may be greater than the low input resistance by at least 2 times. In a particular embodiment, the high output resistance is approximately 666 KOhms and the low input resistance is approximately 107 KOhms.

The DC-to-DC converter 118 may improve efficiency of the implantable medical device 206 relative to a similar implantable medical device that does not include the DC-to-DC converter 118 (such as the implantable medical device 106 of FIG. 1). In particular, the DC-to-DC converter 118 may be used to generate sufficient voltage to bias other components of the implantable medical device 206 (e.g., CMOS circuits) with a relatively low input voltage requirement. For example, at least one of the voltage multiplier, the charge storage element 114, the therapy delivery unit 116, a control unit (such as a control unit 320 of FIG. 4), and the voltage rectifier may be a CMOS circuit, and the DC-to-DC converter 118 may be configured to generate voltages operative to bias the subsequent CMOS circuit or circuits.

FIG. 3 is a block diagram of a third particular embodiment of a system 300 including a third embodiment of an implantable medical device 306. The implantable medical device 306 includes a number of elements in common with the implantable medical device 206 of FIG. 2. For example, in the embodiment illustrated in FIG. 3, the implantable medical device 306 includes the antenna and matching network 110, the voltage rectifier and voltage multiplier 112, the DC-to-DC converter 118, the charge storage element 114 and the therapy delivery unit 116, each of which operates as explained with reference to FIGS. 1 and 2.

In the implantable medical device 306, the therapy delivery unit 116 is a signal generator 316. The signal generator 316 may be operative to be electrically coupled to one or more electrodes 318. The electrode(s) 318 may be configured to be positioned in proximity to, or attached to, the target tissue 130 of the patient to provide electrical stimulation to the target tissue 130. The electrodes(s) 318 may be coupled directly to the implantable medical device 106 (i.e., without leads) or may be coupled to the implantable medical device 106 via one or more leads (not shown).

In an illustrative example, the implantable medical device 306 may be directly coupled to electrode(s) 318. For example, the electrode(s) 318 may be proximity electrodes that are adapted to be implantable proximate to a portion of the target tissue 130. The implantable medical device 306 may be configured as or may be coupled to a nerve wrap 332 that includes or is coupled to the electrodes 318. For example, components of the implantable medical device 306 (e.g., the antenna and matching network 110, the voltage rectifier and voltage multiplier 112, the DC-to-DC converter 118, the charge storage element 114, the signal generator 316, other components, or a combination thereof) may be coupled to a flexible circuit board 334, which may be embedded within or coupled to the nerve wrap 332. The proximity electrodes may be provided on a portion of the nerve wrap 332 that is configured to make contact with the target tissue 130. For example, the proximity electrodes may be printed on or otherwise applied to a portion of the nerve wrap 332 or the flexible circuit board 334. In other embodiments, the implantable medical device 306 has a metal case (not shown) or another biologically compatible housing that at least partially contains components of the implantable medical device 306, such as the antenna and matching network 110, the voltage rectifier and voltage multiplier 112, the DC-to-DC converter 118, the charge storage element 114, the therapy delivery unit 116, the signal generator 316, other components, or a combination thereof. When the implantable medical device 306 has a metal case, the metal case may act as one of the electrodes 318.

The signal generator 316 may be adapted to apply electrical stimulation to the target tissue 130. For example, when the target tissue 130 is nerve tissue, the electrical stimulation may induce efferent action potentials, induce afferent action potentials, inhibit intrinsic action potentials, or a combination thereof. In another example, when the target tissue 130 is muscle tissue, the electrical stimulation may cause muscle contraction or may facilitate regulation of muscle contraction.

FIG. 4 is a block diagram of a fourth particular embodiment of a system 400 including a fourth embodiment of an implantable medical device 406. The implantable medical device 406 includes a number of elements in common with the implantable medical device 306 of FIG. 3. For example, in the embodiment illustrated in FIG. 4, the implantable medical device 406 includes the antenna and matching network 110, the voltage rectifier and voltage multiplier 112, the DC-to-DC converter 118, the charge storage element 114 and the signal generator 316, each of which operates as explained with reference to FIGS. 1-3. Although not specifically identified in FIG. 4, components of the implantable medical device 406 may be coupled to or formed on a flexible circuit board, such as the flexible circuit board 334 of FIG. 3. Additionally or in the alternative, the implantable medical device 406 may include, be coupled to or be embedded within a nerve wrap, such as the nerve wrap 332 of FIG. 3. Alternately, the implantable medical device 406 may have a case (not shown) formed of a metal or another biologically compatible material. Further, the implantable medical device 406 may include or be coupled to the electrodes 318, which operate as explained with reference to FIG. 3.

The implantable medical device 406 may include a control unit 320. The control unit 320 may be powered by the charge storage element 114. The control unit 320 may be operative to control delivery of the therapy by a therapy delivery unit, such as the therapy delivery unit 116 of FIGS. 1 and 2 or the signal generator 316 of FIGS. 3 and 4. For example, the control unit 320 may control parameters of therapeutic stimulation provided by the signal generator 316 to the target tissue 130. The parameters of the therapeutic stimulation may include a frequency of therapy delivery (i.e., a time period between treatments), a duty cycle of therapy delivery, a magnitude of therapy delivery (e.g., an amount of energy delivered to the target tissue 130 during a treatment, a magnitude of a voltage of an electrical signal used to deliver the therapy, a magnitude of a current of the electrical signal, or a combination thereof), and a mode of therapy delivery (e.g., a single pulse mode or a burst mode including a plurality of pulses). Other parameters may also be controlled by the control unit 320, such as a location treated when more than one target tissue 130 can be selected for treatment; whether the treatment includes electrical stimulation, delivery of a drug, other treatment, or a combination thereof; and whether electrical signals applied to the target tissue 130 induce efferent signals, induce afferent signals, bias the target tissue to near a firing threshold, inhibit intrinsic efferent or afferent signals, and so forth.

In a particular embodiment, the control unit 320 may cause the therapeutic stimulation to be applied to the target tissue 130 responsive to a sensed patient parameter (e.g., a condition, state or value associated with the body of the patient). For example, the control unit 320 may receive information via one or more of the electrodes 318 or from another sensor (not shown), and may control application of therapeutic stimulation based on the received information. Therapeutic stimulation that is based on or responsive to the sensed patient parameter may include "active," "responsive," "closed-loop," "feedback," or "triggered" stimulation.

In another embodiment, the control unit 320 may cause the therapeutic stimulation to be applied to the target tissue 130 without sensing or detecting a patient parameter. For example, the control unit 320 may cause the signal generator 316 to apply a series of electrical pulses to the target tissue 130 periodically, intermittently, or continuously throughout the day, or according to another predetermined schedule (e.g., a circadian schedule or another predetermined treatment cycle). This type of stimulation may include "passive," "periodic," "continuous," "open-loop," "non-feedback," or "prophylactic" stimulation.

In another embodiment, the control unit 320 may cause the therapeutic stimulation to be applied to the target tissue 130 responsive to the far field radiative signals 104 or wireless control signals. For example, the control unit 320 may cause the signal generator 316 to apply a series of electrical pulses to the target tissue 130 according to a predetermined schedule during or after receipt of the far field radiative signals 104 or wireless control signals. To illustrate, when the far field radiative signals 104 or wireless control signals are received, receipt of the far field radiative signals 104 or wireless control signals may cause the control unit 320 to initiate therapeutic stimulation without delay or according to a predetermined delay. This type of stimulation may be referred to as "externally controlled" stimulation. In the case that the far-field radiative signals 104 are used to wirelessly deliver power to the implantable medical device 406, the implantable medical device 406 may deliver therapy when a sufficient power supply is received.

In another embodiment, the control unit 320 may use a combination of active, passive and externally controlled stimulation. For example, in response to receipt of the far field radiative signals 104, the control unit 320 may initiate stimulation responsive to a sensed patient parameter (e.g., sensing one or more patient parameters and applying stimulation responsive to the one or more sensed patient parameters).

FIG. 5 is a block diagram of a fifth particular embodiment of a system 500 including a fifth embodiment of an implantable medical device 506. The implantable medical device 506 includes a number of elements in common with the implantable medical device 406 of FIG. 4. For example, in the embodiment illustrated in FIG. 5, the implantable medical device 506 includes the antenna and matching network 110, the voltage rectifier and voltage multiplier 112, the step-up regulator 118, the charge storage element 114, the signal generator 316, and the control unit 320, each of which operates as explained with reference to one or more of FIGS. 1-4. Although not specifically identified in FIG. 5, components of the implantable medical device 506 may be coupled to or formed on a flexible circuit board, such as the flexible circuit board 334 of FIG. 3. Additionally or in the alternative, the implantable medical device 506 may include, be coupled to or be embedded within a nerve wrap, such as the nerve wrap 332 of FIG. 3. Alternately, the implantable medical device 506 may have a case (not shown) formed of a metal or another biologically compatible material. Further, the implantable medical device 506 may include or be coupled to the electrodes 318, which operate as explained with reference to FIG. 3.

The implantable medical device 506 may include a threshold detector 322 coupled to the charge storage element 114. The threshold detector 322 may be configured to determine when charge stored at the charge storage element 114 satisfies a charge threshold. The threshold detector 322 may provide an indication to the control unit 320 when the charge threshold is satisfied. The control unit 320 may control delivery of the therapy by the therapy delivery unit (e.g., the signal generator 316) responsive to the indication from the threshold detector 322. For example, the control unit 320 may cause the signal generator 316 to deliver the therapy responsive to receiving an indication that the charge threshold is satisfied.

The charge threshold may be set based on a power requirement of the implantable medical device 506 to deliver the therapeutic stimulation. In a particular embodiment, the charge threshold may be set according to an amount of charge needed to deliver one treatment (i.e., a single dose or instance of therapeutic stimulation) to the target tissue 130. In a particular embodiment, the implantable medical device 506 has a power requirement of 100 microwatts or less to deliver one treatment (i.e., a single dose or instance of therapeutic stimulation). The implantable medical device 506 may have a power requirement of 50 microwatts or less, 20 microwatts or less, or 10 microwatts or less to deliver one treatment. The charge threshold may be satisfied when the charge storage element 114 has sufficient charge to meet the power requirement for a predetermined number of treatments (e.g., a single treatment).

In an embodiment, a duty cycle of the therapy may be controlled by a duty cycle of power delivery from the external power source (e.g., the far field transmitter 102). For example, the far field transmitter 102 may periodically or occasionally transfer power wirelessly to the implantable medical device 506 according to a duty cycle associated with the far field transmitter 102. At least a portion of the power may be stored by the charge storage element 114. The threshold detector 322 may determine when the charge storage element 114 has obtained sufficient charge to satisfy the charge threshold. In response to the charge threshold being satisfied, the control unit 320 may cause energy to be delivered through the therapy delivery unit 116 (or the signal generator 316) to deliver therapy to the target tissue 130.

In another embodiment, the charge threshold may be set according to an amount of charge needed to deliver more than one treatment, such as a number of treatments specified for a particular amount of time, such as at least 3 days, at least 1 day, at least 12 hours, at least 6 hours, at least 3 hours, at least 2 hours, at least 1 hour, at least 30 minutes, at least 15 minutes, at least 10 minutes, at least 5 minutes, at least 2 minutes, at least 1 minute, at least 30 seconds, at least 15 seconds, at least 10 seconds, or less than 10 seconds. In this embodiment, the implantable medical device 506 may include control logic, such as the control unit 320, that controls application of the therapy. For example, the control unit 320 may control parameters of the therapy such as timing, duty cycle, current amplitude, voltage amplitude, and frequency of signals applied to the target tissue 130.

In a particular embodiment, the control unit 320 may be programmable while the implantable medical device 506 is implanted in a patient. For example, the implantable medical device 506 may include a receiver 530 coupled to the antenna. The receiver 530 may also be coupled to the control unit 320, the threshold detector 322, or both. The receiver 530 may be configured to receive therapy parameter data from an external source. For example, the therapy parameter data may be received via modulation of the far field radiative signals 104 from the far field transmitter 102. The therapy parameter data may specify parameters of the therapy to be delivered to the patient. The receiver 530 may provide the received therapy parameter data to the control unit 320 or to the threshold detector 322 to program the parameters of the therapy to be delivered to the patient. The therapy parameter data may specify, for example, a frequency of therapy delivery, a duty cycle of therapy delivery, a magnitude of therapy delivery, a mode of therapy delivery, or a combination thereof. Available modes of therapy delivery may include a single pulse mode and a burst mode. In the burst mode, the therapy is delivered via one or more bursts, where each burst includes a plurality of pulses. Alternately or in addition, the therapy parameter data may specify a charge threshold to be applied by the threshold detector. For example, to modify an amount of energy to be applied by the signal generator 316 to the target tissue 130 during a single treatment, the charge threshold may be modified such that the modified charge threshold is satisfied when the charge storage element 114 stores sufficient charge to provide the single treatment.

In a particular embodiment, the implantable medical device 506 may use backscatter to transmit data to the far field transmitter 102 or another device. For example, the implantable medical device 506 may modulate backscattered energy in a manner that may be detected by a device external to the patient, such as the far field transmitter 102.

In a particular embodiment, such as when the far field transmitter 102 continuously provides power to the implantable medical device 506, third order backscatter may be used to send information from the implantable medical device 506 to an external device. For third order backscatter, nonlinear components of the implantable medical device 506 may be used to generate a third order frequency harmonic component when exposed to energy of a particular frequency. For example, one or more diodes may be used as non-linear components. In this example, the diodes may be separate components or diodes of the voltage rectifier/multiplier 112 may be used to generate the third order frequency harmonic component. The third order frequency harmonic components may be modulated or enhanced to enable generation of a frequency component that is far removed from a fundamental frequency of the far field radiative signal 104. For example, a high-Q resonant circuit which is resonant around the third order frequency can be used to enhance the generation of this third order frequency harmonic component from the non-linear component. In another implementation, a high-frequency/radio-frequency amplifier, that maybe narrowband around the third order frequency harmonic component, can be used alone or in conjunction with the tuned high-Q resonant circuit, to enhance and amplify the third order frequency harmonic component. Thus, an external receiver (of the far field transmitter 102 or of another device external to the patient) may be able to tune to the third order frequency component without being saturated by the fundamental frequency, because the third order frequency component is sufficiently removed from the fundamental frequency so that power transmission and data transmission can occur at the same time (e.g., without time division duplexing the power transmission and data transmission). Because nonlinear components of the implantable medical device 506 naturally generate third order harmonics, modulation of such components to send information from the implantable medical device 506 to the external device may use little or no additional power.

Figure 6:
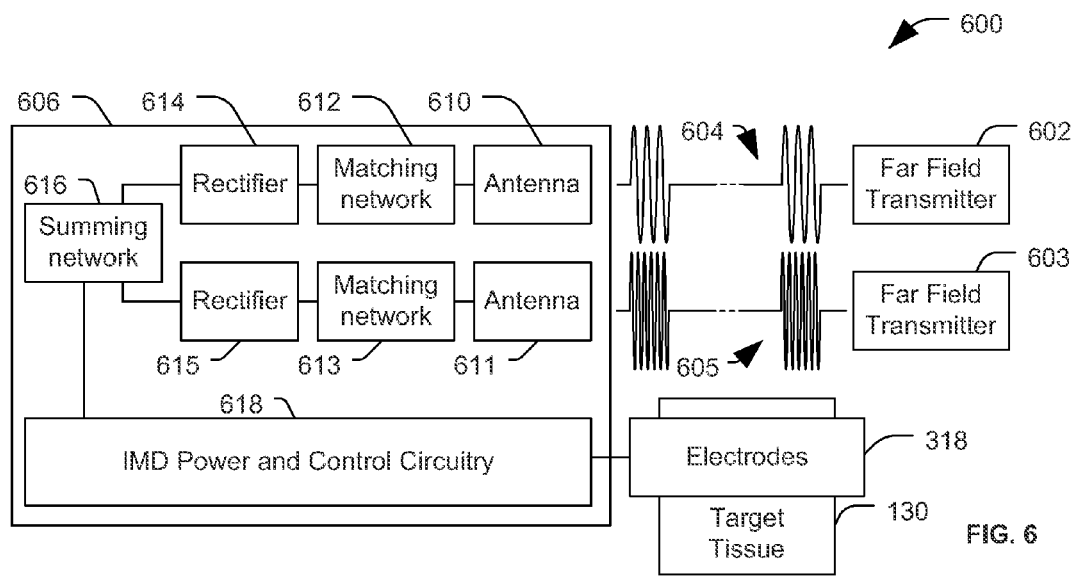
FIG. 6 is a block diagram of a sixth particular embodiment of a system including an implantable medical device and a far field transmitter.
Figure 7:
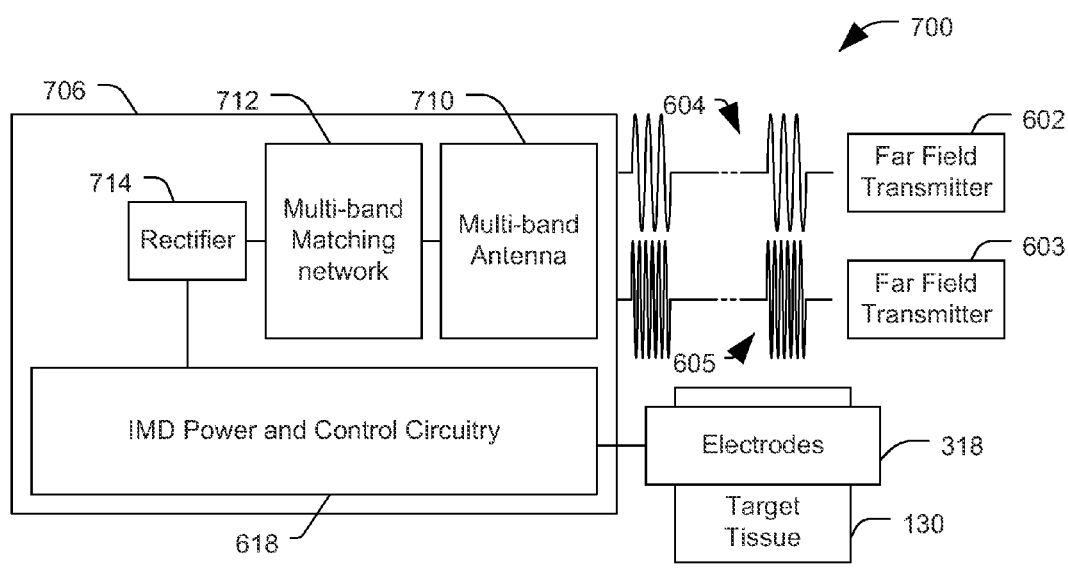
FIG. 7 is a block diagram of a seventh particular embodiment of a system including an implantable medical device and a far field transmitter.

FIGS. 6 and 7 illustrate embodiments in which an implantable medical device is supplied with at least a portion of its operating power simultaneously or concurrently from two or more far field transmitters. For example, a first far field transmitter 602 may provide power to the implantable medical device via first far field radiative signals 604 in a first frequency band, and a second far field transmitter 603 may simultaneously or concurrently provide power to the implantable medical device via second far field radiative signals 605 in a second frequency band.

Referring to FIG. 6, a block diagram of a sixth particular embodiment of a system 600 including a sixth embodiment of an implantable medical device 606 is shown. The implantable medical device 606 includes multiple antennas, including a first antenna 610, a second antenna 611, and possibly one or more additional antennas (not shown). The implantable medical device 606 may also include one or more matching networks associated with one or more of the antennas, such as a first matching network 612 associated with the first antenna 610, a second matching network 613 associated with the second antenna 611, and possibly one or more additional matching networks (not shown) associated with other antennas (not shown).

In a particular embodiment, each antenna 610, 611 and/or each matching network 612, 613 may be configured or tuned to operate at a particular frequency or frequency band. For example, the first antenna 610 and/or the first matching network 612 may be configured or tuned to receive far field radiative signals in a first frequency band that includes a frequency of the first far field radiative signals 604. The second antenna 611 and/or the second matching network 613 may be configured or tuned to receive far field radiative signals in a second frequency band that includes a frequency of the second far field radiative signals 605. For example, the first and second frequency bands may be centered at one of approximately 433 MHz and 900 MHz, respectively, approximately 433 MHz and 2.4 GHz, respectively, approximately 433 MHz and 5.8 GHz, respectively, approximately 900 MHz and 2.4 GHz, respectively, approximately 900 MHz and 5.8 GHz, respectively, and approximately 2.4 GHz and 5.8 GHz, respectively. The first far field radiative signals 604 and the second far field radiative signals 605 may include at least a portion of the signals that are transmitted concurrently, or may be transmitted in an interleaved fashion. When other antennas or matching networks are present, these may be configured or tuned to receive far field radiative signals in the first frequency band, in the second frequency band, in another first frequency band, or in a combination thereof. Thus, when exposure limits or other radiofrequency transmission limitations (e.g., FCC and/or FDA regulations) limit transmission power at a particular frequency, more than one frequency may be used for far field radiative power transfer.

The implantable medical device 606 may also include one or more rectifiers. Each rectifier may be associated with a particular antenna. For example, a first rectifier 614 may be associate with the first antenna 610 and the first matching network 612, a second rectifier 615 may be associate with the second antenna 611 and the second matching network 613, and possibly one or more additional rectifiers (not shown) may be associate with other antennas and matching networks (not shown). In another configuration, one rectifier, such as the first rectifier 614, may be associated with multiple antennas. For example, the first rectifier 614 may be coupled to a set of antenna (of which the first antenna 610 is a representative antenna) that are each configured or tuned to receive the first far field radiative signals 604, and the second rectifier 615 may be coupled to a set of antenna (of which the second antenna 611 is a representative antenna) that are each configured or tuned to receive the second far field radiative signals 605.

When the implantable medical device 606 includes multiple rectifiers, such as the first rectifier 614 and the second rectifier 615, the rectifiers 614, 615 may be coupled to a summing network 616. The summing network 616 may combine the direct current (DC) output of the rectifiers 614, 615 and provide the combined DC output to other power and/or control circuitry, represented in FIG. 6 as implantable medical device (IMD) power and control circuitry 618.

The IMD power and control circuitry 618 may include any combination of power modification, power storage, IMD control, therapy and sensing circuitry as described above with reference to FIGS. 1-5 or as described subsequently with reference to FIGS. 7 and 8. For example, the IMD power and control circuitry 618 may include a voltage multiplier (or the rectifiers may be rectifier/multiplier units as described with reference to FIGS. 1-5), a DC-to-DC converter (such as the DC-to-DC converter 118 of FIGS. 2-5), a charge storage element (such as the charge storage element 114 of FIGS. 1-5), a therapy delivery unit (such as the therapy delivery unit 116 of FIGS. 1 and 2), a signal generator (such as the signal generator 316 of FIGS. 3-5), a control unit (such as the control unit 320 of FIGS. 4 and 5), a threshold detector (such as the threshold detector 322 of FIG. 5), sensor circuitry (such as sensor circuitry 816 of FIG. 8), other components, or a combination thereof. Although not specifically identified in FIG. 6, components of the implantable medical device 606 may be coupled to or formed on a flexible circuit board, such as the flexible circuit board 334 of FIG. 3. Additionally or in the alternative, the implantable medical device 606 may include, be coupled to or be embedded within a nerve wrap, such as the nerve wrap 332 of FIG. 3. Alternately, the implantable medical device 606 may have a case (not shown) formed of a metal or another biologically compatible material. Further, the implantable medical device 606 may include or be coupled to the electrodes 318, which operate as explained with reference to FIG. 3.

The implantable medical device 606 may also include one or more receivers (not shown in FIG. 6), such as the receiver 530 of FIG. 5. For example, the implantable medical device 606 may include a single receiver coupled to one or more of the antennas 610, 611. To illustrate, a first receiver may be coupled to the first antenna 610, or the first receiver may be coupled to the first antenna 610, to the second antenna 611, and possibly to one or more additional antennas, when additional antennas are present. In this illustrative example, the first receiver may be a multiband receiver capable of receiving data transmitted in several frequency bands. Alternately, the first receiver may be tunable such that the first receiver can receive data via one frequency band at a time and can be adjusted or tuned (e.g., by a control unit) to select a particular frequency band. In another example, the implantable medical device 606 may include multiple receivers. To illustrate, a first receiver may be coupled to the first antenna 610 and a second receiver may be coupled to the second antenna 611. In this illustrative example, the first receiver may be configured to or tuned to receive data via a first frequency band corresponding to the frequency of the first far field radiative signals 604, and a second receiver may be configured to or tuned to receive data via a second frequency band corresponding to the frequency of the second far field radiative signals 605.

Referring to FIG. 7, a block diagram of a seventh particular embodiment of a system 700 including a seventh embodiment of an implantable medical device 706 is shown. The implantable medical device 706 includes one or more multi-band antennas, such as a multi-band antenna 710. The implantable medical device 706 may also include one or more multi-band matching networks with the multi-band antennas 712, such as a multi-band matching network 712. The multi-band antenna 710 and/or the multi-band matching network 712 may be configured or tuned to operate at multiple frequencies or frequency bands. For example, the multi-band antenna 710 and/or the multi-band matching network 712 may be configured or tuned to receive far field radiative signals in a first frequency band that includes the frequency of the first far field radiative signals 604 and in a second frequency band that includes the frequency of the second far field radiative signals 605. For example, the first and second frequency bands may be centered at one of approximately 433 MHz and 900 MHz, respectively, approximately 433 MHz and 2.4 GHz, respectively, approximately 433 MHz and 5.8 GHz, respectively, approximately 900 MHz and 2.4 GHz, respectively, approximately 900 MHz and 5.8 GHz, respectively, and approximately 2.4 GHz and 5.8 GHz, respectively. The first far field radiative signals 604 and the second far field radiative signals 605 may include at least a portion of the signals that are transmitted concurrently, or may be transmitted in an interleaved fashion. Thus, when exposure limits or other radiofrequency transmission limitations (e.g., FCC regulations) limit transmission power at a particular frequency, more than one frequency may be used for far field radiative power transfer.

The implantable medical device 706 may also include one or more rectifiers, such as a rectifier 714 coupled to the multi-band antenna 710 and the multi-band matching network 712. Direct current (DC) output of the rectifier 714 may be provided to the implantable medical device (IMD) power and control circuitry 618. As explained above, the IMD power and control circuitry 618 may include any combination of power modification, power storage, IMD control, therapy and sensing circuitry as described above with reference to FIGS. 1-6 or as described subsequently with reference to FIG. 8. The implantable medical device 706 may include, be coupled to or be embedded within a nerve wrap, such as the nerve wrap 332 of FIG. 3. Alternately, the implantable medical device 706 may have a case (not shown) formed of a metal or another biologically compatible material. Further, the implantable medical device 706 may include or be coupled to the electrodes 318, which operate as explained with reference to FIG. 3.

The implantable medical device 706 may also include one or more receivers (not shown in FIG. 7), such as the receiver 530 of FIG. 5. For example, the implantable medical device 706 may include a multi-band receiver capable of receiving data transmitted in several frequency bands coupled to the multi-band antenna 710. Alternately, the receiver may be tunable such that the receiver can receive data via one frequency band at a time and can be adjusted or tuned (e.g., by a control unit) to select a particular frequency band. In another example, the implantable medical device 706 may include multiple receivers. To illustrate, a first receiver and a second receiver may be coupled to the multi-band antenna 710. The first receiver may be configured to or tuned to receive data via a first frequency band corresponding to the frequency of the first far field radiative signals 604, and a second receiver may be configured to or tuned to receive data via a second frequency band corresponding to the frequency of the second far field radiative signals 605.

Thus, the implantable medical devices 606 and 706 are capable of receiving far field radiative signals from multiple far field transmitters 602, 604. The far field radiative signals 604, 065 may be in the same frequency band, in different bands, or in overlapping frequency bands. Using multiple antennas may enable increased power reception. Using multiple frequency bands may enable increased power transfer. For example, providing antennas configured to receive two or more different frequency bands may allow an increase in overall transmission power to the implantable medical devices 606, 706 since a transmission power restriction may apply to each band separately. To illustrate, when each frequency band is limited to 1 watt of transmission power, two frequency bands may be used to transmit approximately 2 watts of power.

FIG. 8 is a block diagram of an eighth particular embodiment of a system 800 including an implantable medical device 806 and one or more far field transmitter 802. The far field transmitters 802 and antenna(s) 810 may include any combination of transmitters and antennas described above with reference to FIGS. 1-7. For example, a single far field transmitter and a single antenna may be used. In another example, multiple far field transmitters may be used with a single antenna. In yet another example, multiple far field transmitters may be used with a multiple antennas. In still another example, a single far field transmitter may be used with a multiple antennas. The antenna(s) 810 may be coupled to or may include one or more matching networks (not shown). Additionally, the antenna(s) 810 may be coupled to one or more rectifiers 814 that provide a DC output to the IMD power and control circuitry 618.

The implantable medical device 806 also includes sensor circuitry 816. The sensing circuitry 816 may be powered by a charge storage element of the IMD power and control circuitry 618. The sensor circuitry 816 may be configured to receive a stimulus and to generate a digital or analog output corresponding to the stimulus. The stimulus may be electrical, optical, magnetic, chemical or physical. For example, the stimulus may correspond to or be indicative of presence or concentration of a chemical, such as a chemical that occurs naturally within a patient's body (e.g., a neurotransmitter, a hormone, blood oxygen, a metabolic product, etc.) or a foreign chemical (e.g., a medication). In another example, the stimulus may correspond to or be indicative of presence or other characteristics of an electrical signal, such as a naturally occurring electrical signal (e.g., an endogenous action potential) or an induced electrical signal (e.g., an induced action potential). In yet another example, the stimulus may correspond to or be indicative of presence or other characteristics of a physical function or parameter, such as a movement of the body or a portion of the body, respiratory rate, pulse rate, blood pressure, body temperature, etc.

The output of the sensor circuitry 816 may be provided to the IMD power and control circuitry 618. The IMD power and control circuitry 618 may use the output as feedback related to a therapy provided by the implantable medical device 806. For example, when the implantable medical device 806 applies stimulation or another therapy to the target tissue 130, electrodes 818 may be used to detect the stimulus or a body response to the stimulus and to send information to the sensor circuitry 816. The sensor circuitry 816 may send the output to the IMD power and control circuitry 618, and the IMD power and control circuitry 618 may adjust the stimulation or other therapy based on a value of the output.

In a particular embodiment, information descriptive of the output of the sensor circuitry 816, such as a logical or numeric value, may be transmitted by the implantable medical device 806 to an external device. For example, the IMD power and control circuitry 618 may process the output of the sensor circuitry 816 to determine information that is to be transmitted to the external device. One or more non-linear components of the IMD power and control circuitry 618 may be used to modulate backscatter of the far field radiative signals 804 to transmit the information to the external device, as described with reference to FIG. 5.

In a particular embodiment, the implantable medical device 806 does not include a therapy delivery unit and is only used to gather and transmit sensed data from the patient's body. Thus, the far field radiative signals 802 may be used to power an implantable medical device that is a sensor or is primarily used as a sensor.

In addition to the specific embodiments illustrated in FIGS. 1-8, other embodiments and variations are envisioned. For example, components of any of the implantable medical devices 106, 206, 306, 406, 506, 606, 706, and 806 may be coupled to or formed on a flexible circuit board, such as the flexible circuit board 334 of FIG. 3. To illustrate, one or more antennas, one or more matching networks, one or more voltage multipliers, one or more rectifiers, one or more DC-to-DC converters, one or more charge storage elements, one or more therapy delivery units, one or more control units, one or more signal generators, one or more receivers, one or more threshold detector, sensor circuitry, or a combination thereof, may be integrated on the flexible circuit board 334.

Additionally or in the alternative, any of the implantable medical devices 106, 206, 306, 406, 506, 606, 706, and 806 may include, be coupled to or be embedded or housed within an enclosure 532 of FIG. 5. The enclosure 532 may be flexible, such as the nerve wrap 332 of FIG. 3, or may be a substantially rigid, hermetically sealed case. The enclosure 532 may house or partially house one or more of the other components, such as one or more antennas, one or more matching networks, one or more receivers, one or more rectifiers, one or more voltage multipliers, one or more DC-to-DC converters, one or more charge storage elements, one or more threshold detectors, one or more control units, one or more signal generators, one or more therapy delivery units, sensor circuitry, or a combination thereof. To improve power transfer to the implantable medical device 106, 206, 306, 406, 506, 606, 706, or 806, the enclosure 532 may be formed at least partially of a radiofrequency (RF) transparent material. The RF transparent material may be selected to not attenuate or degrade high-frequency signals, such as the far field radiative signals 104. Further, the RF transparent material may be selected to be biocompatible and hermetically sealable. Examples of suitable materials include ceramics (such as, low-temperature co-fired ceramic (LTCC), alumina, etc.), liquid crystal polymers, polyimides, plastics, and polyether-based thermoplastic polyurethanes (TPU) (e.g., Tecothane® TPU).

In a particular embodiment, the enclosure 532 may be formed of a material that has a permittivity value that results in a small, reduced or minimal impedance boundary reflection loss between the enclosure 532 and a tissue layer of the patient. In a particular embodiment, the enclosure 532 may be formed of a material that is selected such that, as a whole, electric properties of the material (e.g., conductivity, permittivity, permeability) reduce or minimize total power losses due to all effects, including attenuation, dielectric/impedance boundary reflections, dielectric resonance, eddy currents, and so forth.

In a particular embodiment, dimensions of the enclosure 532 (e.g., length, width, and/or thickness) may be selected to provide efficient power transfer. For example, the dimensions of the enclosure 532 may be selected to enable use of an efficient antenna design. To illustrate, the enclosure 532 may have a length or area of at least one side that is selected to be coupled to or to house an antenna with a length or area that enables acceptable antenna gain while maintaining flexibility for placement of the implantable medical device 106, 206, 306, 406, 506, 606, 706, 806.

An implantation location of the implantable medical device 106, 206, 306, 406, 506, 606, 706, 806 may be selected based at least in part on providing efficient power transfer. For example, a shallower implantation depth may result in less tissue absorption based attenuation, thereby providing improved energy transfer efficiency relative to a deeper implantation depth. Dielectric properties of specific tissues that will surround the implantable medical device 106, 206, 306, 406, 506, 606, 706, 806 may also be considered. For example, higher permittivity of the specific tissues may result in higher gains for electrically-small antennas but greater tissue absorption of the electromagnetic waves, and lower conductivity may result in less tissue absorption of the electromagnetic waves.

In addition to being designed for efficient power transfer, the implantable medical device 106, 206, 306, 406, 506, 606, 706, 806 may be designed to reduce power consumed to provide therapy. For example, parameters of the therapy may also be controlled (e.g., by the control unit 320) or configured to reduce power consumption. To illustrate, a strength duration curve of nerve fibers to be stimulated may be consider to enable reduced power consumption. The strength duration curve is a relationship between current and pulse width of a therapeutic signal. When applying stimulation to a nerve fiber using the therapeutic signal, as the duration of stimulus decreases, the applied current has to increase to bring the nerve fiber to a threshold potential. The current and pulse width of the therapeutic signal may be selected to efficiently provide energy to the nerve fiber.

The implantable medical device 106, 206, 306, 406, 506, 606, 706, 806 may also or in the alternative reduce power consumption by taking a circadian rhythm of the patient into account. For example, the implantable medical device 106, 206, 306, 406, 506, 606, 706, 806 may provide more frequent, higher duty cycle, higher frequency, and/or higher amplitude stimulations at times when the patient is most likely to have a seizure and a less intense, less frequent, and/or lower power consumption stimulation when the patient is less likely to have a seizure (e.g., based on personal history of the patient).

In another example, the implantable medical device 106, 206, 306, 406, 506, 606, 706, 806 may provide stimulation responsive to a sensed value. For example, a sensor (such as the sensor circuitry 816 or another sensor) may detect a patient parameter associated with the patient and may provide a sensed value to the implantable medical device 106, 206, 306, 406, 506, 606, 706, 806, either directly or via the far field transmitter 102. The patient parameter may include, for example, a parameter associated with a seizure, such as a cardiac-based seizure response, a nerve action potential, or an EEG-based seizure response. Other values may also, or in the alternative, be sensed and stimulation may be provided responsive to the sensed value or values.

In another example, circuits or firmware may be selected or configured to improve efficiency of the implantable medical device 106, 206, 306, 406, 506, 606, 706, 806. To illustrate, the control unit 320 may include a microcontroller. The microcontroller may use a reduced power mode, such as a sleep mode, to reduce power consumption by the control unit 320. For example, the microcontroller may be put in a sleep mode while stimulation is applied to the target tissue 130. To illustrate, the microcontroller may awake (i.e., exit the sleep mode) to initiate application of the stimulation, then return to the sleep mode. The microcontroller may again awake at an end of a stimulation period to end application of the stimulation. As a more specific illustrative example, the threshold detector 322 may be operable to detect an initiate threshold and a cease threshold. The initiate threshold may be satisfied when the charge storage element 114 stores sufficient charge to deliver treatment. The cease threshold corresponds to an amount of power that is sufficient to operate one or more components of the implantable medical device until a next time that power is expected to be received from the far field transmitter. For example, the cease threshold may be set to allow continued operation of one or more sensors or the receiver 530 between on times of the far field radiative signals 104. The cease threshold may be satisfied when charge stored by the charge storage element 114 decreases by a predetermined amount from the initiate threshold or to a predetermined value. In this illustrative example, the microcontroller may awake and initiate application of the stimulation responsive to the threshold detector 322 indicating that the initiate threshold is satisfied. The microcontroller may then sleep until the threshold detector 322 indicates that the cease threshold is satisfied, at which time the microcontroller may awake to end application of the stimulation.

Although only one implantable medical device is shown in each of FIGS. 1-9, a far field transmitter may be used to provide power to more than one implantable medical device at a time. For example, a patient may have two or more implantable medical devices that receive at least a portion of their operating power from the far field transmitter. With inductive power coupling, as opposed to far field radiative power transfer, power coupling is targeted to a relatively small area. Accordingly, it may be difficult or impossible to use inductive coupling to provide power to implantable medical devices at different locations of a patient's body (e.g., one proximate a left vagus nerve and one proximate a right vagus nerve) with a single external inductive powering unit. However, using far field radiative signals enables providing power to such implantable medical devices using a single far field transmitter even though the implantable medical devices are remotely located from one another.

Additionally or in the alternative, a single implantable medical device 106, 206, 306, 406, 506, 606, 706, 806 (and possibly one or more other implantable medical devices) may be supplied with at least a portion of its operating power from two or more far field transmitters 102. For example, a first far field transmitter may supply power to the implantable medical device 106, 206, 306, 406, 506, 606, 706, 806 when the patient is at a first location (e.g., a first room of the patient's home) and a second far field transmitter may supply power to the implantable medical device 106, 206, 306, 406, 506, 606, 706, 806 when the patient is at a second location (e.g., in a second room of the patient's home).

Efficiency of the power transfer may also be improved by designing or tuning the antenna using an accurate 3D high-frequency electromagnetic model and an accurate human RF phantom. For example, a trial-and-error type procedure in which multiple different antenna types and geometries are tested (e.g., a simulation using an optimization search heuristic with the 3D high-frequency electromagnetic model and the human RF phantom) may be used to select a suitable antenna design. Additionally, simulation or physical testing may be used to tune the antenna. For example, resonance frequency seeking may be used to tune a resonant frequency of the antenna to provide efficient power transfer. Further, the antenna and matching network may be actively or passively tuned to provide efficient power transfer. To illustrate, the antenna may be tuned using a varactor that is arranged to change an effective electrical length of the antenna. In another example, a varactor, one or more inductors, one or more capacitors, or a combination thereof may use to tune the matching network.

FIG. 9 is a diagram illustrating a particular embodiment of a system 900 for powering an implantable medical device 906 using a far field transmitter 902. The implantable medical device 906 may correspond to one of the implantable medical devices 106, 206, 306, 406, 506, 606, 706 and 806 of FIGS. 1-8 or one of the additional embodiments or variants explained above. FIG. 9 illustrates particular features of far field radiative signals 904. The far field radiative signals 904 may correspond to one or more of the far field radiative signals 104, 604, 605, and 804 of FIGS. 1-8.

As illustrated in FIG. 9, and as described above, a distance, d, 916 between the far field transmitter 902 and an antenna 908 of the implantable medical device 906 may be greater than twice a wavelength, $\lambda$, 918 of the far field radiative signals 904. In the embodiment illustrated in FIG. 9, the far field radiative signals 904 are pulsed. That is, the far field radiative signals 904 have on-times 910 during which electromagnetic waves are generated, and off-times 914 during which no electromagnetic waves are generated. During a particular on-time 910, a burst 912 of energy may be transmitted. As used herein, the frequency of the far field radiative signals 904 refers to a frequency of electromagnetic waves of the burst 912. Relative timing of the on-times 910 and off-times 914 is referred to herein with reference to a duty cycle of the far field radiative signals 904. The pulsed far field radiative signals 904 may have an average transmission power of 1 watt or less. The pulsed far field radiative signals 904 may have a duty cycle of 10% or less, 5% or less, 2% or less, 1% or less, 0.5% or less, 0.266% or less, or 0.2% or less. Each burst 912 of the pulsed far field radiative signals 904 may deliver 100 milliwatts or less of power at the antenna 908. For example, each burst 912 may deliver 50 milliwatts or less, 30 milliwatts or less, 20 milliwatts or less, 10 milliwatts or less, 5 milliwatts or less, or 1 milliwatt or less of power at the antenna 908. During operation, an average input power at the antenna 908 may be 53 microwatts or less and the implantable medical device 906 may have a power conversion efficiency of 11.3 percent or less.

Increasing the power of the far field radiative signals 904 may boost the output voltage, current, and overall efficiency of energy transfer to the implantable medical device 906; however, transmission power at RF frequencies through human tissue is constrained by the exposure limit guidelines for time-varying electromagnetic fields. Pulsing the far field radiative signals 904, as explained above, may achieve a high output voltage and increase the efficiency of components of the implantable medical device 906, such as a voltage rectifier of the implantable medical device 906, while still maintaining a low average power to meet exposure limits, such as the Institute of Electrical and Electronics Engineers (IEEE) C95.1 SAR limits. This pulsing technique may take advantage of a nonlinear increase in voltage rectifier efficiency as relatively large instantaneous powers are used. A width and a frequency of the bursts 912 along with the instantaneous RF power may be selected or adjusted to efficiently and rapidly charge up a charge storage element, such as the charge storage element 114 of FIGS. 1-5 or a charge storage element of the IMD power and control circuitry 618 of FIGS. 6-8. In certain embodiments, one or more components of the implantable medical device 906, such as one or more of a voltage multiplier, a voltage rectifier, a charge storage element, a therapy delivery unit, and a signal generator, is a complementary metal-oxide-semiconductor (CMOS) circuit. In these embodiments, a boost converter or step-up regulator may be configured to generate voltages sufficient to operatively bias the CMOS circuits. For example, a short duty cycle of the far field radiative signals 904, e.g., about 2%, using the pulsed powering technique may enable a CMOS voltage rectifier to generate a sufficient bias with only an average transmit power of 300 mW.

Figure 10:
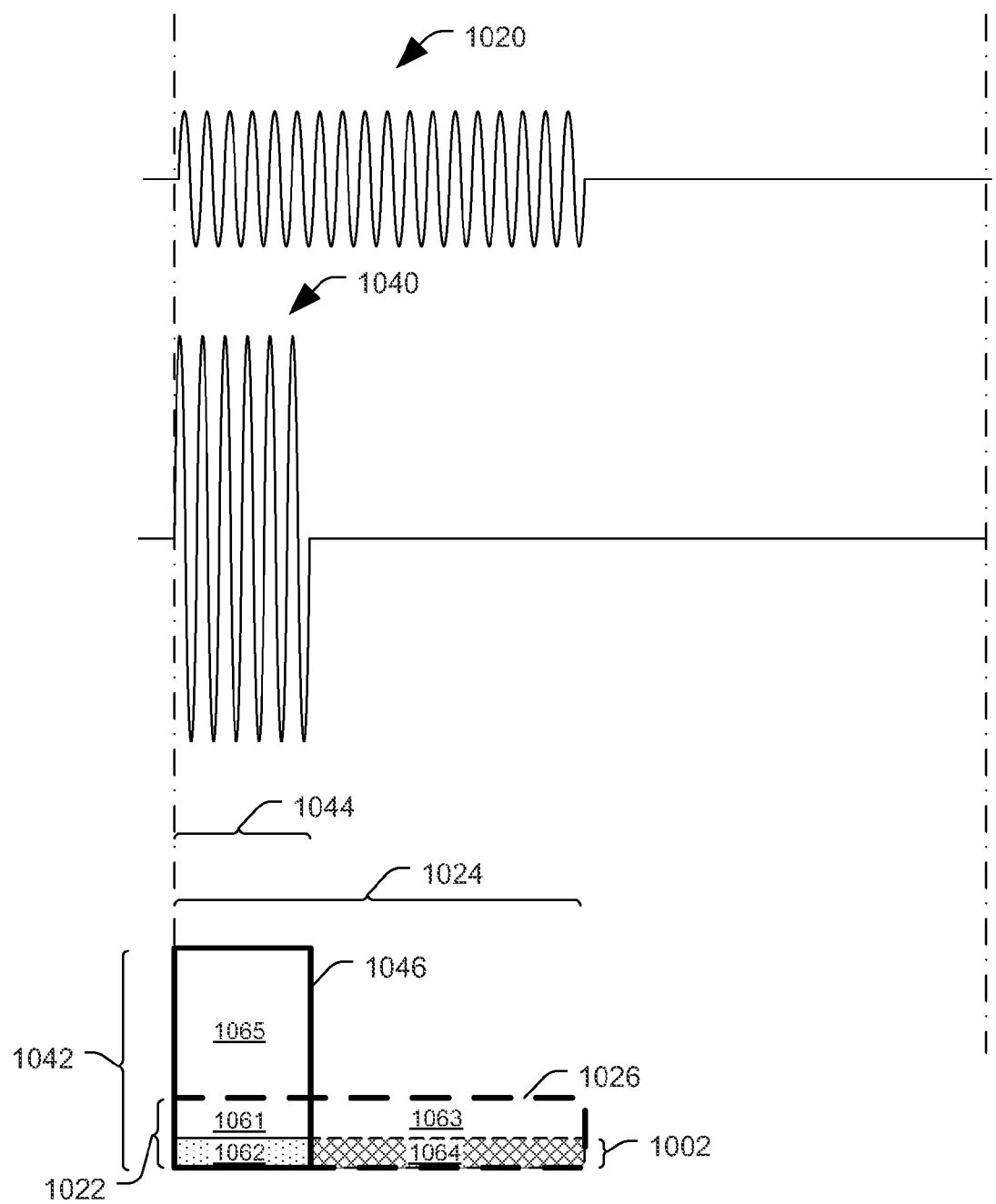
FIG. 10 is a diagram illustrating energy transfer using far field radiative signals with different amplitudes and on-times.

FIG. 10 is a diagram illustrating energy transfer using far field radiative signals with different amplitudes and on-times. In particular, FIG. 10 illustrates a relationship between energy transfer efficiency and a duty cycle of the far field radiative signals. FIG. 10 shows that energy transfer efficiency (and corresponding energy storage efficiency by an implantable medical device) can be improved by using relative high power, short duration transmissions (e.g., short duty cycle), as opposed to lower power, longer duration transmissions (e.g., longer duty cycle).

Two pulses are shown in FIG. 10, including a first pulse 1020 and a second pulse 1040. Each of the pulses 1020 and 1040 represent a far field radiative signal, such as one of the far field radiative signals 104 of FIGS. 1-5, the far field radiative signals 604, 605 of FIGS. 6-7, the far field radiative signals 804 of FIG. 8, or the far field radiative signals 904 of FIG. 9. For purposes of description of FIG. 10, it is assumed that the first pulse 1020 transmits the same total power as the second pulse 1040, and differences in efficiency of reception of the pulses 1020, 1040 are not considered. Thus, the first pulse 1020 provides power that is graphically illustrated by a first area 1026 (enclosed by bold dashed box in FIG. 10, which includes a first portion 1061, a second portion 1062, a third portion 1063 and a fourth portion 1064). Similarly, the second pulse 1040 provides power graphically illustrated by a second area 1046 (enclosed by bold box 1046 in FIG. 10, which includes the first portion 1061, the second portion 1062 and a fifth portion 1065). (Note that in FIG. 10, the power provided by the first pulse 1020 and the power provided by the second pulse 1040 are illustrated overlapping and intersecting one another merely to highlight differences between them. The portions 1061-1065 are used merely for convenience to clarify which portions of FIG. 10 are associated with each pulse 1020, 1040 and do not necessarily correspond to distinct phenomena).

An instantaneous power 1022 of the first pulse 1020 is smaller than an instantaneous power 1042 of the second pulse 1040. Thus, the first pulse 1020 has a longer on-time 1024 than an on-time 1044 of the second pulse 1040 in order to transfer the same amount of energy. That is, a far field radiative signal that uses the first pulse 1020 has a higher duty cycle that a far field radiative signal that uses the second pulse 1040 to transfer the power.

Forward biasing components of the implantable medical device (such as Schottky diodes of a rectifier) requires a threshold voltage and consumes a portion of the voltage, and thus power, transferred to the implantable medical device. For example, while the components are forward biased, instantaneous forward bias power 1002 may be used to provide the forward biasing, and is therefore not available to be stored or used for other purposes. When the second pulse 1040 is used, providing the threshold voltage to forward bias the components may use forward bias power corresponding to the second portion 1062; whereas, when the first pulse 1020 is used, providing the threshold voltage to forward bias the components may use forward bias power corresponding to a sum of the second portion 1062 and the fourth portion 1064. Decreasing the amount of time over which power is received (by using the second pulse 1040 rather than the first pulse 1020) causes the components of the implantable medical device to be forward biased for a shorter time, which provides power savings. Additionally, the instantaneous forward bias power 1002 is a larger percentage of the instantaneous power 1022 of the first pulse 1020 than it is of the instantaneous power 1042 of the second pulse 1040. That is, a larger percentage of the power derived from the first pulse 1020 is used to forward bias the components of the implantable medical device than the percentage of the power derived from the second pulse 1040 that is used to forward bias the components of the implantable medical device. Accordingly, using the second pulse 1040 causes less total power to be consumed for forward biasing components of the implantable medical device. For example, if the power represented in the first area 1026 and the power represented in the second area 1046 are approximately equivalent, then the power gained for storage and use at the implantable medical device by using the second pulse 1040 instead of the first pulse 1020 is approximately equal to the area of the second portion 1062.

Additionally, Shottky diodes are non-linear components that operate more efficiently the further they are forward biased. The non-linear characteristics of Shottky diodes can be described by a relationship of current to forward bias:

$$I \approx I_0 \cdot e^{V_F/(nV_T)}$$

Where I is current that the diode can pass (diode current), $I_0$ is reverse bias saturation current, n is a number that depends on a substrate of the Shottky diodes (e.g., about 1-2 for silicon) and $V_T$ is thermal voltage which is about 26 mV for room temperature, $V_F$ is the forward bias voltage. Thus, as the forward bias voltage, $V_F$, increases, the current that the diode can pass, I, increases exponentially. Considering Ohm's Law, V=IR, or R=V/I, as the voltage increase linearly, the resistance/impedance will decrease exponentially. Thus, the rectifier/multiplier circuit will "impede" the current/power flowing through it less as the forward bias voltage is increased. Stated another way, the diodes behave more like shorts as the forward bias voltage increases, thereby increasing the overall energy efficiency of the diodes.

Thus, for a particular energy transfer rate, a shorter duty cycle of the far field radiative signals may more efficiently provide power for use and/or storage by the implantable medical device. For example, based on the analysis presented in FIG. 10, and based on in vivo tests that were performed using an ocular implant in an animal subject, a larger portion of total transmitted power may converted to DC current at the implantable medical device when a smaller duty cycle is used. To illustrate, results of the in vivo testing indicated that for a 0.5 W average power transmitted, a 100% duty cycle provided less than 0.10 mW of DC power at the ocular implant. A 50% duty cycle provided more power at the ocular implant than the 100% duty cycle, but still less than 0.10 mW. A 25% duty cycle provided between 0.25 mW and 0.30 mW of DC power at the ocular implant. A 10% duty cycle provided approximately 0.40 mW of DC power at the ocular implant. Finally, a 5% duty cycle provided approximately 0.60 mW of DC power at the ocular implant.

Figure 11:
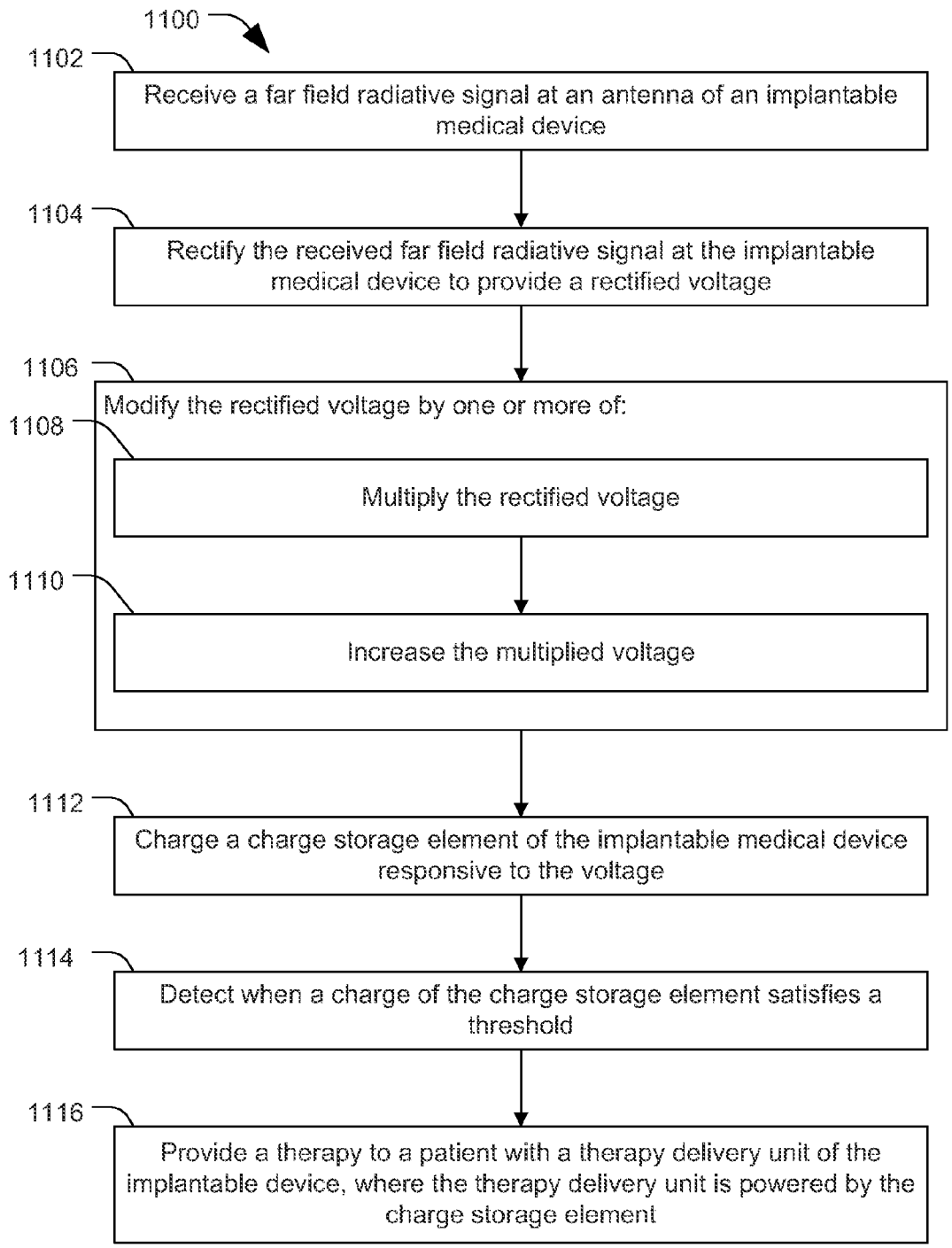
FIG. 11 is flow chart of a particular embodiment of a method of powering an implantable medical device using a far field transmitter.

FIG. 11 is a flow chart of a particular embodiment of a method 1100 of powering an implantable medical device using a far field transmitter. The implantable medical device may correspond to one of the implantable medical devices 106, 206, 306, 406, 506, 606, 706, 806 or 906 of FIGS. 1-9 or one of the additional embodiments or variants described above.

The method 1100 includes, at 1102, receiving a far field radiative signal at an antenna of an implantable medical device. As explained above, a far field radiative signal may include a signal that is transmitted a distance of at least two times a wavelength of the signal. For example, a distance between an antenna of the implantable medical device and a transmitter transmitting the far field radiative signal may be greater than 0.1 meters, greater than 0.15 meters, greater than 0.25 meters, greater than 0.3 meters, greater than 0.5 meters, or greater than 1 meter. The method 1100 may also include, at 1104, rectifying the received far field radiative signal at the implantable medical device to provide a rectified voltage. For example, the rectifier/multiplier 112 may rectify the received far field radiative signal.

The method 1100 may include, at 1106, modifying the rectified voltage. For example, the rectified voltage may be modified, at 1108, by multiplying (i.e., increasing) the rectified voltage (e.g., by the rectifier/multiplier 112 of FIGS. 1-5). In another example, the rectified voltage may be modified, at 1110, by increasing the rectified voltage using a DC-to-DC converter (e.g., a step-up regulator or a boost converter, such as the DC-to-DC converter 118 of FIGS. 1-5). In another example, the rectified voltage may be modified by multiplying the rectified voltage to generate a multiplied voltage and increasing the multiplied voltage using the DC-to-DC converter. In another example, the rectified voltage may be modified by increasing the rectified voltage using DC-to-DC converter to generate an increased voltage and multiplying the increased voltage.

The method 1100 may also include, at 1112, charging a charge storage element (e.g., the charge storage element 112 of FIG. 1-5) of the implantable medical device responsive to the voltage. The method 1100 may also include, at 1114, detecting when a charge of the charge storage element satisfies a threshold. The method 1100 may further include, at 1116, providing a therapy to a patient using a therapy delivery unit of the implantable medical device that is powered by the charge storage element. In a particular embodiment, the therapy is provided responsive to the threshold being satisfied. For example, a control unit (such as the control unit 320 of FIGS. 4 and 5) may be configured to cause the therapy delivery unit to provide the therapy based at least in part on the threshold being satisfied.

In some embodiments, multiple implantable medical devices may be implanted at various locations (e.g., brain, cranial nerves, other nerves, other neural tissue or neural structures, or a combination thereof) and used in a coordinated fashion to provide a therapy to a patient. At least two of the implantable medical devices may be recharged using far field radiative signals and may be charged at different frequencies (e.g., in some embodiments, all of the implantable medical devices may be charged at different frequencies, or different groupings of implantable medical devices may be charged at different frequencies). An external device configured to transmit the different frequencies may control when therapy is delivered by the various implantable medical devices by controlling the frequency of the charging signal(s). The implantable medical device(s) that charges at the frequency of the charging signal being transmitted will charge to the level of being able to deliver a therapy (e.g., such as an electrical stimulation signal to a target tissue) for a particular duration. After the therapy is delivered for the particular duration, the implantable medical device(s) will not deliver another therapy until it is sufficiently recharged by the charging signal at that same frequency. Thus, the timing of the therapy delivery between the multiple implantable medical devices may be controlled by the external device and may occur in any sequence or pattern. Codes, or any other type of signaling, from the external device may also be used to control the charging and/or stimulation of the multiple implantable device for increased precision in coordinating therapy delivery. By placing multiple implantable devices at multiple locations, increased recruitment of nerve fibers and innervation into the brain and organs may be possible and may result in a more effective therapy for treating a patient's disorder, disease, or condition. Also, having multiple independently controlled stimulation sites may provide an almost limitless number of possibilities for delivering therapy. This high level of flexibility in therapy delivery may be achieved using devices that may be less invasive and less visible to the patient (e.g., the far field radiative powered device may be a much smaller device than the traditional therapy delivery devices).

Figure 12:
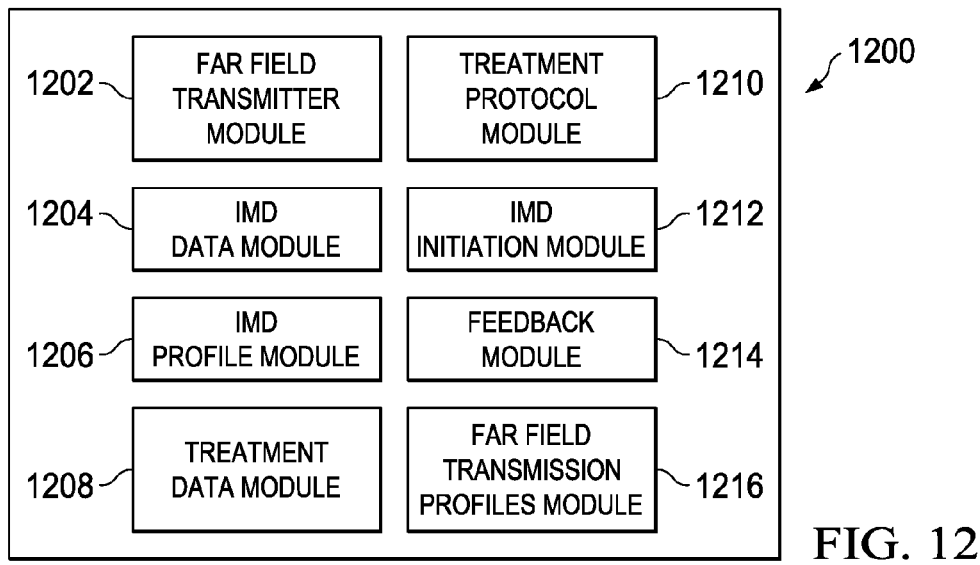
FIG. 12 is a block diagram for one or more memory elements, according to one embodiment.

FIG. 12 is a block diagram 1200 for one or more memory elements, according to one embodiment. In one example, one or more memory elements may include a far field transmitter module 1202, an IMD data module 1204, an IMD profile module 1206, a treatment data module 1208, a treatment protocol module 1210, an IMD initiation module 1212, a feedback module 1214, and a far field transmission profiles module 1216.

Far field transmitter module 1202 may store data relating to one or more far field transmitters. This data may include historical data, performance data (e.g., including transmitter settings), maintenance data, any other data relating to one or more transmitted far field radiative signals from one or more far field transmitters, or a combination thereof. This data may also include frequency data for one or more far field transmitters and/or for the one or more far field radiative signals.

IMD data module 1204 may include data relating to one or more implantable medical devices. This data may include frequency matching characteristics for the one or more implantable medical devices, historical data relating to one or more received far field radiative signals, data relating to one or more stimulations, maintenance data, modification data (e.g., calibration) relating to one or more implantable medical devices, any other performance characteristics for the one or more implantable medical devices, or a combination thereof.

IMD profile module 1206 may include data relating to the installation of the one or more implantable medical devices, the manufacturer information, specifications, any other performance characteristics for one or more implantable medical devices, or a combination thereof.

Treatment data module 1208 may include feedback data from the implementation of one or more treatment protocols. This data may include efficacy data, patient feedback data, medical staff feedback data, one or more body parameter (e.g., blood pressure, heart rate, etc.) feedback data, any other feedback data, or a combination thereof.

Treatment protocol module 1210 may include data relating to one or more treatment protocols. For example, a first treatment protocol based on a patient having a seizure disorder may include charging a first implantable medical device (IMD) 1310, a third implantable medical device (IMD) 1314, and a fourth implantable medical device (IMD) 1316 (see FIG. 13A) to provide one or more stimulations on a predetermined basis (e.g., 1 microsecond, 30 microseconds, 1 second, 5 seconds, 10 seconds, 15 seconds, 30 seconds, 1 minute, 5 minutes, 20 minutes, one hour, two hours, or any other time period) or responsive to feedback. The far field radiative signals used to charge the first IMD 1310, the third IMD 1314, and the fourth IMD 1316, respectively, may each have a different frequency, or one or more of the far field radiative signals may have a different frequency. In another example, the first treatment protocol may include initiating charging of the first IMD 1310 to provide a first stimulation at time T (e.g., reference point=0), initiating charging of the third IMD 1314 to provide a second stimulation at time T+X (e.g., where X may be 0 seconds, 10 seconds, 20 seconds, 1 minute, 5 minutes, 1 hour, or any other time period), and initiating charging of the fourth IMD 1316 to provide a third stimulation at time T+Y (e.g., where Y may be 0 seconds, 10 seconds, 20 seconds, 1 minute, 5 minutes, 1 hour, or any other time period).

The charge initiation and stimulation sequence may follow a predetermined order. For example, charging may be initiated at the first IMD 1310 followed by the third IMD 1314 and then the fourth IMD 1316. The stimulation sequence may follow the charge initiation sequence. In some embodiments, the stimulation sequence may be different from the charge initiation sequence. In some embodiments the charge initiation sequence for the multiple devices may be synchronized or not synchronized. For example, the charge initiation sequence may be simultaneous, staggered (e.g., a portion of the charging charge of one device may overlap or not overlap with another device), interleaved, random (e.g., random within a range), pseudorandom, predetermined (e.g., repeat the same predetermined sequence and/or different predetermined sequences), responsive to feedback from one or more sources (e.g., user, external device, one or more body parameters (e.g., sensed body parameters, such as heart rate, ECG, EEG, EMG, respiration, motion, temperature, blood oxygen level, or any other sensed or derived body parameter), time of day, determined patient activity and/or location), responsive to a received initiation code, or a combination thereof. In some embodiments, the charge initiation of the one or more implantable medical devices may operate independently from one another. In some embodiments, a first time interval between subsequent charge initiations of a first IMD may be different from a second time interval of subsequent charge initiations of a second IMD. For example, the first time interval may be a percentage of the second time interval (e.g., first time interval may be 40% of the second time interval), the first time interval and the second time interval may be a ratio (e.g., the first time interval may be equivalent to ten of the second time intervals) or may be a multiple of the other (e.g., the first time interval may be five times longer than the second time interval), or any other coordinated pattern or sequence. In some embodiments, the stimulation sequence for multiple devices may be synchronized or not synchronized. For example, the stimulation sequence for multiple devices may be simultaneous (e.g., two or more IMDs stimulate at approximately the same time), staggered (e.g., a portion of the stimulation deliver of one device may overlap or not overlap with another device), interleaved, random (e.g., random within a range), pseudorandom, predetermined (e.g., repeat the same predetermined sequence and/or in different predetermined sequences), responsive to feedback from one or more sources (e.g., user, external device, one or more body parameters (e.g., sensed body parameters, such as heart rate, ECG, EEG, EMG, respiration, motion, temperature, blood oxygen level, or any other sensed or derived body parameter), time of day, determined patient activity and/or location), responsive to a received initiation code, or a combination thereof. In some embodiments, the stimulation provided by the one or more implantable medical devices may operate independently from one another. In some embodiments, a first time interval between subsequent stimulations of a first IMD may be different from a second time interval of subsequent stimulations of a second IMD. For example, the first time interval may be a percentage of the second time interval (e.g., first time interval may be 40% of the second time interval), the first time interval and the second time interval may be a ratio (e.g., the first time interval may be equivalent to ten of the second time intervals) or may be a multiple of the other (e.g., the first time interval may be five times longer than the second time interval), or any other coordinated pattern or sequence. In another example, a first charge initiation and stimulation sequence may occur in the following order: the first IMD 1310, the third IMD 1314, and the fourth IMD 1316. After the first charge initiation and stimulation sequence has been implemented a predetermined number of times (e.g., 1 to N times) and/or based on one or more feedback signals, then a second charge initiation and stimulation sequence may be implemented. After the second charge initiation and stimulation sequence has been implemented a predetermined number of times (e.g., 1 to N times) and/or based on one or more feedback signals, then a third charge initiation and stimulation sequence may be implemented. After an Nth charge initiation and stimulation sequence has been implemented for a predetermined number of times (e.g., 1 to N times) and/or based on one or more feedback signals, then another charge initiation and stimulation sequence (e.g., first charge initiation and stimulation sequence, second charge initiation and stimulation sequence, third charge initiation and stimulation sequence, . . . and/or Nth charge initiation and stimulation sequence) may be implemented. The second charge initiation and stimulation sequence may occur in the following order: the third IMD 1314, the first IMD 1310, and the fourth IMD. The third charge initiation and stimulation sequence may occur in the following order: the fourth IMD 1316, the first IMD 1310, and the third IMD 1314. The one or more implantable medical devices may provide stimulation immediately after being charged (e.g., reaching a charge threshold, based on an initiation signal or code, or at any time thereafter.

In another example, a second treatment protocol based on a patient having a depression disorder may include charging a second IMD 1312 to provide one or more stimulations on a predetermined basis (e.g., 1 microsecond, 30 microseconds, 1 second, 5 seconds, 10 seconds, 15 seconds, 30 seconds, 1 minute, 3 minutes, 5 minutes, 20 minutes, one hour, two hours, twelve hours, etc.). This treatment sequence is repeated in a predetermined pattern and/or based on one or more feedback mechanism (e.g., treatment feedback signals, one or more external device signals, one or more patient inputs, one or more medical personnel inputs, one or more body parameters, etc.). In one example, based on one or more feedback mechanisms, the predetermined basis (e.g., 5 seconds, 10 seconds, 30 seconds, 1 minute, 3 minutes, 5 minutes, 20 minutes, one hour, two hours, twelve hours, etc.) may be modified. For example, the second treatment protocol may provide that second IMD 1312 be charged and provide stimulation every 10 minutes, but based on one or more feedback mechanisms, the system, device, and/or method modifies the treatment sequence to provide stimulation every 5 minutes for a predetermined number of times and/or until a feedback signal is received which modifies the treatment protocol.

In another example, a third treatment protocol based on a patient having an obesity disorder may include charging second IMD 1312, third IMD 1314, and fourth IMD 1316 to provide one or more stimulations on a predetermined basis (e.g., 1 microsecond, 30 microseconds, 1 second, 5 seconds, 10 seconds, 15 seconds, 30 seconds, 1 minute, 5 minutes, 20 minutes, one hour, two hours, twenty-four hours, etc.). In another example, the third treatment protocol may include charging the second IMD 1312 to provide a first stimulation at time T (e.g., reference point=0), charging third IMD 1314 to provide a second stimulation at time T+X (e.g., X maybe 0 seconds, 1 second, 5 seconds, 2 minutes, 10 minutes, 6 hours, or any other time period), and charging fourth IMD 1316 to provide a third stimulation at time T+Y (e.g., Y may be 0 seconds, 1 second, 2 seconds, 6 seconds, 1 minute, 5 minutes, 1 hour, or any other time period).

In one example, the first treatment sequence may include stimulating with the second IMD 1312 at time 0, then stimulating with the third IMD 1314 one second later, and then stimulating with the fourth IMD 1316 one second later. The second treatment sequence may include stimulating with the second IMD 1312 at time 0, then stimulating with the third IMD 1314 five seconds later, and then stimulating with the fourth IMD 1316 one second later. The third treatment sequence may include stimulating with the second IMD 1312 at time 0, then stimulating with the fourth IMD 1316 one minute later, and then stimulating with the third IMD 1314 one minute later.

IMD initiation module 1212 may include data relating to the initiation of one or more IMDs. This information may include time data, charge level, efficiency, a code or codes specific to each IMD to initiate charging and/or stimulation, a communication frequency of each IMD, a charge frequency of each IMD, any other data relating to the one or more IMD initiations, or a combination thereof.

Feedback module 1214 may include data relating to feedback signals from the one or more IMDs, one or more external devices, one or more body sensors, any other feedback device, or a combination thereof.

Far field transmission profiles module 1216 may store data relating to one or more transmission sequences for the one or more far field radiative signals. Further, far field transmission profiles module 1216 may also store data relating to the frequency matching characteristics for one or more IMDs.

Figure 13A:
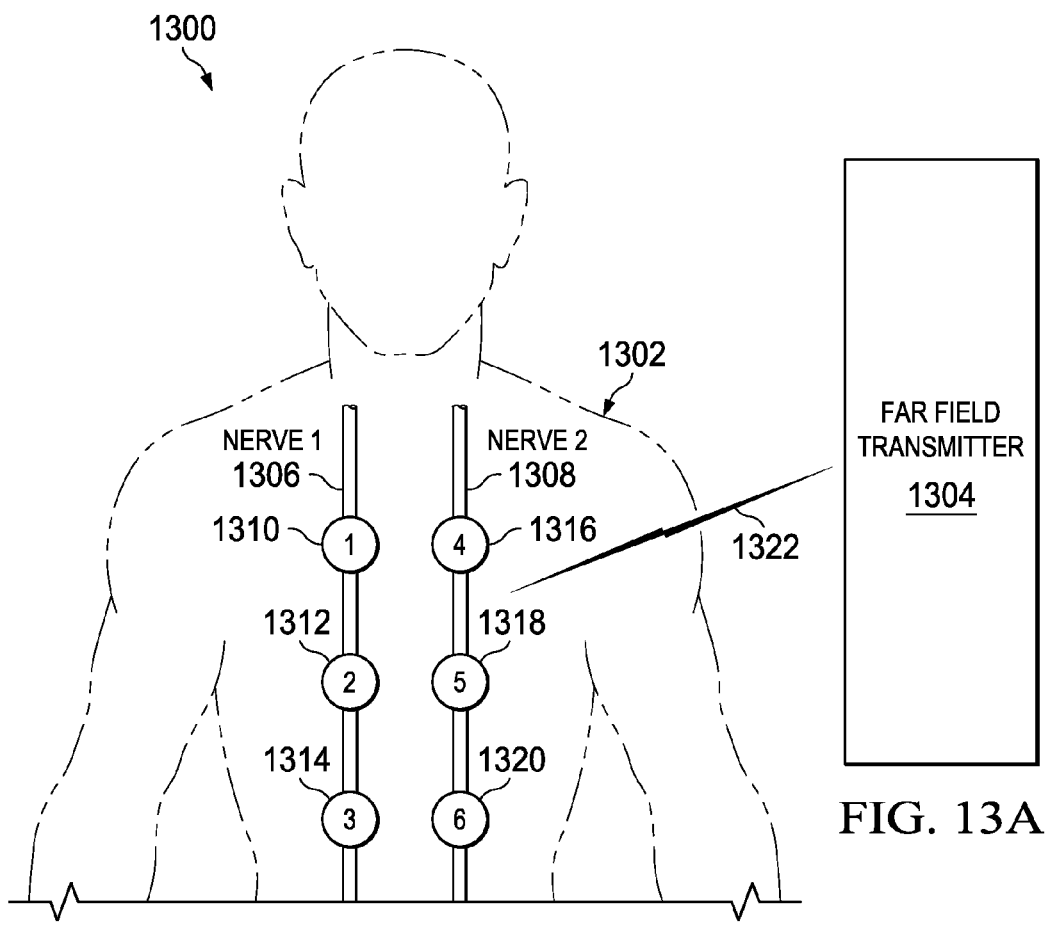
FIGS. 13A-13D are various IMD configurations and stimulation protocols, according to various embodiments.

FIGS. 13A-13D are illustrations of various IMD configurations and stimulation profiles, according to various embodiments. In FIG. 13A, a patient 1302 has numerous nerves in their body, including twelve cranial nerves (e.g., olfactory nerve, optic nerve, oculomotor nerve, trochlear nerve, trigeminal nerve, abducens nerve, facial nerve, vestibulocochlear nerve, glossopharyngeal nerve, vagus nerve, spinal accessory nerve, hypoglossal nerve). One or more of the implantable medical devices may be coupled, attached, or placed in proximity to one or more of the cranial nerves, including any of the various branches or structures (e.g., ganglion, plexus) of the cranial nerves.

As an example, the vagus nerve includes a left and right vagus nerve, and several branches, including the auricular nerve, the pharyngeal nerve, the superior laryngeal nerve, the superior cervical cardiac branches, the inferior cervical cardiac branch, the recurrent laryngeal nerve, the thoracic cardiac branches, the branches to the pulmonary plexus, the branches to the esophageal plexus, the anterior vagal trunk, the posterior vagal trunk, the Hering-Breuer reflex in alveoli, gastric nerves, mesenteric nerves, branches of the cardiac plexus, splenic branches, pancreatic branches, and branches to the small and large intestine. Other sites associated with the vagus nerve for stimulation by an implantable medical device include the nodose ganglion, the jugular ganglion, celiac ganglion and plexus, esophageal plexus, pulmonary plexus, cardiac plexus, superior mesenteric plexus, renal plexus, or any other site associated with the vagus nerve. The implantable medical device may be coupled, attached, or placed in proximity to one or more of these branches, or structures of the vagus nerve listed, or any other branches or structures of the vagus nerve.

As another example, the trigeminal nerve includes a left and right trigeminal nerve, and several branches, including three main divisions the ophthalmic nerve, the maxillary nerve, and the mandibular nerve. The ophthalmic nerve includes the nasociliary nerve, the lacrimal nerve, the frontal nerve, and the meningeal branch. The nasociliary nerve includes the sensory root of ciliary ganglion, the posterior ethmoidal nerve, the long and short ciliary nerves, the infratrochlear nerve, and the anterior ethmoidal nerve. The frontal nerve includes the supratrochlear nerve, and the supraorbital nerve. The maxillary nerve includes the middle meningeal nerve in the meninges, the infraorbital nerve through infraorbital canal, the zygomatic nerve (zygomaticotemporal nerve, zygomaticofacial nerve) through inferior orbital fissure, the nasal branches (nasopalatine) through sphenopalatine foramen, the superior alveolar nerves (posterior superior alveolar nerve, middle superior alveolar nerve, anterior superior alveolar nerve), the palatine nerves (greater palatine nerve, lesser palatine nerve), the pharyngeal nerve, the anterior superior alveolar nerve, the infraorbital nerve, the inferior palpebral nerve, and the superior labial nerve. The mandibular nerve includes the nervus spinosus (meningeal branch), the medial pterygoid nerve (the nerve to tensor tympani and the nerve to tensor veli palatine), the masseteric nerve, the deep temporal nerves (anterior and posterior), the buccal nerve (a sensory nerve), the lateral pterygoid nerve, the auriculotemporal nerve, the lingual nerve, the inferior alveolar nerve, and the motor branch to mylohyoid and anterior belly of digastric muscles (mylohyoid nerve). The implantable medical device may be coupled, attached, or placed in proximity to one or more of these branches, or structures of the trigeminal nerve listed, or any other branches or structures of the trigeminal nerve.

As another example, the glossopharyngeal nerve includes a left and right glossopharyngeal nerve and several branches, including the tympanic nerve, the stylopharyngeal nerve, the tonsillar nerve, the nerve to carotid sinus, the branches to the posterior third of tongue, the lingual branches, and a communicating branch to the Vagus nerve. The implantable medical device may be coupled, attached, or placed in proximity to one or more of these branches, or structures of the glossopharyngeal nerve listed, or any other branches or structures of the glossopharyngeal nerve. As another example, the implantable medical device may be coupled, attached, or placed in proximity to the hypoglossal nerve.

Figure 13B:
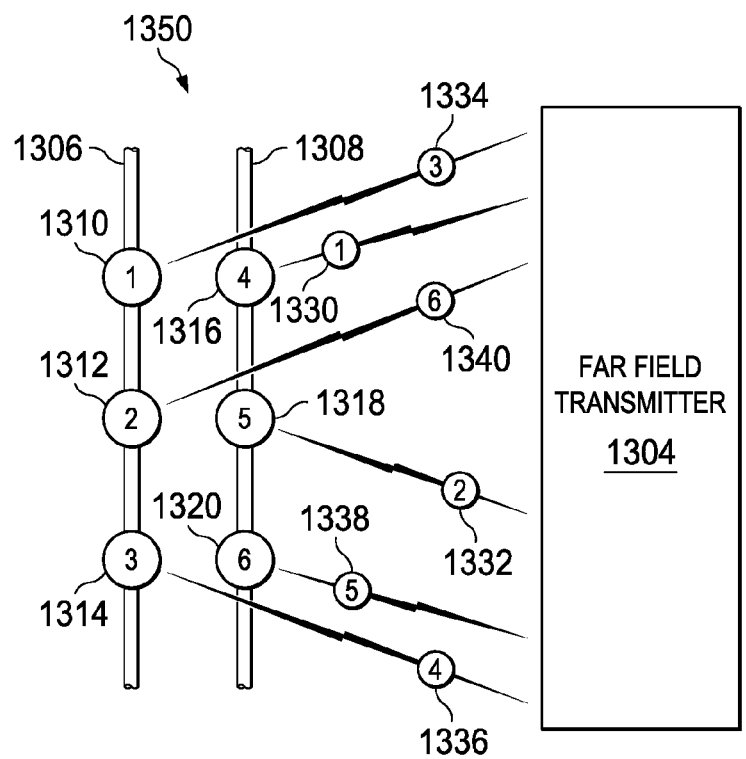
Figure 13C:
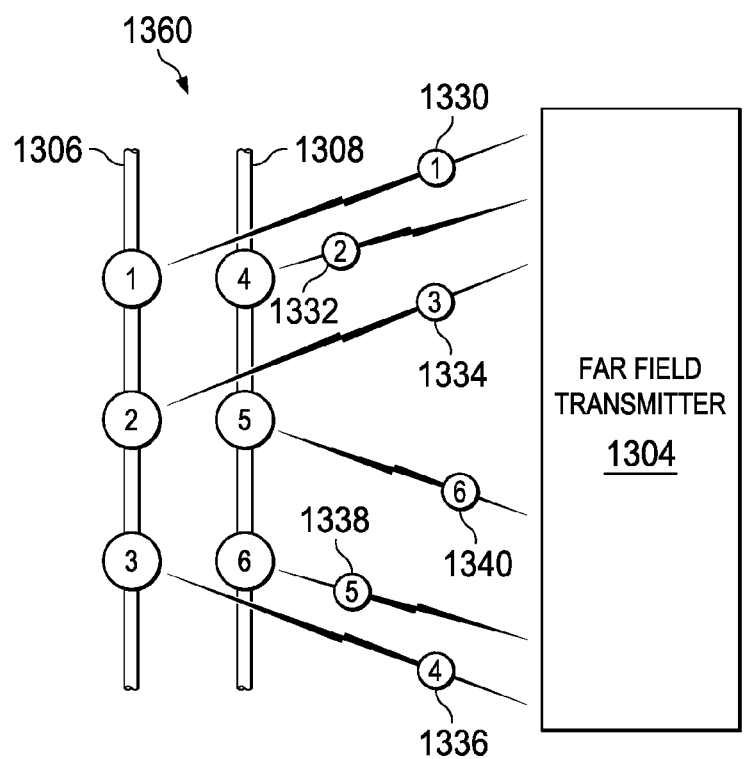

For simplicity, two nerves are shown in FIGS. 13A-13C; however, one or more implantable medical devices may be coupled, attached, or placed in proximity to one or more of the twelve cranial nerves and any of their associated branches or structures, including those listed above, in any configuration. In some embodiments, a first IMD may provide therapy to a first nerve area located before a particular nerve branch of a cranial nerve and a second IMD may provide therapy to a second nerve area located after the particular nerve branch. In some embodiments, the first IMD may provide therapy to a first nerve area located at a first nerve branch after a particular nerve branch of a cranial nerve and the second IMD may deliver therapy to a second nerve area located at a second nerve branch after the particular nerve branch. In some embodiments, one or more of the implantable medical devices may be coupled, attached, or placed in proximity to the surface of the brain or inside the brain. For example, the implantable medical device may be configured for cortical brain stimulation or deep brain stimulation. In some embodiments, one or more of the implantable medical devices may be a drug delivery device (e.g., drug pump) to deliver a drug to a portion of the brain or body of the patient. In some embodiments, one or more of the implantable medical devices may be a sensor configured to sense a body parameter. In one example, a first nerve 1306 and a second nerve 1308 are illustrated. First nerve 1306 may include a first IMD 1310 placed in a first location, a second IMD 1312 placed in a second location, and a third IMD 1314 placed in a third location on first nerve 1306. Second nerve 1308 may include a fourth IMD 1316 placed in a fourth location, a fifth IMD 1318 placed in a fifth location, and a sixth IMD 1320 placed in a sixth location on second nerve 1308. The IMDs 1310-1320 are each configured to be charged by a far field radiative signal (charging signal) at a particular frequency. For example, the first IMD 1310 may charge at a first frequency, the second IMD 1312 may charge at a second frequency, the third IMD 1314 may charge at a third frequency, the fourth IMD 1316 may charge at a fourth frequency, the fifth IMD 1318 may charge at a fifth frequency, and the sixth IMD 1320 may charge at a sixth frequency. Each of the six charging frequencies may be different frequencies, at least two of the charging frequencies may be the same frequencies (e.g., the first frequency and the second frequency may be the same frequency), at least three of the charging frequencies may be the same, at least four of the frequencies may be the same frequency, five of the frequencies may be the same frequency, or all of the six charging frequencies may be the same frequency.

In one embodiment, a far field transmitter 1304 may transmit one or more far field radiative signals 1322 to charge one or more of the IMDs 1310-1320. One or more far field radiative signals 1322 may be transmitted at any frequency (e.g., 900 MHz, 2.4 GHz, 5.8 GHz, etc.). Further, the far field transmitter 1304 may include one or more transmitters to transmit one or more frequencies. For example, a first far field radiative signal may be transmitted at a first frequency of 900 MHz, a second far field radiative signal may be transmitted at a second frequency of 2.4 GHz, and a third far field radiative signal may be transmitted at a third frequency of 5.8 GHz. These far field radiative signals may charge one or more devices based on the charging profiles of the one or more devices. For example, the first IMD 1310 may charge at the first frequency, and the second IMD 1312 may charge at the second frequency. In addition, the first IMD 1310 may charge at more than one frequency (e.g., 1 to N frequencies). For example, first IMD 1310 may charge at the first frequency (e.g., 900 MHz) and at the second frequency (e.g., 2.4 GHz).

In one example, a first far field radiative signal and a second far field radiative signal may have a frequency of approximately 433 MHz and 900 MHz, respectively, approximately 433 MHz and 2.4 GHz, respectively, approximately 433 MHz and 5.8 GHz, respectively, approximately 900 MHz and 2.4 GHz, respectively, approximately 900 MHz and 5.8 GHz, respectively, approximately 2.4 GHz and 5.8 GHz, respectively, or any other frequency suitable for far field powering, including frequencies permitted by government regulatory bodies for far field powering (e.g., Federal Communications Commission).

In FIG. 13B, an illustration of a first charging procedure 1350 utilized in a treatment regimen is shown, according to one embodiment. First charging procedure 1350 may include a first far field radiative signal 1330, a second far field radiative signal 1332, a third far field radiative signal 1334, a fourth far field radiative signal 1336, a fifth far field radiative signal 1338, and a sixth far field radiative signal 1340 being transmitted from far field transmitter 1304. The far field transmitter 1304 may include one or more transmitters to transmit the multiple far field radiative signals. In some embodiments the transmission initiation of the far field radiative signals, the charging signals, may be simultaneous, staggered, random, pseudorandom, predetermined (e.g., repeat the same predetermined sequence and/or different predetermined sequences), responsive to feedback from one or more sources (e.g., user, external device, one or more body parameters, time of day, determined patient activity and/or location), responsive to a received initiation code, or a combination thereof. In some embodiments, a first time interval between subsequent transmission initiations to a first IMD may be different from a second time interval of subsequent transmission initiations to a second IMD. For example, the first time interval may be a percentage of the second time interval (e.g., first time interval may be 40% of the second time interval), the first time interval and the second time interval may be a ratio (e.g., the first time interval may be equivalent to ten of the second time intervals) or may be a multiple of the other (e.g., the first time interval may be five times longer than the second time interval), or any other coordinated pattern or sequence. The first far field radiative signal 1330 may charge the fourth IMD 1316 at a first frequency at a fourth location on second nerve 1308. The second far field radiative signal 1332 may charge the fifth IMD 1318 at a second frequency at a fifth location on the second nerve 1308. The third far field radiative signal 1334 may charge the first IMD 1310 at a third frequency at a first location on the first nerve 1306. The fourth far field radiative signal 1336 may charge the third IMD 1314 at a fourth frequency at a third location on the first nerve 1306. The fifth far field radiative signal 1338 may charge the sixth IMD 1320 at a fifth frequency at a sixth location on the second nerve 1308. The sixth far field radiative signal 1340 may charge the second IMD 1312 at a sixth frequency at a second location on the first nerve 1306. The first frequency, second frequency, third frequency, fourth frequency, fifth frequency, and sixth frequency may be 433 MHz, 900 MHz, 928 MHz, 2.4 GHz, 2.5 GHz, and 5.8 GHz, respectively, 900 MHz, 900 MHz, 928 MHz, 2.4 GHz, 2.4 GHz, and 5.8 GHz, respectively, 900 MHz, 900 MHz, 900 MHz, 2.4 GHz, 2.4 GHz, and 2.4 GHz, respectively, 900 MHz, 2.4 GHz, 5.8 GHz, 900 MHz, 2.4 GHz, and 5.8 GHz, respectively, or any other combination of frequencies. In some embodiments, each of the six charging frequencies may be different frequencies, at least two of the charging frequencies may be the same frequencies (e.g., the first frequency and the second frequency may be the same frequency), at least three of the charging frequencies may be the same, at least four of the frequencies may be the same frequency, five of the frequencies may be the same frequency, or all of the six charging frequencies may be the same frequency.

The far field transmitter 1304 may transmit any number of far field radiative signals (e.g., 1 to N signals) at any number of frequencies, including 433 MHz to 434.79 MHz, 900 MHz to 928 MHz, 2.4 GHz to 2.5 GHz, 5.725 GHz to 5.875 GHz, or any other frequency suitable for far field powering, including frequencies permitted by government regulatory bodies for far field powering (e.g., Federal Communications Commission). The IMDs 1310-1320 may be located in any position on any nerve, nerve branch, nerve structure, brain surface, within the brain, or any combination thereof.

In one example, far field transmitter 1304 may transmit one or more far field radiative signals to charge one or more IMDs based on one or more protocols and profiles (e.g., treatment protocol, patient profiles, etc.), one or more treatment feedback signals, one or more patient inputs, one or more medical personnel inputs, one or more external device (e.g., monitoring device, programming device, etc.) signals, and/or one or more body parameters (e.g., heart rate, breathing rate, blood concentration levels, blood pressure, etc.).

One or more treatment protocols may be based on one or more disorders. The one or more disorders may include epilepsy, depression, seizures, autism, attention deficit/hyperactivity disorder, bulimia, compulsive overeating, obesity, anorexia nervosa, traumatic brain injury, stroke, coma, migraine, neuropathic pain, ischemia, congestive heart failure, angina, sleep disorders, a dementia disorder, any other disorder, and/or any combination thereof.

For example, a first treatment protocol based on a patient having a seizure disorder may include charging the first IMD 1310, the third IMD 1314, and the fourth IMD 1416 to provide one or more stimulations on a predetermined basis (e.g., 1 microsecond, 30 microseconds, 1 second, 5 seconds, 10 seconds, 15 seconds, 30 seconds, 1 minute, 5 minutes, 20 minutes, one hour, two hours, etc.), randomly, pseudo-randomly, based on feedback from one or more sources (e.g., user, external device, one or more body parameters, time of day, determined patient activity and/or location), responsive to a received initiation code, or a combination thereof. In another example, the first treatment protocol may include initiating charging the first IMD 1310 to provide a first stimulation at time T (e.g., reference point=0), initiating charging the third IMD 1314 to provide a second stimulation at time T+X (e.g., where X may be 0 seconds, 10 seconds, 20 seconds, 1 minute, 5 minutes, 1 hour, or any other time period), and initiating charging the fourth IMD 1316 to provide a third stimulation at time T+Y (e.g., where Y may be 0 seconds, 10 seconds, 20 seconds, 1 minute, 5 minutes, 1 hour, or any other time period).

The charge initiation and stimulation sequence may follow a predetermined order. For example, charging may be initiated at the first IMD 1310 followed by the third IMD 1314 and then the fourth IMD 1316. The stimulation sequence may follow the charge initiation sequence. In some embodiments, the stimulation sequence of the multiple IMDs may be different from the charge initiation sequence. In some embodiments the charge initiation sequence may be simultaneous, staggered, random, pseudorandom, predetermined (e.g., repeat the same predetermined sequence and/or different predetermined sequences), responsive to feedback from one or more sources (e.g., user, external device, one or more body parameters, time of day, determined patient activity and/or location), responsive to a received initiation code, or a combination thereof. In some embodiments, the charge initiation of the one or more implantable medical devices may operate independently from one another. In some embodiments, a first time interval between subsequent charge initiations of a first IMD may be different from a second time interval of subsequent charge initiations of a second IMD. For example, the first time interval may be a percentage of the second time interval (e.g., first time interval may be 40% of the second time interval), the first time interval and the second time interval may be a ratio (e.g., the first time interval may be equivalent to ten of the second time intervals) or may be a multiple of the other (e.g., the first time interval may be five times longer than the second time interval), or any other coordinated pattern or sequence. In some embodiments, the stimulation sequence may be simultaneous (e.g., two or more IMDs stimulate at approximately the same time), staggered, random, pseudo-random, predetermined (e.g., repeat the same predetermined sequence and/or in different predetermined sequences), responsive to feedback from one or more sources (e.g., user, external device, one or more body parameters, time of day, determined patient activity and/or location), responsive to a received initiation code, or a combination thereof. In some embodiments, the stimulation provided by the one or more implantable medical devices may operate independently from one another. In some embodiments, a first time interval between subsequent stimulations of a first IMD may be different from a second time interval of subsequent stimulations of a second IMD. For example, the first time interval may be a percentage of the second time interval (e.g., first time interval may be 40% of the second time interval), the first time interval and the second time interval may be a ratio (e.g., the first time interval may be equivalent to ten of the second time intervals) or may be a multiple of the other (e.g., the first time interval may be five times longer than the second time interval), or any other coordinated pattern or sequence. In another example, a first charge initiation and stimulation sequence may occur in the following order: the first IMD 1310, the third IMD 1314, and the fourth IMD 1316. After the first charge initiation and stimulation sequence has been implemented a predetermined number of times (e.g., 1 to N times) and/or based on one or more feedback signals, then a second charge initiation and stimulation sequence may be implemented. After the second charge initiation and stimulation sequence has been implemented a predetermined number of times (e.g., 1 to N times) and/or based on one or more feedback signals, then a third charge initiation and stimulation sequence may be implemented. After an Nth charge initiation and stimulation sequence has been implemented for a predetermined number of times (e.g., 1 to N times) and/or based on one or more feedback signals, then another charge initiation and stimulation sequence (e.g., first charge initiation and stimulation sequence, second charge initiation and stimulation sequence, third charge initiation and stimulation sequence, . . . and/or Nth charge initiation and stimulation sequence) may be implemented. The second charge initiation and stimulation sequence may occur in the following order: the third IMD 1314, the first IMD 1310, and the fourth IMD. The third charge initiation and stimulation sequence may occur in the following order: the fourth IMD 1316, the first IMD 1310, and the third IMD 1314. The one or more implantable medical devices may provide stimulation immediately after being charged or at any time thereafter.

In another example, a second treatment protocol based on a patient having a depression disorder may include charging a second IMD 1312 to provide one or more stimulations on a predetermined basis (e.g., 1 microsecond, 30 microseconds, 1 second, 5 seconds, 10 seconds, 15 seconds, 30 seconds, 1 minute, 3 minutes, 5 minutes, 20 minutes, one hour, two hours, twelve hours, etc.). This treatment sequence may be repeated in a predetermined pattern and/or based on one or more feedback mechanism (e.g., treatment feedback signals, one or more external device signals, one or more patient inputs, one or more medical personnel inputs, one or more body parameters, etc.). In one example, based on one or more feedback mechanisms, the predetermined basis (e.g., 1 microsecond, 30 microseconds, 1 second, 5 seconds, 10 seconds, 15 seconds, 30 seconds, 1 minute, 3 minutes, 5 minutes, 20 minutes, one hour, two hours, twelve hours, etc.) may be modified. For example, the second treatment protocol may provide that second IMD 1312 be charged and provide stimulation every 10 minutes but based on one or more feedback mechanisms, the system, device, and/or method modifies the treatment sequence to provide stimulation every 5 minutes for a predetermined number of times and/or until a feedback signal is received which modifies the treatment protocol.

In another example, a third treatment protocol based on a patient having an obesity disorder may include charging second IMD 1312, third IMD 1314, and fourth IMD 1316 to provide one or more stimulations on a predetermined basis (e.g., 1 microsecond, 30 microseconds, 1 second, 5 seconds, 10 seconds, 15 seconds, 30 seconds, 1 minute, 5 minutes, 20 minutes, one hour, two hours, twenty-four hours, etc.). In another example, the third treatment protocol may include charging the second IMD 1312 to provide a first stimulation at time T (e.g., reference point=0), charging third IMD 1314 to provide a second stimulation at time T+X (e.g., X maybe 0 seconds, 100 microseconds, 100 milliseconds, 1 second, 5 seconds, 2 minutes, 10 minutes, 6 hours, or any other time period), and charging fourth IMD 1316 to provide a third stimulation at time T+Y (e.g., Y may be 0 seconds, 100 microseconds, 100 milliseconds, 1 second, 2 seconds, 6 seconds, 1 minute, 5 minutes, 1 hour, or any other time period).

In one example, the first treatment sequence may include stimulating with the second IMD 1312 at time 0, then stimulating with the third IMD 1314 one second later, and then stimulating with the fourth IMD 1316 one second later. The second treatment sequence may include stimulating with the second IMD 1312 at time 0, then stimulating with the third IMD 1314 five seconds later, and then stimulating with the fourth IMD 1316 one second later. The third treatment sequence may include stimulating with the second IMD 1312 at time 0, then stimulating with the fourth IMD 1316 one minute later, and then stimulating with the third IMD 1314 one minute later.

In another example, a fourth treatment protocol based on a patient having an epilepsy disorder may include charging first IMD 1310, second IMD 1312, third IMD 1314, fourth IMD 1316, fifth IMD 1318, sixth IMD 1320, and an Nth IMD to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period). In another example, the fourth treatment protocol may include charging first IMD 1310 to provide a first stimulation at time T (e.g., reference point=0), charging second IMD 1312 to provide a second stimulation at time T+A (e.g., where A may be 0, 1 microsecond, 10 microseconds, 1 second, 5 seconds, 2 minute, 10 minutes, 6 hour, or any other time period), charging third IMD 1314 to provide a third stimulation at time T+B (e.g., where B may be 0, 75 microseconds, 1 second, 5 seconds, 2 minute, 10 minutes, 6 hour, or any other time period), charging fourth IMD 1316 to provide a fourth stimulation at time T+C (e.g., where C may be 0, 2 seconds, 6 seconds, 1 minute, 5 minutes, 1 hour, or any other time period), charging fifth IMD 1318 to provide a fifth stimulation at time T+D (e.g., where D may be 0, 5 seconds, 10 seconds, 1 minute, 5 minutes, 10 minutes, 1 hour, or any other time period), charging sixth IMD 1320 to provide a sixth stimulation at time T+E (e.g., where E may be 0, 7 seconds, 15 seconds, 1 minute, 5 minutes, 10 minutes, 1 hour, or any other time period), and/or charging an Nth IMD to provide an Nth stimulation at time T+F (e.g., where F may be 0, 15 seconds, 20 seconds, 1.5 minute, 5 minutes, 10 minutes, 1 hour, or any other time period).

In another example, a fifth treatment protocol based on a patient having an autism disorder may include charging first IMD 1310 and an Nth IMD to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, a sixth treatment protocol based on a patient having an attention deficit/hyperactivity disorder may include charging first IMD 1310, second IMD and an Nth IMD to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, a seventh treatment protocol based on a patient having a bulimia disorder may include charging first IMD 1310, second IMD 1312, third IMD 1314, and fourth IMD 1316 to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

For example, an eighth treatment protocol based on a patient having a compulsive overeating disorder may include charging first IMD 1310, second IMD 1312, third IMD 1314, fourth IMD 1316, and fifth IMD 1318 to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, a ninth treatment protocol based on a patient having an anorexia nervosa disorder may include charging second IMD 1312, third IMD 1314, fourth IMD 1316, fifth IMD 1318, and sixth IMD 1320 to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, a tenth treatment protocol based on a patient having a traumatic brain injury disorder may include charging second IMD 1312, third IMD 1314, fourth IMD 1316, and fifth IMD 1318 to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, an eleventh treatment protocol based on a patient having a stroke may include charging third IMD 1314, fourth IMD 1316, fifth IMD 1318, and sixth IMD 1320 to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, a twelfth treatment protocol based on a patient being in a coma may include charging third IMD 1314, fourth IMD 1316, and fifth IMD 1318 to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, a thirteenth treatment protocol based on a patient having a migraine disorder may include charging fourth IMD 1316, fifth IMD 1318, and sixth IMD 1320, to provide one or more stimulations on a predetermined basis (e.g., 1 microsecond, 30 microseconds, 1 second, 5 seconds, 10 seconds, 15 seconds, 30 seconds, 10 milliseconds, 100 milliseconds, 1 minute, 5 minutes, 20 minutes, one hour, two hours, twenty-four hours, or any other time period).

In another example, a fourteenth treatment protocol based on a patient having a neuropathic pain disorder may include charging fourth IMD 1316 and fifth IMD 1318 to provide one or more stimulations on a predetermined basis (e.g., 1 microsecond, 30 microseconds, 1 second, 5 seconds, 10 seconds, 15 seconds, 30 seconds, 10 milliseconds, 100 milliseconds, 1 minute, 5 minutes, 20 minutes, one hour, two hours, twenty-four hours, or any other time period).

In another example, a fifteenth treatment protocol based on a patient having an ischemia disorder may include charging fourth IMD 1316 and sixth IMD 1320 to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, a sixteenth treatment protocol based on a patient having a congestive heart failure disorder may include charging second IMD 1312, third IMD 1314, fifth IMD 1318, and sixth IMD 1320 to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, a seventh treatment protocol based on a patient having an angina disorder may include charging fifth IMD 1318 to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, an eighteenth treatment protocol based on a patient having a sleep disorder may include charging third IMD 1314 and an Nth IMD to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, a nineteenth treatment protocol based on a patient having an dementia disorder may include charging fifth IMD 1318, sixth IMD 1320, and an Nth IMD to provide one or more stimulations on a predetermined basis (e.g., 1 microsecond, 30 microseconds, 10 milliseconds, 100 milliseconds, 1 second, 5 seconds, 10 seconds, 15 seconds, 30 seconds, 1 minute, 5 minutes, 20 minutes, one hour, two hours, twenty-four hours, or any other time period).

In another example, there may be numerous treatment protocols (e.g., 1 to N) for a seizure disorder. Based on a first patient profile (e.g., age, sex, BMI value, height, treatment history, physical health, etc.), a first patient may be treated with a first treatment protocol for their seizure disorder. The first treatment protocol may be to stimulate utilizing first IMD 1310, second IMD 1312, and third IMD 1314 on a first predetermined pattern. The first predetermined pattern may be to stimulate from first IMD 1310 at time T=0, then stimulate from second IMD 1312 at time T=1, and then stimulate from third IMD 1314 at time T=2. In another example, based a second patient profile (e.g., age, sex, BMI value, height, treatment history, physical health, etc.), a second patient may be treated with a second treatment protocol for their seizure disorder. The second treatment protocol may be to stimulate utilizing first IMD 1310, second IMD 1312, and third IMD 1314 on a second predetermined pattern. The second predetermined pattern may be to stimulate from first IMD 1310 at time T=0, then stimulate from second IMD 1312 at time T=5, and then stimulate from third IMD 1314 at time T=20. In another example, based a third patient profile (e.g., age, sex, BMI value, height, treatment history, physical health, etc.), a third patient may be treated with a third treatment protocol for their seizure disorder. The third treatment protocol may be to stimulate utilizing fourth IMD 1316, second IMD 1312, and sixth IMD 1320 on a third predetermined pattern. The third predetermined pattern may be to stimulate from fourth IMD 1316 at time T=0, then stimulate from second IMD 1312 at time T=2, and then stimulate from sixth IMD 1320 at time T=10.

In some embodiments, at least one IMD will have a different charging frequency than another IMD. As such, the charging and stimulation pattern of the IMDs may, in part, be controlled by the frequency of the far field radiative signal or signals transmitted from the far field transmitter 1304. In one example, the far field transmitter 1304 may transmit far field radiative signals to charge IMDs based on a first treatment protocol. After receiving one or more treatment feedback signals, the far field transmitter 1304 may modify (e.g., change) which far field radiative signals are transmitted to modify (e.g., change) which IMDs are charged to modify (e.g., change) the treatment protocol. Only the IMDs configured to charge at the frequency of one or more of the far field radiative signals being transmitted will charge. In another example, after receiving one or more treatment feedback signals, far field transmitter 1304 may not modify which far field radiative signals are transmitted. However, a control device may prohibit one or more IMDs from producing one or more stimulations. In another example, after receiving one or more treatment feedback signals, the far field transmitter 1304 may modify (e.g., change) which far field radiative signals are transmitted to modify (e.g., change) which IMDs are charged to modify (e.g., change) the treatment protocol. In this example, the control device may also prohibit one or more IMDs from producing one or more stimulations.

In another example, two or more different treatment protocols (e.g., 2 to N) for one disorder may be utilized based on one or more criteria. For example, a first treatment protocol for a seizure disorder may be utilized when a warning signal that an imminent seizure event may occur, a second treatment protocol for a seizure disorder may be utilized when an actual seizure event is occurring, a third treatment protocol for a seizure disorder may be utilized when an actual seizure event has occurred, and/or a fourth treatment protocol for a seizure disorder may be utilized when none of the above-events are determined.

In another example, two or more difference treatment protocols (e.g., 2 to N) may be utilized based on a patient having two or more different disorders. For example, a first treatment protocol for a seizure disorder may be utilized and a second treatment protocol for a depression disorder may be utilized. In another example, a first treatment protocol for a seizure disorder may be utilized when a warning signal that an imminent seizure event may occur, when an actual seizure event is occurring, and/or when an actual seizure event has occurred and a second treatment protocol for a seizure disorder may be utilized when none of the above-events are determined. In addition, a third treatment protocol may be utilized for a depression disorder. Further, a fourth treatment protocol may be utilized for an overeating disorder.

In another example, the far field transmitter 1304 may transmit one or more far field radiative signals to charge one or more IMDs based on a first treatment protocol. After receiving one or more signals from one or more external devices, far field transmitter 1304 may modify (e.g., change) which far field radiative signals are transmitted to modify (e.g., change) which IMDs are charged to modify (e.g., change) the treatment protocol. Only the IMDs configured to charge at the frequency of one or more of the far field radiative signals being transmitted will charge. In another example, after receiving one or more treatment feedback signals, far field transmitter 1304 may not modify which far field radiative signals are transmitted. However, a control device may prohibit one or more IMDs from producing one or more stimulations. In another example, after receiving one or more treatment feedback signals, the far field transmitter 1304 may modify (e.g., change) which far field radiative signals are transmitted to modify (e.g., change) which IMDs are charged to modify (e.g., change) the treatment protocol. In this example, the control device may also prohibit one or more IMDs from producing one or more stimulations.

In another example, the far field transmitter 1304 may transmit one or more far field radiative signals to charge one or more IMDs based on a first treatment protocol. After receiving one or more patient inputs, the far field transmitter 1304 may modify (e.g., change) which far field radiative signals are transmitted to modify (e.g., change) which IMDs are charged to modify (e.g., change) the treatment protocol. Only the IMDs configured to charge at the frequency of one or more of the far field radiative signals being transmitted will charge. In another example, after receiving one or more treatment feedback signals, the far field transmitter 1304 may not modify which far field radiative signals are transmitted. However, a control device may prohibit one or more IMDs from producing one or more stimulations. In another example, after receiving one or more treatment feedback signals, the far field transmitter 1304 may modify (e.g., change) which far field radiative signals are transmitted to modify (e.g., change) which IMDs are charged to modify (e.g., change) the treatment protocol. In this example, the control device may also prohibit one or more IMDs from producing one or more stimulations.

In another example, a patient may receive two or more treatment protocols (e.g., 2 to N). After experiencing these treatment protocols, the patient may determine that a second treatment protocol is better than any other treatment protocol. Based on this input for the patient, the second treatment protocol may be implemented as the sole treatment protocol, the primary treatment protocol, and/or any other designation.

In another example, a patient may receive two or more treatment protocols (e.g., 2 to N). After obtaining data relating to these treatment protocols, a medical personnel may determine that a third treatment protocol is better than any other treatment protocol. Based on this input for the patient, the third treatment protocol may be implemented as the sole treatment protocol, the primary treatment protocol, and/or any other designation.

In another example, the far field transmitter 1304 may transmit one or more far field radiative signals to charge one or more IMDs based on a first treatment protocol. After receiving one or more body parameter signals, the far field transmitter 1304 may modify (e.g., change) which far field radiative signals are transmitted to modify (e.g., change) which IMDs are charged to modify (e.g., change) the treatment protocol. In another example, after receiving one or more treatment feedback signals, the far field transmitter 1304 may not modify which far field radiative signals are transmitted. However, a control device may prohibit one or more IMDs from producing one or more stimulations. In another example, after receiving one or more treatment feedback signals, the far field transmitter 1304 may modify (e.g., change) which far field radiative signals are transmitted to modify (e.g., change) which IMDs are charged to modify (e.g., change) the treatment protocol. In this example, the control device may also prohibit one or more IMDs from producing one or more stimulations.

In another example, the one or more body parameter signals may indicate that the patient is sleeping, exercising, lying down, sitting, and/or any other human function.

In FIG. 13C, an illustration of a second charging procedure 1360 utilized in a treatment regimen is shown, according to one embodiment. The second charging procedure 1360 may include first far field radiative signal 1330, second far field radiative signal 1332, third far field radiative signal 1334, fourth far field radiative signal 1336, fifth far field radiative signal 1338, and sixth far field radiative signal 1340 being transmitted from the far field transmitter 1304. The far field transmitter 1304 may transmit one or more far field radiative signals in a predetermined order. In other embodiments the transmission sequence may be simultaneous, staggered, random, pseudorandom, predetermined (e.g., repeat the same predetermined sequence and/or different predetermined sequences), responsive to feedback from one or more sources (e.g., user, external device, one or more body parameters, time of day, determined patient activity and/or location, responsive to a received initiation code, or a combination thereof. In some embodiments, a first time interval between subsequent transmission initiations to a first IMD may be different from a second time interval of subsequent transmission initiations to a second IMD. For example, the first time interval may be a percentage of the second time interval (e.g., first time interval may be 40% of the second time interval), the first time interval and the second time interval may be a ratio (e.g., the first time interval may be equivalent to ten of the second time intervals) or may be a multiple of the other (e.g., the first time interval may be five times longer than the second time interval), or any other coordinated pattern or sequence.

For example, the far field transmitter 1304 may transmit the first far field radiative signal 1330. The first far field radiative signal 1330 may charge the first IMD 1310 in a first location on first nerve 1306 at a first frequency. After the far field transmitter 1304 has transmitted the first far field radiative signal 1330, then the far field transmitter may transmit the second far field radiative signal 1332. The second far field radiative signal 1332 may charge the fourth IMD 1316 in a fourth location on the second nerve 1308 at a second frequency. After the far field transmitter 1304 has transmitted the second far field radiative signal 1332, then the far field transmitter may transmit the third far field radiative signal 1334. The third far field radiative signal 1334 may charge the second IMD 1312 in a second location on the first nerve 1306 at a third frequency. After the far field transmitter 1304 has transmitted the third far field radiative signal 1334, then the far field transmitter may transmit the fourth far field radiative signal 1336. The fourth far field radiative signal 1336 may charge the third IMD 1314 in a third location on the first nerve 1306 at a fourth frequency. After the far field transmitter 1304 has transmitted the fourth far field radiative signal 1336, then the far field transmitter 1304 may transmit the fifth far field radiative signal 1338. The fifth far field radiative signal 1338 may charge the sixth IMD 1320 in a sixth location on the second nerve 1308 at a fifth frequency. After the far field transmitter 1304 has transmitted the fifth far field radiative signal 1338, then the far field transmitter 1304 may transmit the sixth far field radiative signal 1340. The sixth far field radiative signal 1340 may charge the fifth IMD 1318 in a fifth location on the second nerve 1308 at a sixth frequency. In some embodiments, each of the six charging frequencies may be different frequencies, at least two of the charging frequencies may be the same frequencies (e.g., the first frequency and the second frequency may be the same frequency), at least three of the charging frequencies may be the same, at least four of the frequencies may be the same frequency, five of the frequencies may be the same frequency, or all of the six charging frequencies may be the same frequency.

Figure 13D:
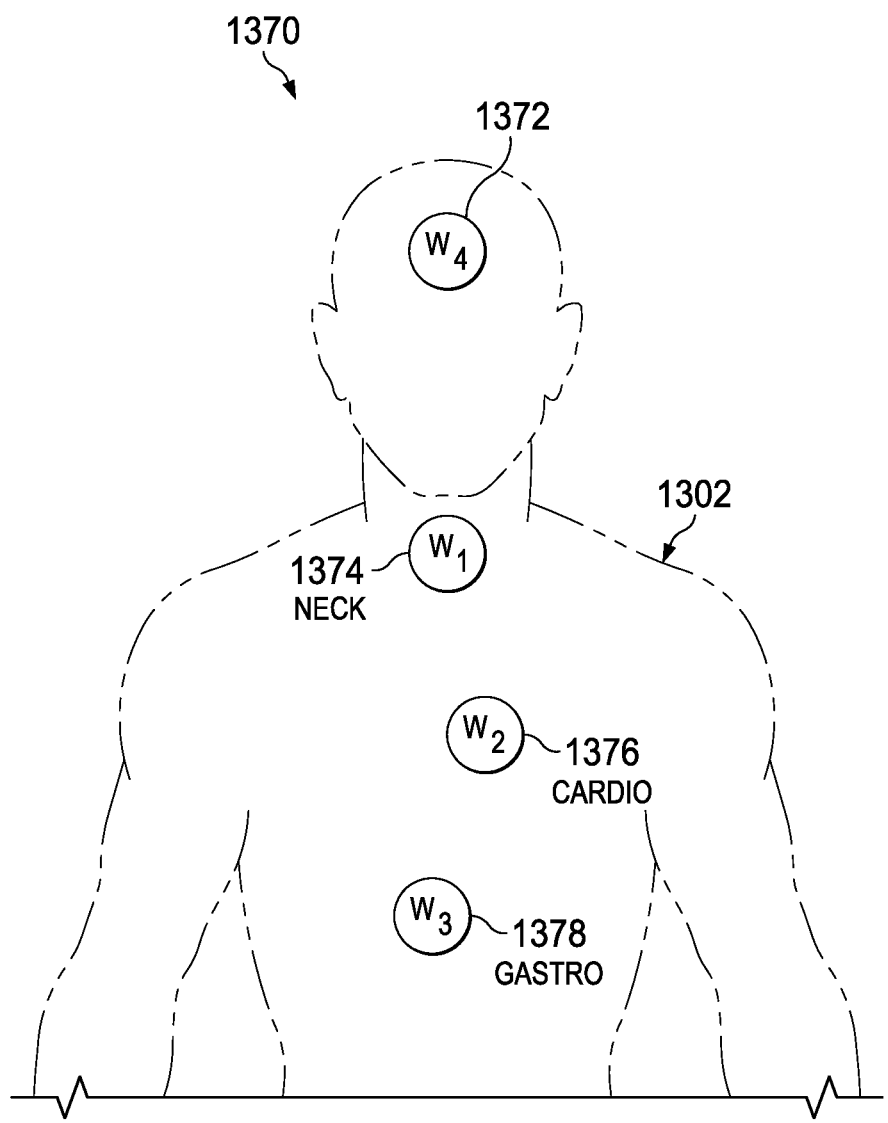

In FIG. 13D, an illustration of various locations to place one or more IMDs is shown, according to an exemplary embodiment. In this example, a first IMD 1374 may be located in the neck region (e.g., coupled, attached, or placed in proximity to the vagus nerve, another cranial nerve, or other nerve in the neck region), a second IMD 1376 is located in the cardio region (e.g., coupled, attached, or placed in proximity to the vagus nerve, another cranial nerve, or other nerve in the cardio region), a third IMD 1378 is located in the gastro region (e.g., coupled, attached, or placed in proximity to the vagus nerve, another cranial nerve, or other nerve in the gastro region), and a fourth IMD 1372 is located in the head region (e.g., coupled, attached, or placed in proximity to the brain surface, within the brain, the vagus nerve, the trigeminal nerve, the hypoglossal nerve, the glossopharyngeal nerve, another cranial nerve, or other nerve in the head region). In some embodiments, the charging frequency of the IMDs may correspond to the region in which it is located (e.g., the neck region, the cardio region, the gastro region, and the head region may correspond to a first frequency, a second frequency, a third frequency, and a fourth frequency, respectively), the side of the body the target structure is on (e.g., the left vagus nerve and the left trigeminal nerve may correspond to a first frequency, and the right vagus and right trigeminal may correspond to a second frequency), the type of target tissue (e.g., the brain may correspond to a first frequency and one or more nerves may correspond to a second frequency), the particular target type (e.g., the vagus nerve may correspond to a first frequency the trigeminal nerve may correspond to a second frequency, and the hypoglossal nerve may correspond to a third frequency), the particular portion of the target (e.g., a primary portion of the vagus nerve may correspond to a first frequency, a first branch of the vagus nerve may correspond to a second frequency, and a second branch of the vagus nerve may correspond to a third frequency), or a combination thereof.

Figure 14A:
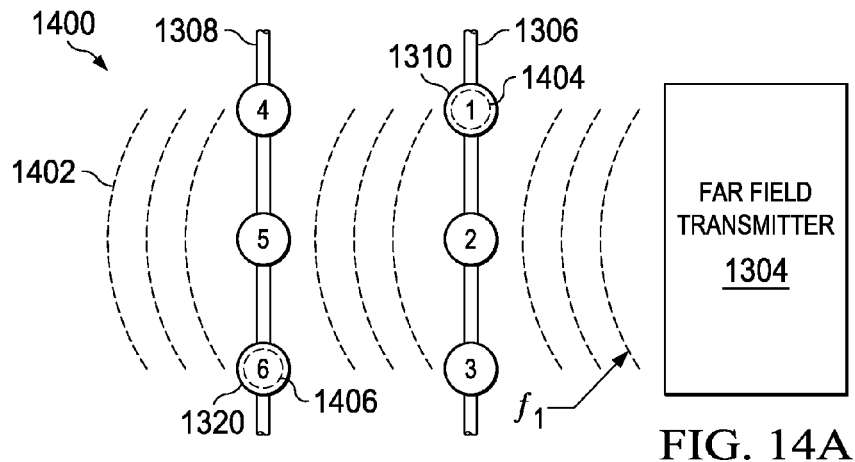
FIGS. 14A-14C are various IMD charging protocols, according to various embodiments.

FIG. 14A shows a first illustration 1400 of one or more IMDs being charged, according to one embodiment. First illustration 1400 includes first nerve 1306, second nerve 1308, far field transmitter 1304, first IMD 1310, second IMD 1312, third IMD 1314, fourth IMD 1316, fifth IMD 1318, sixth IMD 1320, and a first far field radiative signal 1402.

In this example, far field transmitter 1304 transmits the first far field radiative signal 1402 which radiates to the first IMD 1310, the second IMD 1312, the third IMD 1314, the fourth IMD 1316, the fifth IMD 1318, and the sixth IMD 1320. The first far field radiative signal 1402 is at a first frequency f1. Based on a frequency match, the first IMD 1310 and the sixth IMD 1320 are being charged (which is represented by reference numbers 1404 and 1406 respectfully) by the first far field radiative signal 1402. Further, based on a frequency mismatch (e.g., no frequency matching), the second IMD 1312, the third IMD 1314, the fourth IMD 1316, and the fifth IMD 1318 are not being charged by the first far field radiative signal 1402.

Figure 14B:
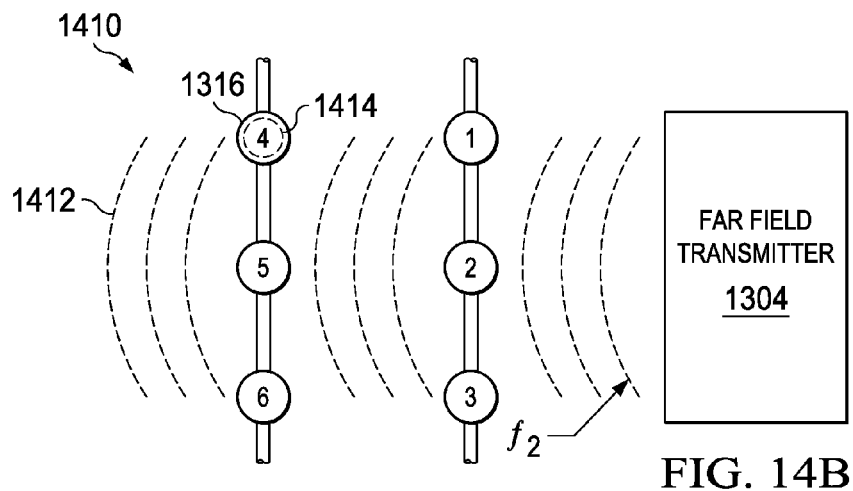

FIG. 14B shows a second illustration 1410 of one or more IMDs being charged, according to one embodiment. The second illustration 1410 includes the first nerve 1306, the second nerve 1308, the far field transmitter 1304, the first IMD 1310, the second IMD 1312, the third IMD 1314, the fourth IMD 1316, the fifth IMD 1318, the sixth IMD 1320, and a second far field radiative signal 1412.

In this example, the far field transmitter 1304 transmits the second far field radiative signal 1412 which radiates to the first IMD 1310, the second IMD 1312, the third IMD 1314, the fourth IMD 1316, the fifth IMD 1318, and the sixth IMD 1320. The second far field radiative signal 1412 is at a second frequency f2. Based on a frequency match, the fourth IMD 1316 is being charged (which is represented by reference number 1414) by the second far field radiative signal 1412. Further, based on a frequency mismatch (e.g., no frequency matching), the first IMD 1310, the second IMD 1312, the third IMD 1314, the fifth IMD 1318, and the sixth IMD 1320 are not being charged by the second far field radiative signal 1412.

Figure 14C:
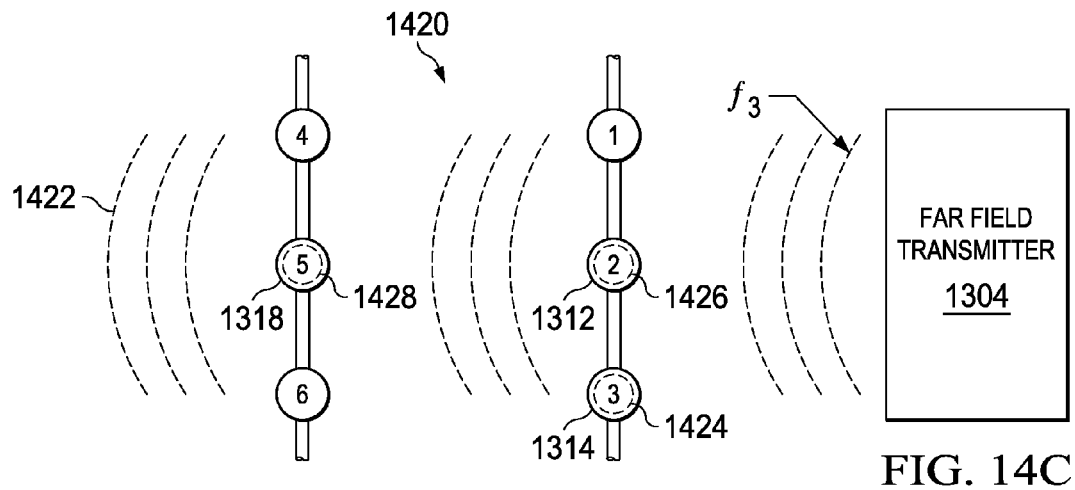

FIG. 14C shows a third illustration 1420 of one or more IMDs being charged, according to one embodiment. The third illustration 1420 includes the first nerve 1306, the second nerve 1308, the far field transmitter 1304, the first IMD 1310, the second IMD 1312, the third IMD 1314, the fourth IMD 1316, the fifth IMD 1318, the sixth IMD 1320, and a third far field radiative signal 1422.

In this example, the far field transmitter 1304 transmits the third far field radiative signal 1422 which radiates to the first IMD 1310, the second IMD 1312, the third IMD 1314, the fourth IMD 1316, the fifth IMD 1318, and the sixth IMD 1320. The third far field radiative signal 422 is at a third frequency f3. Based on a frequency match, the second IMD 1312, the third IMD 1314, and the fifth IMD 1318 are being charged (which is represented by reference numbers 1424, 1426, and 1428 respectfully) by the third far field radiative signal 1422. Further, based on a frequency mismatch (e.g., no frequency matching), the first IMD 1310, the fourth IMD 1316, and the sixth IMD 1320 are not being charged by the third far field radiative signal 1422.

In another example, the first IMD 1310 may be charged by a far field radiative signal with a first frequency f1 (e.g., 900 MHz). In this example, the first IMD 1310 would not be charged by a far field radiative signal with a second frequency f2 (e.g., 2.4 GHz). Further, the second IMD 1312 may be charged by a far field radiative signal with the second frequency f2 (e.g., 2.4 GHZ) but the second IMD 1312 is not charged by a far field radiative signal with the first frequency f1 (e.g., 900 MHz).

The IMDs (e.g., the first IMD 1310, the second IMD 1312, the third IMD 1314, the fourth IMD 1316, the fifth IMD 1318, the sixth IMD 1320, etc.) may be charged by one or more far field radiative signals (e.g., 1 to N) with one or more predetermined frequencies (e.g., 1 to N). For example, the third IMD 1314 may be charged by a far field radiative signal with a first frequency (e.g., 900 MHz) and/or a second frequency (e.g., 2.4 GHz). In this example, third IMD 1314 may not be charged by a far field radiative signal with any other frequency (e.g., 950 MHz, 2.1 GHz, 2.2 GHz, etc.). Further, the fourth IMD 1316 may be charged by a far field radiative signal with a third frequency (e.g., 950 MHz) and/or a fourth frequency (e.g., 2.1 GHz). In this example, the fourth IMD 1316 may not be charged by a far field radiative signal with any other frequency (e.g., 900 MHz, 2.2 GHz, 2.4 GHz, etc.). Further, in this example, the fifth IMD 1318 may be charged by a far field radiative signal with the first frequency (e.g., 900 MHz), the third frequency (e.g., 950 MHz), and a fifth frequency (e.g., 2.2 GHz).

In one example, a signal may be sent to wake up (e.g., turn on) one or more antennas at one or more frequencies and then one or more far field radiative signals may be transmitted to charge the devices (e.g., IMDs) connected to the one or more antennas.

Figure 15A:
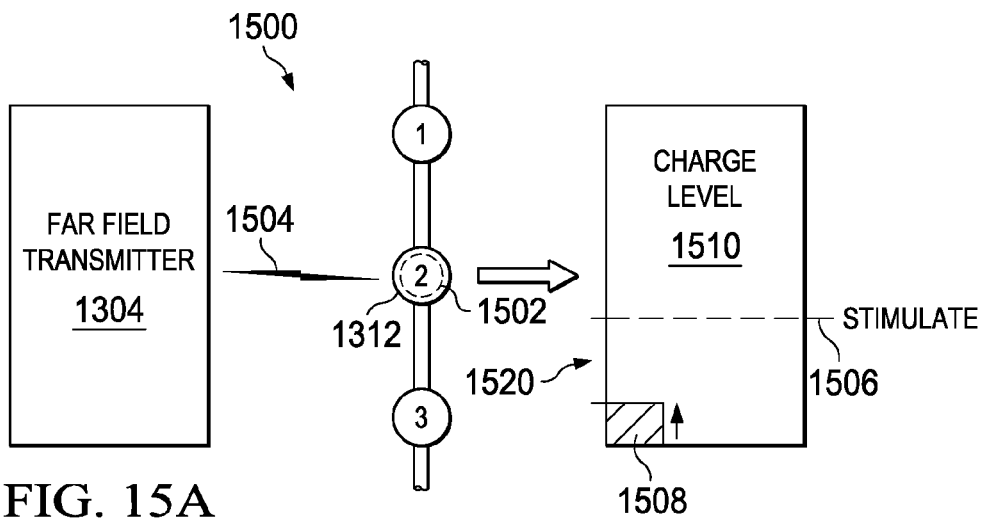
FIGS. 15A-15E are various stages for one or more IMD charging procedures, according to various embodiments.

FIG. 15A shows a first illustration 1500 of one IMD being charged, according to one embodiment. The first illustration 1500 includes the first nerve 1306, the far field transmitter 1304, the first IMD 1310, the second IMD 1312, the third IMD 1314, a first far field radiative signal 1504, and a charge level indicator 1510. In this example, the first far field radiative 1504 is at a first frequency. In this example, the first far field radiative signal 1504 is charging the second IMD 1312 (which is represented by reference number 1502). The first far field radiative signal 1504 powers the second IMD 1312 based on a frequency match. Further, based on a frequency mismatch (e.g., no frequency matching), the first IMD 1310 and the third IMD 1314 are not being charged by the first far field radiative signal 1504.

In this example, the charging process is represented by a first charge unit 1508 shown on the charge level indicator 1510. The first charge unit 1508 may not be enough charge to deliver a stimulation from the second IMD 1312. A stimulation threshold 1506 may represent the amount of charge required 1312 to deliver the appropriate stimulation from the second IMD 1312 to one or more nerves or structures (or deliver a therapy, sense, deliver a drug etc.). A delta charge requirement 1520 may represent the amount of charge still needed to be able to reach the stimulation threshold 1506. In another example, one or more first far field radiative signals may be able to charge one or more devices (e.g., one or more IMDs) to provide one or more stimulations.

Figure 15B:
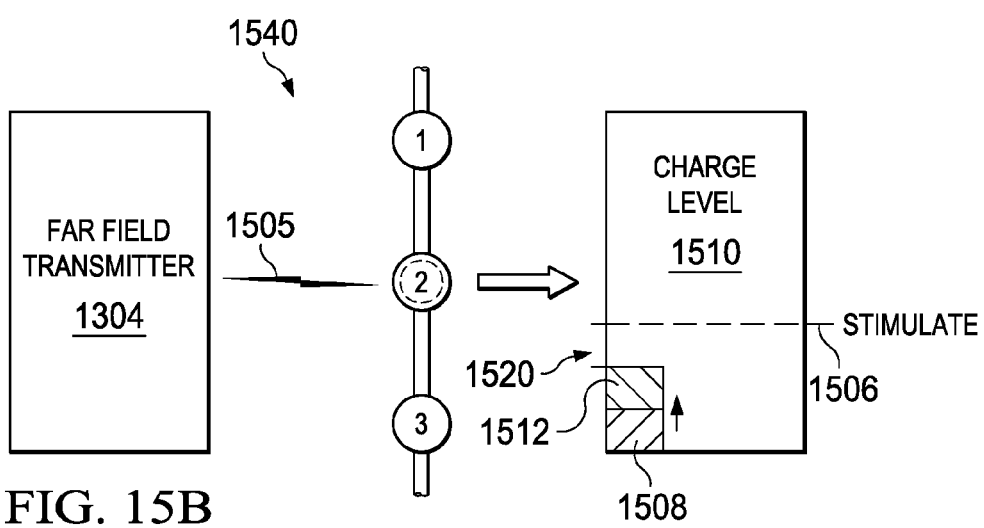

FIG. 15B shows a second illustration 1540 of one IMD being charged, according to one embodiment. The second illustration 1540 includes the first nerve 1306, the far field transmitter 1304, the first IMD 1310, the second IMD 1312, the third IMD 1314, a second far field radiative signal 1505, and the charge level indicator 1510. In this example, the second far field radiative signal 1505 is at the first frequency. In this example, the second far field radiative signal 1505 is charging the second IMD 1312 (which is represented by reference number 1502). The second far field radiative signal 1505 powers the second IMD 1312 based on a frequency match. Further, based on a frequency mismatch (e.g., no frequency matching), the first IMD 1310 and the third IMD 1314 are not being charged by the second far field radiative signal 1505.

In this example, the charging process is represented by the first charge unit 1508 and a second charge unit 1512 shown on the charge level indicator 1510. The first charge unit 1508 and the second charge unit 1512 may not be enough charge to deliver a stimulation from the second IMD 1312. The stimulation threshold 1506 may represent the amount of charge required to deliver the appropriate stimulation from the second IMD 1312 to one or more nerves or structures (or deliver a therapy, sense, deliver a drug etc.). The delta charge requirement 1520 may represent the amount of charge still needed to be able to reach the stimulation threshold 1506 which would allow the second IMD 1312 to deliver stimulation.

Figure 15C:
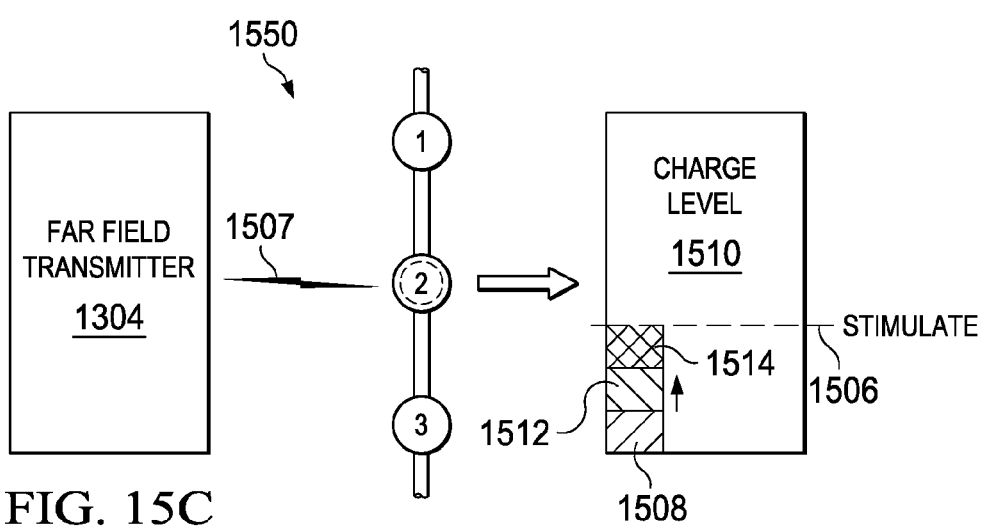

FIG. 15C shows a third illustration 1550 of one IMD being charged, according to one embodiment. The third illustration 1550 includes the first nerve 1306, the far field transmitter 1304, the first IMD 1310, the second IMD 1312, the third IMD 1314, a third far field radiative signal 1507, and the charge level indicator 1510. In this example, the third far field radiative signal 1507 is at the first frequency. In this example, the third far field radiative signal 1507 is charging the second IMD 1312 (which is represented by reference number 1502). The third far field radiative signal 1507 powers the second IMD 1312 based on a frequency match. Further, based on a frequency mismatch (e.g., no frequency matching), the first IMD 1310 and the third IMD 1314 are not being charged by the third far field radiative signal 1507. The second IMD 1312 (and/or any IMD) may be able to be charged by more than one frequency and/or more than one frequency band.

In this example, the charging process is represented by the first charge unit 1508, the second charge unit 1512, and a third charge unit 1514 shown on the charge level indicator 1510. The first charge unit 1508, the second charge unit 1512, and the third charge unit 1514 may be enough charge to deliver a stimulation from the second IMD 1312. The stimulation threshold 1506 may represent the amount of charge required to deliver the appropriate stimulation from the second IMD 1312 to one or more nerves. The delta charge requirement 1520 may represent the amount of charge still needed to be able to reach the stimulation threshold 1506 which would allow the second IMD 1312 to deliver stimulation. In this example, the delta charge requirement 1520 is zero. In another example, a single far field radiative signal may be able to charge one or more devices (e.g., one or more IMDs) to provide one or more stimulations. In some embodiments, the IMD may deliver a stimulation when the stimulation threshold 1506 is reached. The stimulation threshold 1506 may correspond to sufficient charge to deliver a single stimulation, more than one stimulation, or a therapy over a certain period of time. Once the stimulation threshold 1506 is reached, the stimulation or therapy may begin. In some embodiments, a code or activation may be required to charge and/or to stimulate.

Figure 15D:
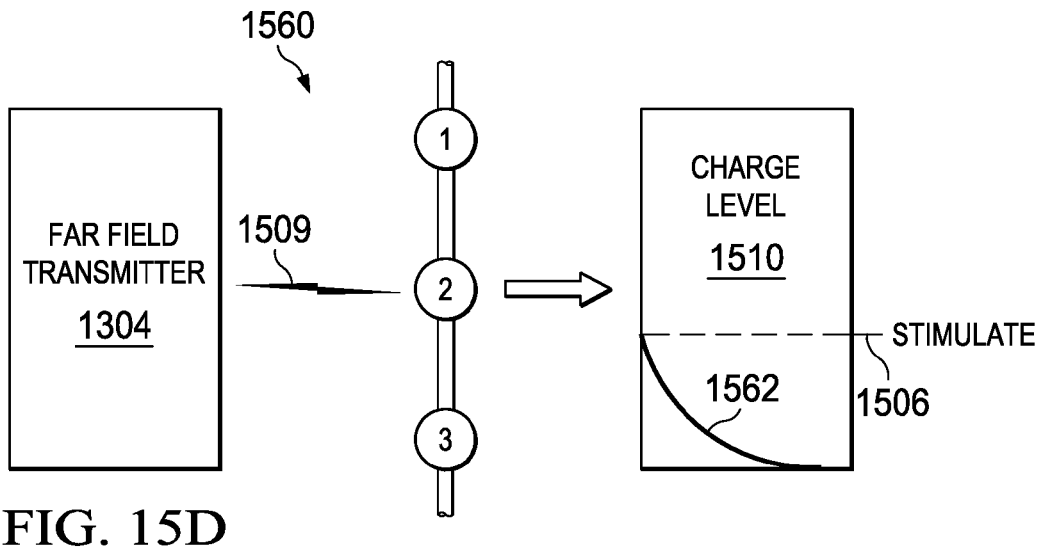

FIG. 15D shows a fourth illustration 1560 of one IMD being charged, according to one embodiment. The fourth illustration 1500 includes the first nerve 1306, the far field transmitter 1304, the first IMD 1310, the second IMD 1312, the third IMD 1314, an Nth far field radiative signal 1509, and charge level indicator 1510. In this example, the second IMD 1312 is discharging the stored energy in the second IMD 1312 to provide one or more stimulations. The second IMD 1312 is discharging as illustrated by a discharging pattern 1562.

Figure 15E:
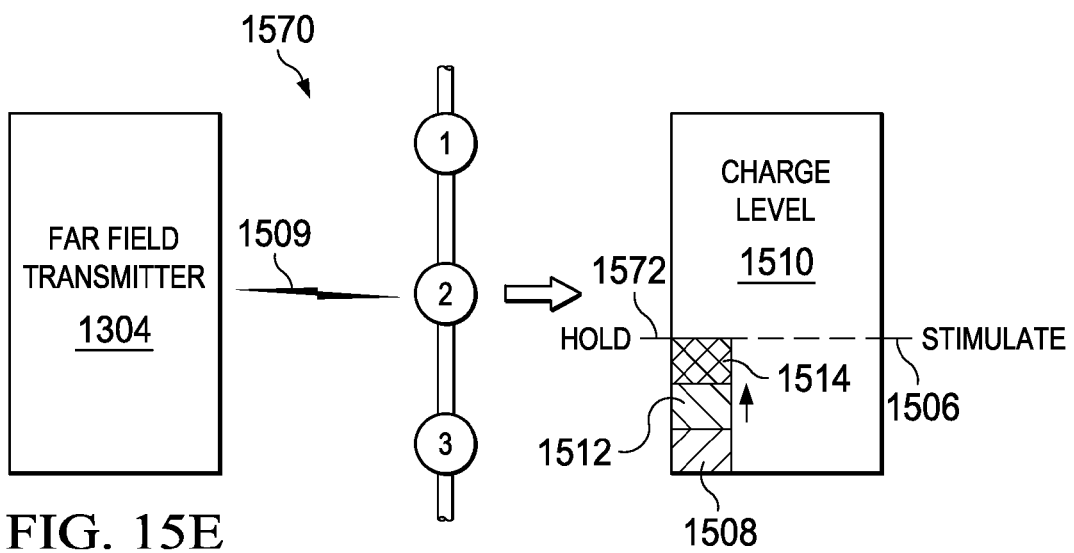

FIG. 15E shows a fifth illustration 1570 of one IMD being charged, according to one embodiment. Fifth illustration 1570 includes the first nerve 1306, the far field transmitter 1304, the first IMD 1310, the second IMD 1312, the third IMD 1314, the Nth far field radiative signal 1509, and the charge level indicator 1510. In this example, the charge stored in the second IMD 1312 is held 1572 waiting for instructions to discharge and provide one or more stimulations. These instructions (e.g., discharge code, stimulation code, sequence code, treatment protocol code, etc.) to discharge the charge held 1572 in the second IMD 1312 may be transmitted by an IMD, an external control device, an external device, and/or any other mechanism. These instructions may be based on a treatment schedule and/or treatment protocol. In some embodiments, a code may be sent to the IMD to initiate charging so that the device won't charge until the code is received (e.g., charge initiation code). The charge initiation code may need to be provided prior to each recharge, prior to an initial charge, prior to a treatment period, prior to a sequence of charges, for any other charging protocol, or in any other manner to control the charging of one or more of the IMDs. In some embodiments, a code may be sent to initiate a stimulation or a therapy (e.g., therapy initiation code). A therapy may comprise one or more stimulations, one or more drug doses, or delivery of therapy over a time period. The therapy initiation code may be used prior to each therapy delivery, therapy delivery period, an initial therapy use, or in any other manner to control the delivery of a therapy using one or more of the IMDs. The charge initiation code and the therapy initiation code may be delivered at the same frequency as the charging signal, or at any other frequency. The IMD may be programed to recognize the particular code or code pattern. In another example, the stimulations from one or more IMDs may be utilized to warm up, or condition a nerve before a primary stimulation occurs. In another example, the instructions may be sent from an external device (e.g., patient interface device, smart phone, mobile device, computing device, control device, etc.). The instructions may first be a charging signal and then a stimulation signal to initiate a stimulation or therapy. In another example, the stimulation treatment may be utilized in combination with a drug delivery system. In this example, the charging of the one or more electronic devices may also release one or more drugs into the patient. For example, to maintain a blood level concentration of X in a patient, the drug delivery system may utilize one or more far field radiative signals to enable an electrical device to deliver one or more drugs. Further, this method may be implemented with a feedback loop that utilizes a blood concentration measurement mechanism to determine one or more blood concentration levels, which can then be utilized to maintain one or more blood concentration levels within a predetermined range.

Figure 16A:
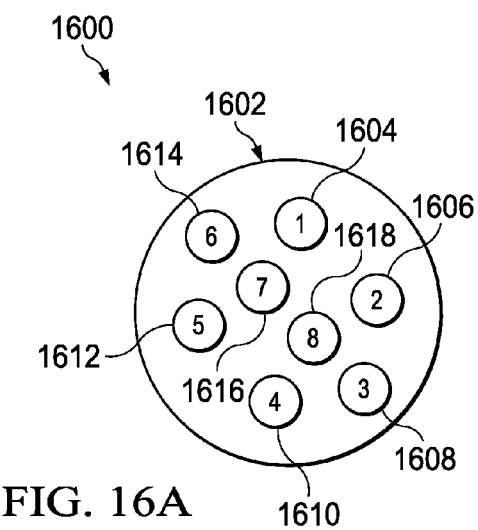
FIGS. 16A-16E are various examples of charging different nerve elements utilizing one or more IMDs, according to various embodiments.

FIG. 16A shows a nerve 1600 with one or more nerve elements (e.g., nerve fibers or axons, groups of nerve fibers or axons, etc.). In this example, nerve 1600 may include a first nerve element 1604, a second nerve element 1606, a third nerve element 1608, a fourth nerve element 1610, a fifth nerve element 1612, a sixth nerve element 1614, a seventh nerve element 1616, an eighth nerve element 1618, and a nerve exterior 1602. In one example, one or more IMDs may not be able to stimulate or recruit every nerve element, especially those located near the center of the nerve because the stimulation may only penetrate to a certain depth. In one example, as nerve 1600 travels through the body, the various nerve elements may reorder, or change positions, so that one nerve element in the center of the nerve at one location may be near the outside edge of the nerve at a different location on the nerve where it may be easier to recruit or stimulate. The first nerve element 1604, second nerve element 1606, third nerve element 1608, fourth nerve element 1610, fifth nerve element 1612, sixth nerve element 1614, seventh nerve element 1616, and eighth nerve element 1618 may change positions, which may increase the likelihood of stimulation of different nerve elements by one or more IMDs when the one or more IMDs are placed at different locations on the nerve, including nerve branches.

Figure 16B:
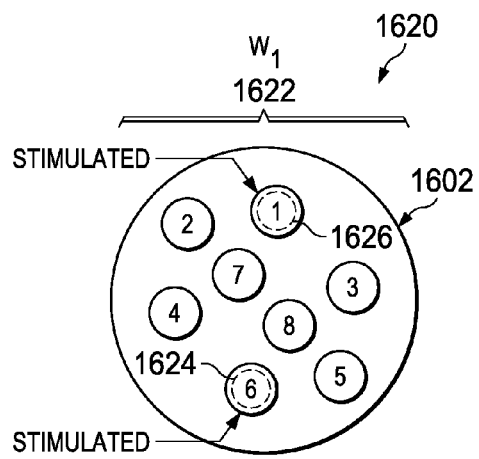

FIG. 16B shows a first illustration 1620 of a first IMD at a first location on a nerve, according to one embodiment. First illustration 1620 shows a first IMD 1622 stimulating (which is represented by reference numbers 1626 and 1624, respectfully) first nerve element 1604 and sixth nerve element 1614 in nerve 1600. In this example, first IMD 1622 may not be able to stimulate second nerve element 1606, third nerve element 1608, fourth nerve element 1610, fifth nerve element 1612, seventh nerve element 1616, and eighth nerve element 1618.

Figure 16C:
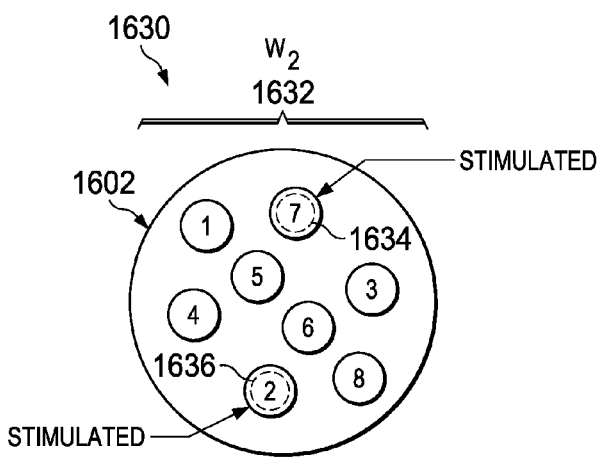

FIG. 16C shows a second illustration 1630 of a second IMD at a second location on the nerve, according to one embodiment. Second illustration 1630 shows a second IMD 1634 stimulating (which is represented by reference numbers 1636 and 1634, respectfully) seventh nerve element 1634 and second nerve element 1636 in nerve 1600. In this example, second IMD 1634 may not be able to stimulate first nerve element 1604, third nerve element 1608, fourth nerve element 1610, fifth nerve element 1612, sixth nerve element 1614, and eighth nerve element 1618.

Figure 16D:
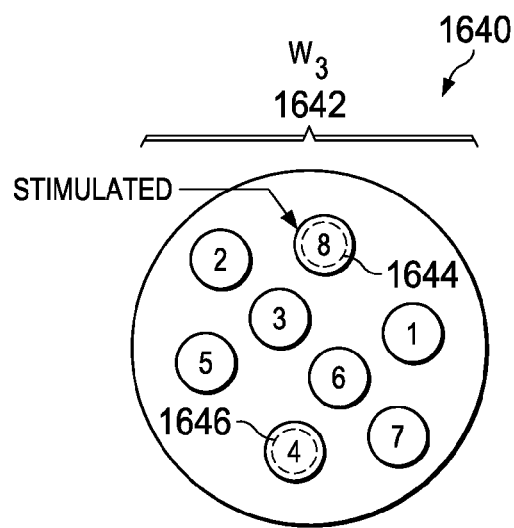

FIG. 16D shows a third illustration 1640 of a third IMD at a third location on a nerve, according to one embodiment. Third illustration 1640 shows a third IMD 1642 stimulating (which is represented by reference numbers 1644 and 1646, respectfully) eighth nerve element 1644 and fourth nerve element 1646 in nerve 1600. In this example, third IMD 1644 may not be able to stimulate first nerve element 1604, second nerve element 1606, third nerve element 1608, fifth nerve element 1612, sixth nerve element 1614, and seventh nerve element 1616. FIGS. 16A-16D illustrate how nerve fibers or groups of nerve fibers may migrate or change position along the nerve. At some locations a nerve fiber may be located at the center of the nerve, which may be difficult to stimulate, and at other locations the nerve fiber may be located close to the outside edge of the nerve and may be relatively easy to stimulate. Therefore, positioning IMDs along the nerve at different locations may increase recruitment or stimulation of nerve fibers, which may increase the therapeutic effect of stimulation.

Figure 16E:
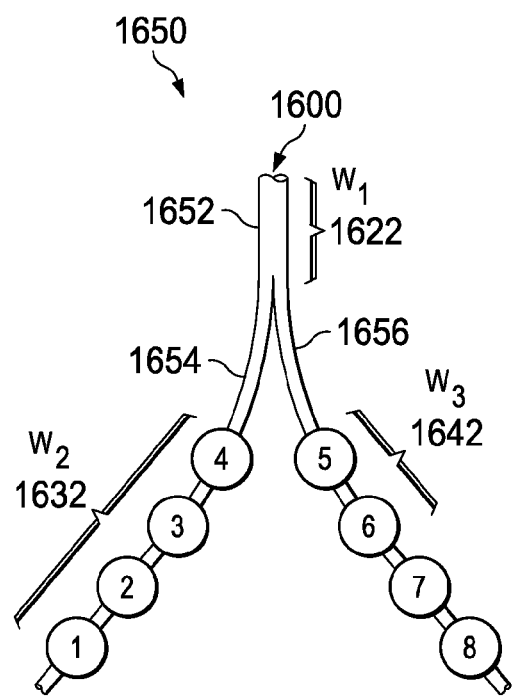

FIG. 16E shows a fifth illustration 1650 of numerous IMDs at various locations stimulating one or more nerves, according to one embodiment. Fifth illustration 1650 shows a first IMD 1622 stimulating a first nerve area 1652 of nerve 1600. In this example, one or more of first nerve element 1604, second nerve element 1606, third nerve element 1608, fourth nerve element 1610, fifth nerve element 1612, sixth nerve element 1614, seventh nerve element 1616, and/or eighth nerve element 1618 may be stimulated by first IMD 1622.

In another example, nerve 1600 may branch out into one or more secondary nerve branches, such as, a first nerve branch 1654 and a second nerve branch 1656, each branch having a smaller diameter than the nerve before the branch. The nerve elements in nerve 1600 may split off where first nerve element 1604, second nerve element 1606, third nerve element 1608, and fourth nerve element 1610 going into first nerve branch 1654 and, fifth nerve element 1612, sixth nerve element 1614, seventh nerve element 1616, and eighth nerve element 1618 going into second nerve branch 1656. A second IMD 1632 located on first nerve branch 1654 may stimulate first nerve element 1604, second nerve element 1606, third nerve element 1608, and fourth nerve element 1610. A third IMD 1642 located on second nerve branch 1656 may stimulate fifth nerve element 1612, sixth nerve element 1614, seventh nerve element 1616, and eighth nerve element 1618. In these examples, one or more of the nerve elements that could not be stimulated in first nerve area 1652 may now be able to be stimulated in first nerve branch 1654 and/or second nerve branch 1656. Nerve branches have a smaller diameter than its corresponding trunk and as a result, more recruitment as a percentage of nerve fibers may be achievable in the branches for a given stimulation penetration depth. Stimulating at one or more locations on the trunk and one or more locations on one or more branches may further increase recruitment of nerve fibers and increase the therapeutic effect of stimulation.

Figure 17A:
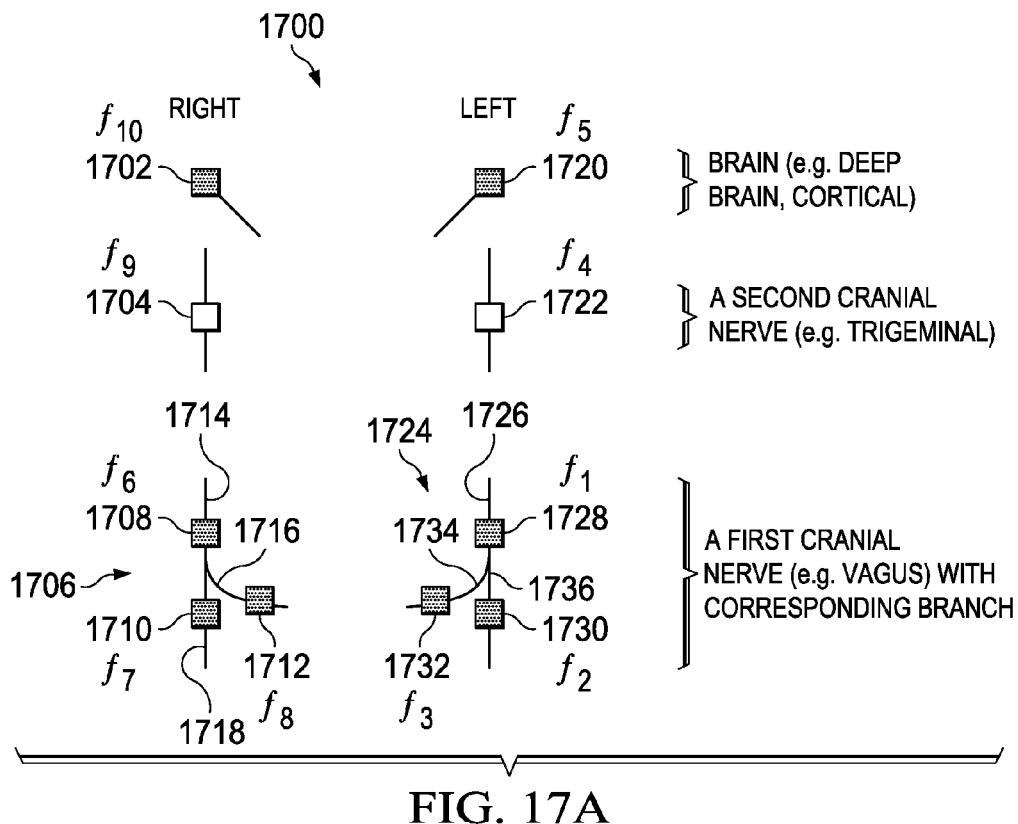
FIGS. 17A-17E are various configurations of IMDs, according to various embodiments.

In FIG. 17A, various configurations of IMDs are shown, according to various embodiments. A first diagram 1700 includes a first IMD layout 1702, a second IMD layout 1704, a third IMD layout 1706, a fourth IMD layout 1720, a fifth IMD layout 1722, and a sixth IMD layout 1724.

First IMD layout 1702 may be utilized in a brain electrode system (e.g., deep brain, cortical). First IMD layout 1702 may charge at a tenth frequency f10 (e.g., 1 GHz) and may be positioned on the right side of the targeted area (e.g., right hemisphere of the brain, right cranial nerve, etc.). First IMD layout 1702 may be utilized in combination with fourth IMD layout 1720. Fourth IMD layout 1720 may charge at a fifth frequency f5 (e.g., 960 MHz) and may be positioned on the left side of the targeted area (e.g., left hemisphere of the brain, left cranial nerve, etc.).

Second IMD layout 1704 may be utilized in a second cranial nerve system (e.g., trigeminal nerve). Second IMD layout 1704 may charge at a ninth frequency f9 (e.g., 2.4 GHz) and may be positioned on the right side of the targeted area (e.g., right cranial nerve, other nerve or structure on right side of the patient's body). Second IMD layout 1704 may be utilized in combination with fifth IMD layout 1722. Fifth IMD layout 722 may charge at a fourth frequency f4 (e.g., 900 MHz) and may be positioned on the left side of the target area (e.g., left cranial nerve, other nerve or structure on left side of the patient's body).

Third IMD layout 1706 may be utilized in a first cranial nerve system with corresponding branches (e.g., vagus nerve). Third IMD layout 1706 may have one or more IMDs. For example, the third IMD layout 1706 may include three IMDs (e.g., a first IMD 1708, a second IMD 1710, and a third IMD 1712) with one IMD located on each of a first nerve 1714, a first branch 1716, and a second branch 1718. First IMD 1708 may be charged by a sixth frequency f6. Second IMD 1710 may be charged by a seventh frequency f7. Third IMD 1712 may be charged by an eighth frequency f8. Third IMD layout 1706 may be positioned on the right side of the targeted area (e.g., right cranial nerve, other nerve or structure on right side of the patient's body). Third IMD layout 1706 may be utilized in combination with sixth IMD layout 1724. Sixth IMD layout 1724 may be positioned on the left side of the targeted area (e.g., left cranial nerve, other nerve or structure on left side of the patient's body). Sixth IMD layout 1724 may have one or more IMDs. For example, the sixth IMD layout 1724 may include three IMDs (e.g., a fourth IMD 1728, a fifth IMD 1730, and a sixth IMD 1732) with on IMD located on a second nerve 1726, a third branch 1734, and a fourth branch 1736. Fourth IMD 1728 may be charged by a first frequency f1. Fifth IMD 1730 may be charged by a second frequency f2. Sixth IMD 1732 may be charged at a third frequency f3. In some embodiments, first frequency f1 through tenth frequency f11 may each be a different frequency, In some embodiments, each of the ten charging frequencies (f1-f10) may be different frequencies, at least two of the charging frequencies may be the same frequencies (e.g., the first frequency f1 and the second frequency may be the same frequency f2), at least three of the charging frequencies may be the same, at least four of the frequencies may be the same frequency, at least five of the frequencies may be the same frequency, at least six of the frequencies may be the same frequency, at least seven of the frequencies may be the same frequency, at least eight of the frequencies may be the same frequency, at least nine of the frequencies may be the same frequency, or all ten of the frequencies may be the same frequency.

Figure 17B:
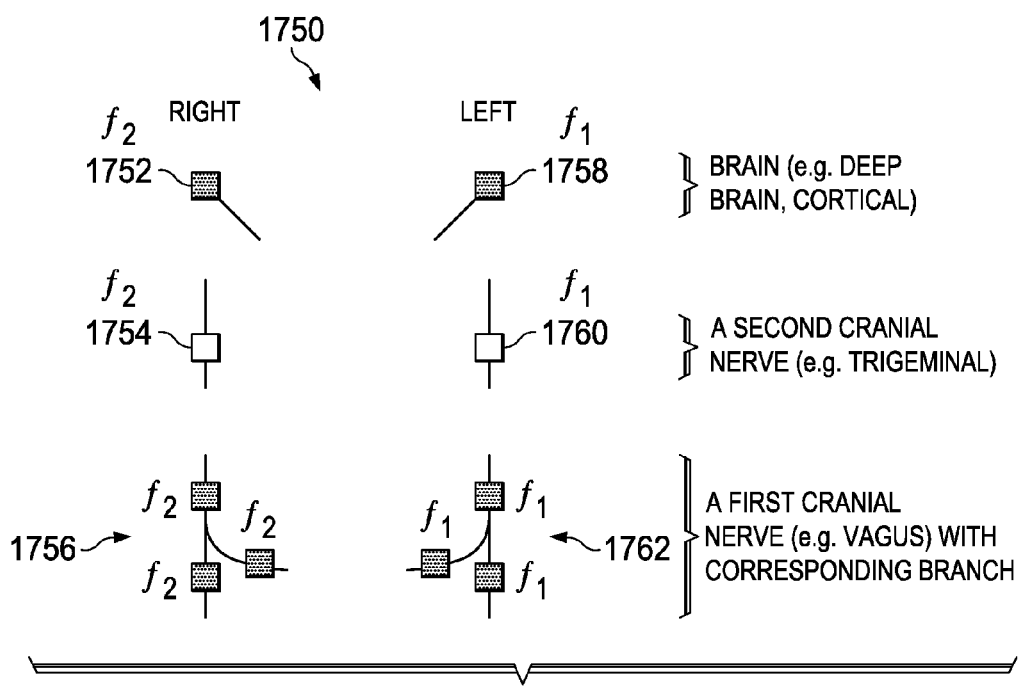

In FIG. 17B, various configurations of IMDs are shown, according to various embodiments. A second diagram 1750 includes a seventh IMD layout 1752, an eighth IMD layout 1754, a ninth IMD layout 1756, a tenth IMD layout 1758, an eleventh IMD layout 1760, and a twelfth IMD layout 1762.

Seventh IMD layout 1752 may be utilized in combination with tenth IMD layout 1758 to provide brain stimulation via electrodes located in or on the brain. Seventh IMD layout 1752 may utilize at least one IMD located on the right side of the target area (e.g., right hemisphere of the brain, right cranial nerve, etc.), which may be charged at a second frequency f2. Tenth IMD layout 1758 may utilize at least one IMD located on the left side of the target area (e.g., left hemisphere of the brain, left cranial nerve, etc.), which may be charged at a first frequency f1.

Eighth IMD layout 1754 may be utilized in combination with eleventh IMD layout 1760 to provide stimulation via one or more electrodes to a second cranial nerve area (e.g., trigeminal nerve). Eighth IMD layout 1754 may utilize at least one IMD located on the right side of the target area (e.g., right cranial nerve, other nerve or structure on right side of the patient's body), which may be charged at a second frequency f2. Eleventh IMD layout 1760 may utilize at least one IMD located on the left side of the target area (e.g., left cranial nerve, other nerve or structure on left side of the patient's body), which may be charged at a first frequency f1.

Ninth IMD layout 1756 may be utilized in combination with twelfth IMD layout 1762 to provide stimulation to a first cranial nerve area with corresponding branches (e.g., vagus nerve). Ninth IMD layout 1756 may utilize one or more (in this example three IMDs) IMDs located at various locations on the right primary nerve and the right nerve branches (e.g., right cranial nerve, other nerve or structure on right side of the patient's body). Twelfth IMD 1762 may utilize one or more (in this example three IMDs) IMDs located at various locations on the left primary nerve and the left nerve branches (e.g., left cranial nerve, other nerve or structure on left side of the patient's body). In some embodiments, the IMDs on the left side of the patient's body may be charged at the first frequency f1 and the IMDs on the right side of the patient's body may be charged at the second frequency f2.

Figure 17C:
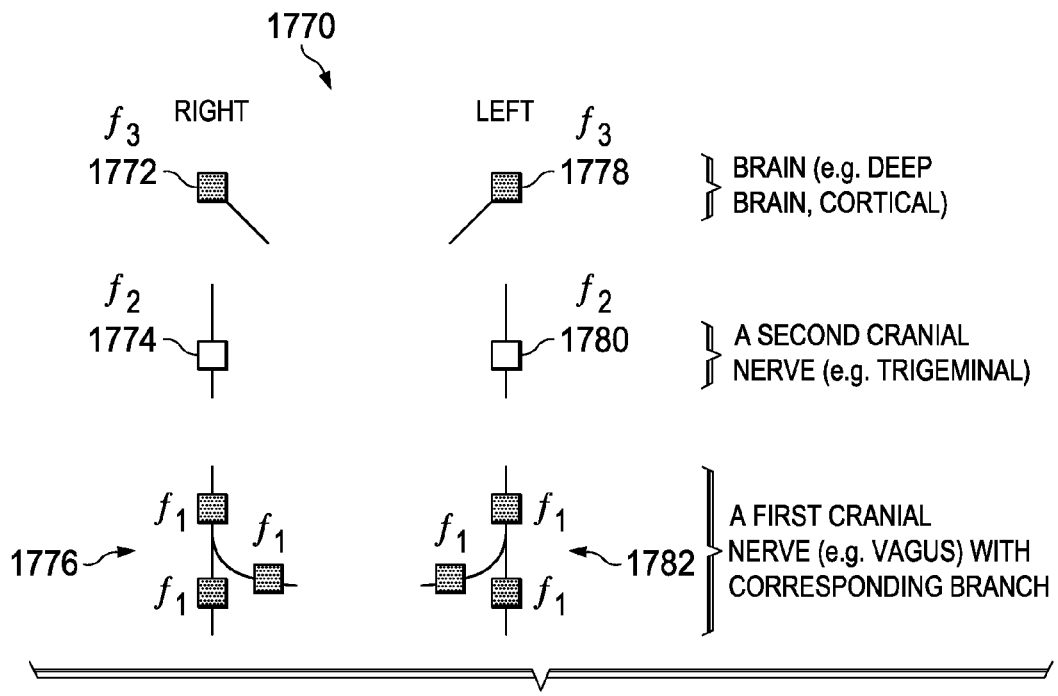

In FIG. 17C, various configurations of IMDs are shown, according to various embodiments. A third diagram 1770 includes a thirteenth IMD layout 1772, a fourteenth IMD layout 1774, a fifteenth IMD layout 1776, a sixteenth IMD layout 1778, a seventeenth IMD layout 1780, and an eighteenth IMD layout 1782.

Thirteenth IMD layout 1772 may be utilized in combination with sixteenth IMD layout 1778 to provide brain stimulation via electrodes located in or on the brain at a third frequency f3. Fourteenth IMD layout 1774 may be utilized in combination with seventeenth IMD layout 1780 to provide stimulation via one or more electrodes to a second cranial nerve area (e.g., trigeminal nerve) at a second frequency f2. Fifteenth IMD layout 1776 may be utilized in combination with eighteenth IMD layout 1782 to provide stimulation to a first cranial nerve area with corresponding branches (e.g., vagus nerve) at a first frequency f1. In some embodiments, the charging frequency may be based target structure. For example, IMDs located at the left and right vagus nerve (and/or one or more corresponding branches) may be charged at a first frequency f1, IMDs located at the left and right trigeminal nerve (and/or one or more corresponding branches) may be charge at a second frequency f2, and IMDs located in or on the left and right hemispheres of the brain may be charged at a third frequency f3.

Figure 17D:
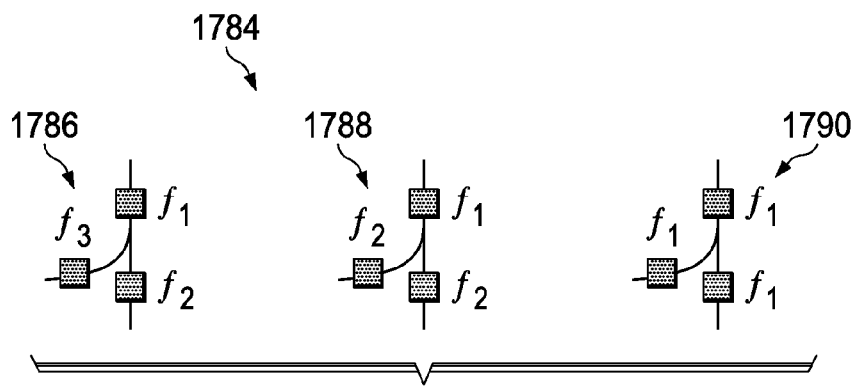

In FIG. 17D, various configurations of IMDs are shown, according to various embodiments. A fourth diagram 1784 includes a nineteenth IMD layout 1786, a twentieth IMD layout 1788, and a twenty-first IMD layout 1790.

Nineteenth IMD layout 1786 may utilize three IMDs that are charged at three different frequencies (e.g., a first frequency f1, a second frequency f2, and a third frequency f3). Twentieth IMD layout 1788 may utilize three IMDs where two of the IMDs are charged at the same frequency (e.g., a second frequency f2) and one of the IMDs is charged at a different frequency (e.g., a first frequency f1). Twenty-first IMD layout 1790 may utilize three IMDs that are charged at the same frequency (e.g., a first frequency f1).

Figure 17E:
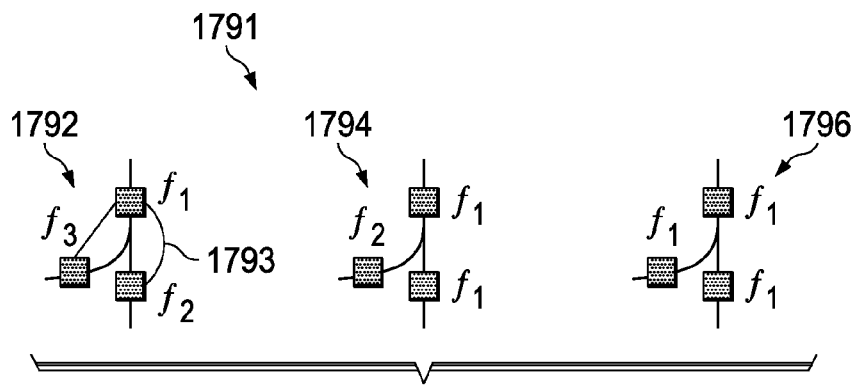

In FIG. 17E, various configurations of IMDs are shown, according to various embodiments. A fifth diagram 1791 includes a twenty-second IMD layout 1792, a twenty-third IMD layout 1794, and a twenty-fourth IMD layout 1796.

Twenty-second IMD layout 1792 may utilize three IMDs that are charged at three different frequencies (e.g., a first frequency f1, a second frequency f2, and a third frequency f3). Further, the IMDs may be connected to one or more secondary branches 1793. Twenty-third IMD layout 1794 may utilize three IMDs where two of the IMDs are charged at the same frequency (e.g., a first frequency f1) and one of the IMDs is charged at a different frequency (e.g., a second frequency f2). Twenty-fourth IMD layout 1796 may utilize three IMDs that are charged at the same frequency (e.g., a first frequency f1).

In the various examples shown in FIGS. 17A-17E, one or more IMDs may be utilized in any of the IMD layouts. Further, one or more IMDs may be charged at one or more frequencies. In addition, one or more IMDs may provide stimulation in any of the treatment protocols and/or by any other method described in this disclosure.

Figure 18A:
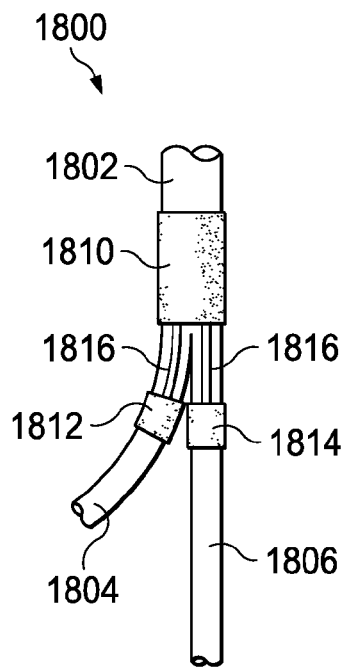
FIGS. 18A-18C are various examples of IMDs, according to various embodiments.

In FIG. 18A, a first IMD electrical configuration 1800 is shown, according to one embodiment. First IMD electrical configuration 1800 includes a primary IMD 1810 on a primary nerve 1802 connected via one or more electrical leads 1816 to a first IMD 1812 on a first nerve branch 1804 and to a second IMD 1814 on a second nerve branch 1806. The primary IMD 1810 may include electronics to control stimulation at the first IMD 1812 and the second IMD 1814. Each IMD may be charged at the same frequency of different frequencies. One antenna may be used by the three IMDs or multiple antennas may be located at the primary IMD 1810 and/or distributed amongst the three IMDs.

Figure 18B:
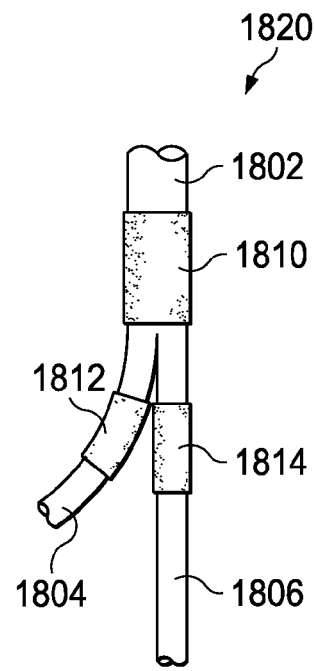

In FIG. 18B, a second IMD electrical configuration 1820 is shown, according to one embodiment. Second IMD electrical configuration 1820 includes primary IMD 1810 on primary nerve 1802 connected wirelessly to first IMD 1812 on first nerve branch 1804 and to second IMD 1814 on second nerve branch 1806. In another example, second IMD electrical configuration 1820 includes primary IMD 1810 on primary nerve 1802 which is not connected wirelessly to first IMD 1812 on first nerve branch 1804 and to second IMD 1814 on second nerve branch 1806. The primary IMD 1810 may include electronics to control stimulation at the first IMD 1812 and the second IMD 1814. Each IMD may be charged at the same frequency of different frequencies. One antenna may be used by the three IMDs or multiple antennas may be located at the primary IMD 1810 and/or distributed amongst the three IMDs.

Figure 18C:
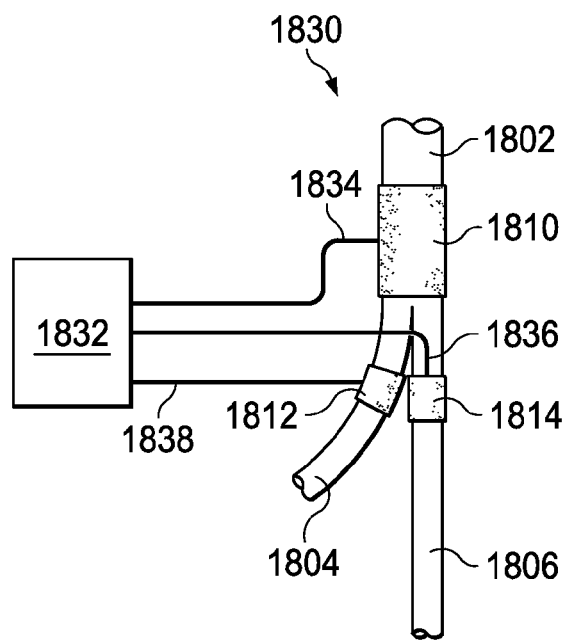

In FIG. 18C, a third IMD electrical configuration 1830 is shown, according to one embodiment. Third IMD electrical configuration 1830 includes primary IMD 1810 on primary nerve 1802, first IMD 1812 on first nerve branch 1804, and second IMD 1814 on second nerve branch 1806 connected via one or more electrical leads (e.g., a first lead 1834, a second lead 1836, and a third lead 1838) to a control device 1832. The control device 1834 may control stimulation at the primary IMD 1810, the first IMD 1812, and the second IMD 1814. Each IMD may be charged at the same frequency of different frequencies. One antenna may be used by the three IMDs or multiple antennas may be located at the primary IMD 1810 and/or distributed amongst the three IMDs.

Figure 19:
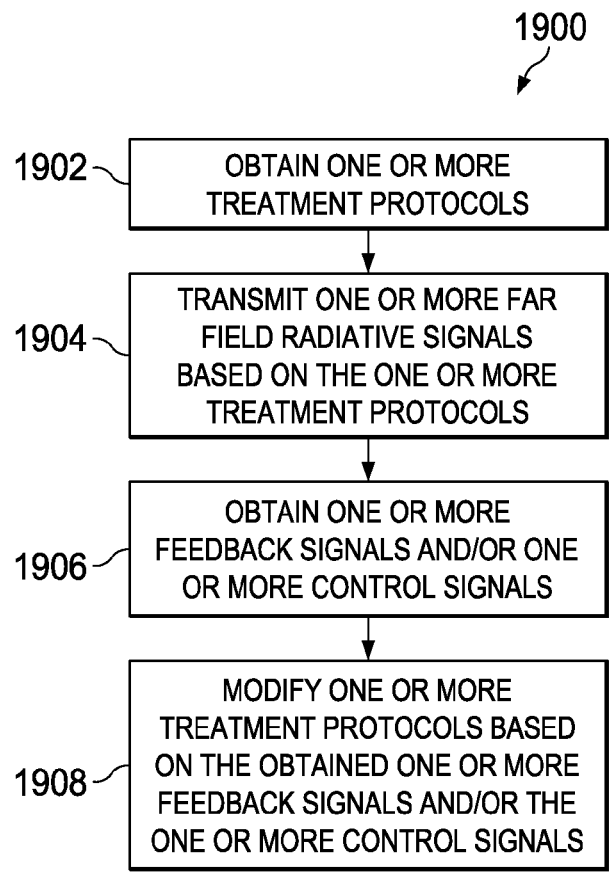
FIG. 19 is a flow diagram of a treatment protocol, according to one embodiment.

In FIG. 19, a first flow diagram 1900 is shown, according to one embodiment. The method may include obtaining one or more treatment protocols, at 1902. The method may include transmitting one or more far field radiative signals based on the one or more treatment protocols, at 1904. The method may also include obtaining one or more feedback signals and/or one or more control signals, at 1906. The method may also include modifying the one or more treatment protocols based on the obtained one or more feedback signals and/or the one or more control signals, at 1908.

For example, far field transmitter 1304 may transmit one or more far field radiative signals to charge one or more IMDs based on a first treatment protocol. After receiving one or more treatment feedback signals, far field transmitter 1304 may modify (e.g., change) which far field radiative signals are transmitted to modify (e.g., change) which IMDs are charged to modify (e.g., change) the treatment protocol. In another example, after receiving one or more treatment feedback signals, far field transmitter 1304 may not modify which far field radiative signals are transmitted. However, a control device may prohibit one or more IMDs from producing one or more stimulations. In some embodiments, the IMD may require a code to begin charging and/or to initiate a stimulation or therapy. In another example, after receiving one or more treatment feedback signals, far field transmitter 1304 may modify (e.g., change) which far field radiative signals are transmitted to modify (e.g., change) which IMDs are charged to modify (e.g., change) the treatment protocol. In this example, the control device may also prohibit one or more IMDs from producing one or more stimulations.

In another example, far field transmitter 1304 may transmit one or more far field radiative signals to charge one or more IMDs based on a first treatment protocol. After receiving one or more signals from one or more external devices, far field transmitter 1304 may modify (e.g., change) which far field radiative signals are transmitted to modify (e.g., change) which IMDs are charged to modify (e.g., change) the treatment protocol. In another example, after receiving one or more treatment feedback signals, far field transmitter 1304 may not modify which far field radiative signals are transmitted. However, a control device may prohibit one or more IMDs from producing one or more stimulations. In some embodiments, the IMD may require a code to begin charging and/or to initiate a stimulation or therapy. In another example, after receiving one or more treatment feedback signals, far field transmitter 1304 may modify (e.g., change) which far field radiative signals are transmitted to modify (e.g., change) which IMDs are charged to modify (e.g., change) the treatment protocol. In this example, the control device may also prohibit one or more IMDs from producing one or more stimulations.

In another example, far field transmitter 1304 may transmit one or more far field radiative signals to charge one or more IMDs based on a first treatment protocol. After receiving one or more patient inputs, far field transmitter 1304 may modify (e.g., change) which far field radiative signals are transmitted to modify (e.g., change) which IMDs are charged to modify (e.g., change) the treatment protocol. In another example, after receiving one or more treatment feedback signals, far field transmitter 1304 may not modify which far field radiative signals are transmitted. However, a control device may prohibit one or more IMDs from producing one or more stimulations. In some embodiments, the IMD may require a code to begin charging and/or to initiate a stimulation or therapy. In another example, after receiving one or more treatment feedback signals, far field transmitter 1304 may modify (e.g., change) which far field radiative signals are transmitted to modify (e.g., change) which IMDs are charged to modify (e.g., change) the treatment protocol. In this example, the control device may also prohibit one or more IMDs from producing one or more stimulations.

In another example, a patient may receive two or more (e.g., 2 to N) treatment protocols. After experiencing these treatment protocols, the patient may determine that a second treatment protocol is better than any other treatment protocol. Based on this input for the patient, the second treatment protocol may be implemented as the sole treatment protocol, the primary treatment protocol, and/or any other designation.

In another example, a patient may receive two or more (e.g., 2 to N) treatment protocols. After obtaining data relating to these treatment protocols, a medical personnel may determine that a third treatment protocol is better than any other treatment protocol. Based on this input for the patient, the third treatment protocol may be implemented as the sole treatment protocol, the primary treatment protocol, and/or any other designation.

In another example, far field transmitter 1304 may transmit one or more far field radiative signals to charge one or more IMDs based on a first treatment protocol. After receiving one or more body parameter signals, far field transmitter 1304 may modify (e.g., change) which far field radiative signals are transmitted to modify (e.g., change) which IMDs are charged to modify (e.g., change) the treatment protocol. In another example, after receiving one or more treatment feedback signals, far field transmitter 1304 may not modify which far field radiative signals are transmitted. However, a control device may prohibit one or more IMDs from producing one or more stimulations. In some embodiments, the IMD may require a code to begin charging and/or to initiate a stimulation or therapy. In another example, after receiving one or more treatment feedback signals, far field transmitter 1304 may modify (e.g., change) which far field radiative signals are transmitted to modify (e.g., change) which IMDs are charged to modify (e.g., change) the treatment protocol. In this example, the control device may also prohibit one or more IMDs from producing one or more stimulations. For example, the one or more body parameter signals may indicate that the patient is sleeping, exercising, lying down, sitting, and/or any other human function.

Figure 20:
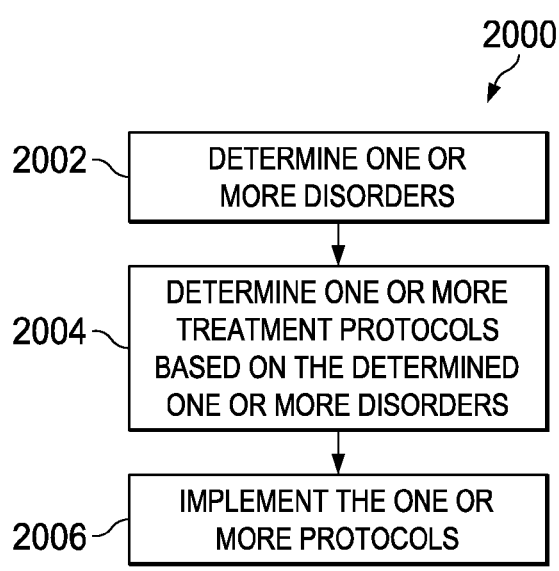
FIG. 20 is another flow diagram of a treatment protocol, according to one embodiment.

In FIG. 20, a second flow diagram 2000 is shown, according to one embodiment. The method may include determining one or more patient disorders, at 2002. The method may include determining one or more treatment protocols based on the determined one or more disorders, at 2004. The method may include implementing the one or more treatment protocols, at 2006.

For example, two or more (e.g., 2 to N) difference treatment procedures may be utilized based on a patient having two or more different disorders. For example, a first treatment procedure for a seizure disorder may be utilized and a second treatment procedure for a depression disorder may be utilized. In another example, a first treatment procedure for a seizure disorder may be utilized when a warning signal that an imminent seizure event may occur, when an actual seizure event is occurring, and/or when an actual seizure event has occurred and a second treatment procedure for a seizure disorder may be utilized when none of the above-events are determined. In addition, a third treatment procedure may be utilized for a depression disorder. Further, a fourth treatment procedure may be utilized for an overeating disorder.

In another example, two or more different (e.g., 2 to N) treatment procedures for one disorder may be utilized based on one or more criteria. For example, a first treatment procedure for a seizure disorder may be utilized when a warning signal that an imminent seizure event may occur, when an actual seizure event is occurring, and/or when an actual seizure event has occurred and a second treatment procedure for a seizure disorder may be utilized when none of the above-events are determined.

Figure 21:
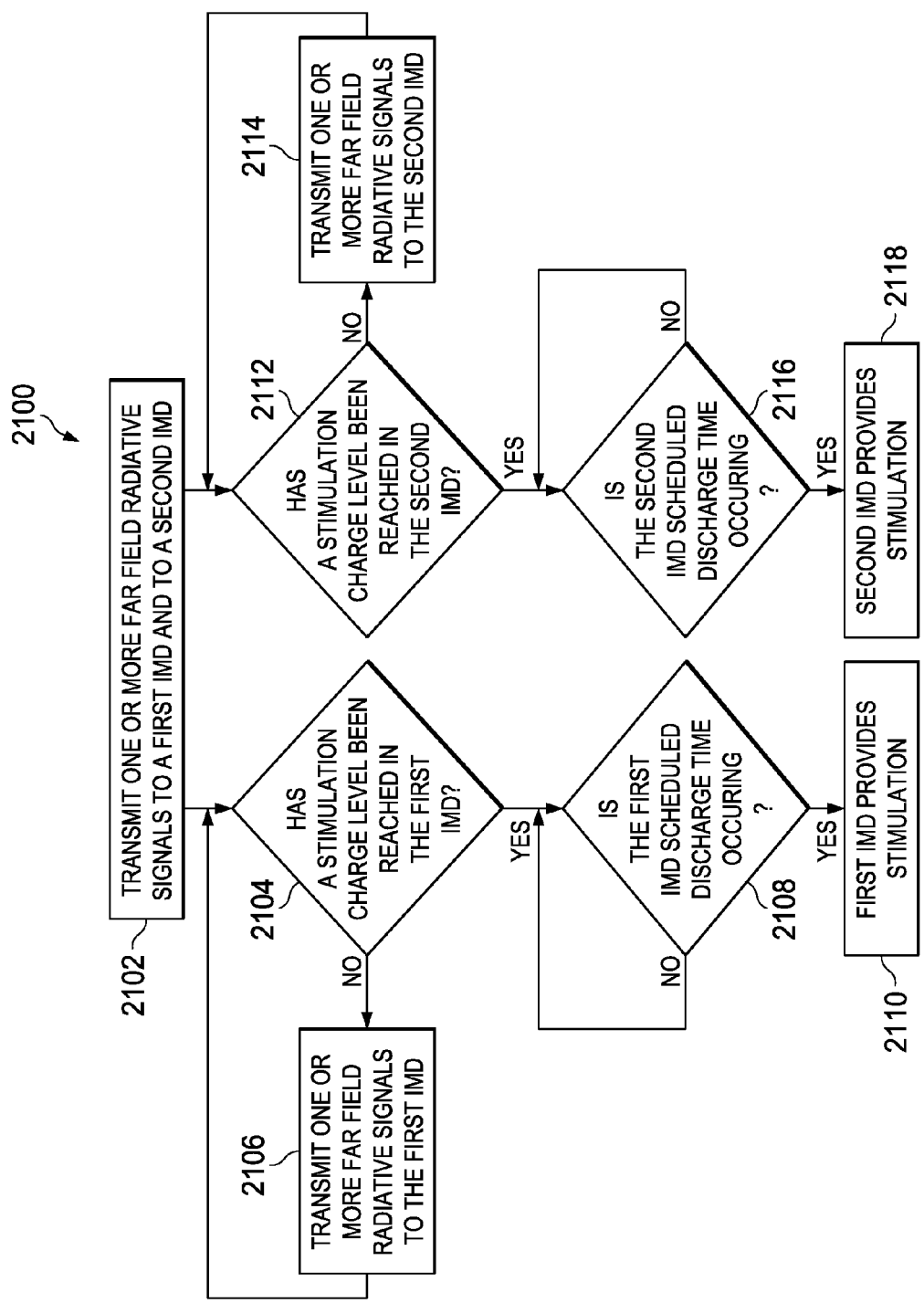
FIG. 21 is a flow diagram of a charging procedure, according to one embodiment.

In FIG. 21, a first flow diagram of a charging procedure 2100 is shown, according to one embodiment. The method may include transmitting one or more far field radiative signals to a first IMD at a first location implanted within the patient and to a second IMD at a second location implanted within the patient, at 2102. The method may include determining whether the stimulation charge level has been reached in the first IMD, at 2104. If the stimulation charge level has not been reached in the first IMD, then the method may include transmitting one or more far field radiative signals to the first IMD, at 2106 and then returning to 2104. If the stimulation charge level has been reached in the first IMD, then the method may include determining whether the first IMD's scheduled discharge time is occurring, at 2108. If the first IMD's scheduled discharge time is not occurring, the method loops back to 2108. If the first IMD's scheduled discharge time is occurring, the method may include that the first IMD provides one or more stimulations, at 2110. In some embodiments, the 2108 may be optional and the first IMD provides stimulation at 2110 once the stimulation charge level has been reached in the first IMD, at 2104. The method may also include determining whether the charge level has been reached in the second IMD, at 2112. If the stimulation charge level has not been reached in the second IMD, then the method may include transmitting one or more far field radiative signals to the second IMD, at 2114 and then returning to 2112. The method may include determining whether the second IMD's scheduled discharge time is occurring, at 2116. If the second IMD's scheduled discharge time is not occurring, then the method may loop back to 2116. If the second IMD's scheduled discharge time is occurring, the method may include that the second IMD provides one or more stimulations, at 2118. In some embodiments, the 2116 may be optional and the second IMD provides stimulation at 2118 once the stimulation charge level has been reached in the second IMD, at 2112.

Figure 22:
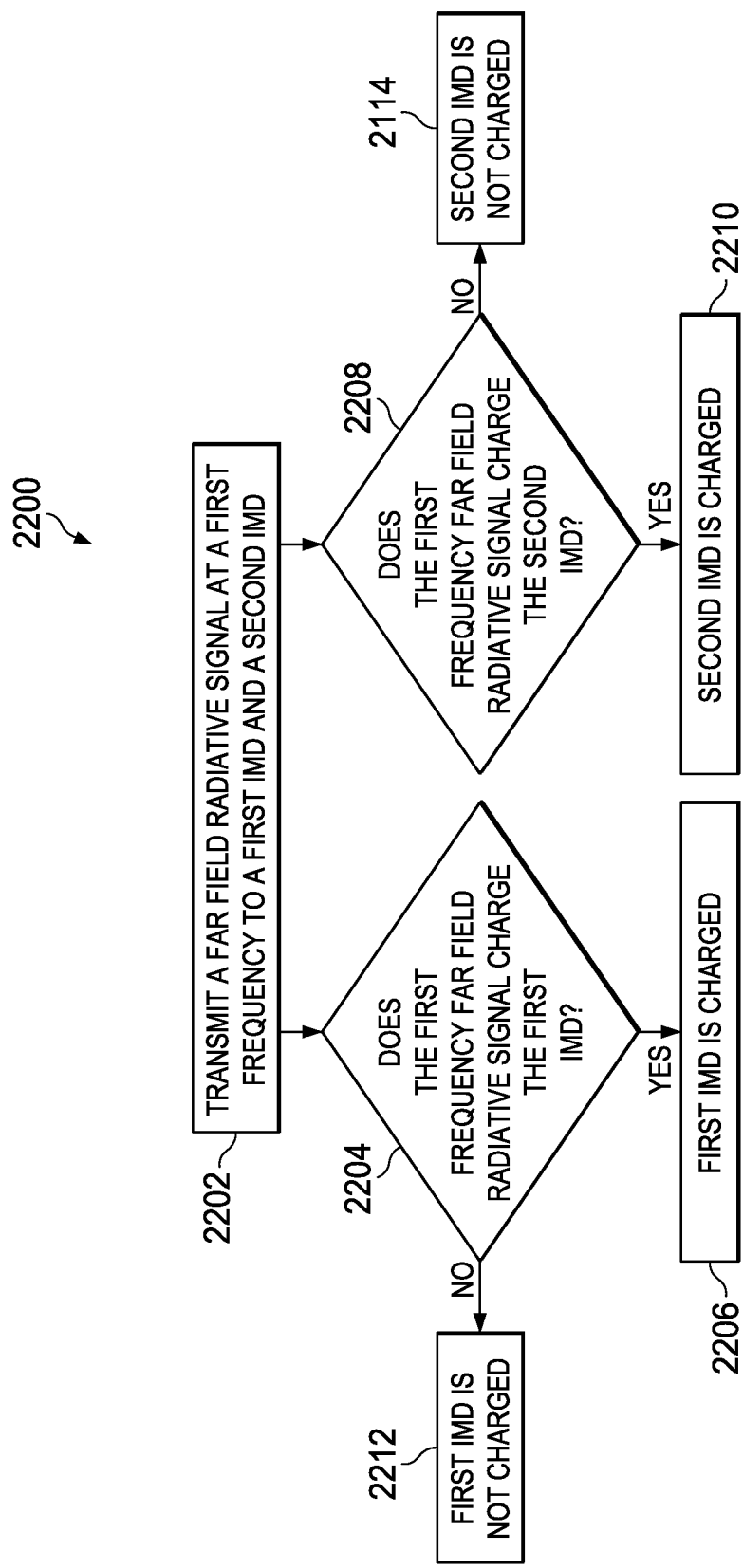
FIG. 22 is another flow diagram of a charging procedure, according to one embodiment.

In FIG. 22, a second flow diagram of a charging procedure 2200 is shown, according to one embodiment. The method may include transmitting a far field radiative signal at a first frequency to a first IMD and a second IMD, at 2202. The method may include determining whether the first frequency charges the first IMD, at 2204. If the first frequency does not charge the first IMD, then the first IMD is not charged, at 2212. If the first frequency charges the first IMD, then the method charges the first IMD, at 2206. The method may include determining whether the first frequency far field radiative signal charges the second IMD, at 2208. If the first frequency does not charge the second IMD, then the second IMD is not charged, at 2214. If the first frequency charges the second IMD, then the method charges the second IMD, at 2210.

Figure 23:
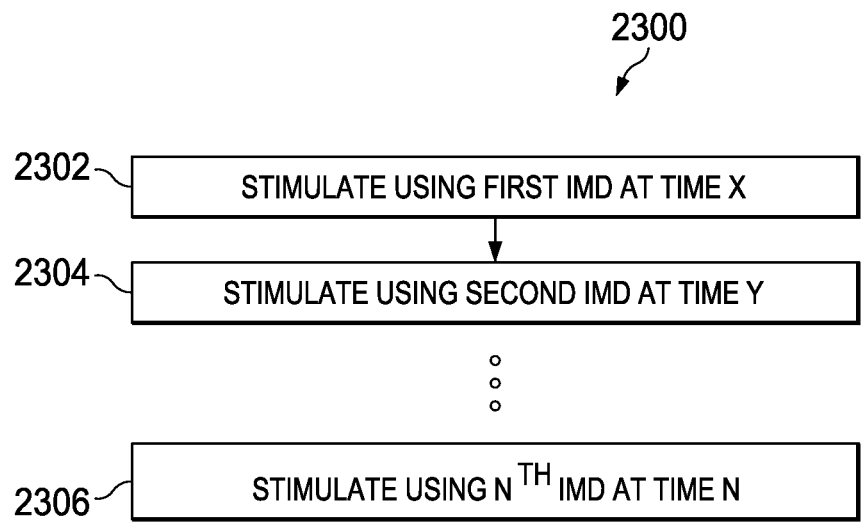
FIG. 23 is a flow diagram of a treatment protocol, according to one embodiment.

In FIG. 23, a third flow diagram of a treatment protocol 2300 is shown, according to one embodiment. The method may include stimulating from the first IMD at time=X, at 2302. The method may include stimulating from the second IMD at time=Y, at 2304. The method may include stimulating from the Nth IMD at time=N, at 2306.

One or more treatment protocols may be based on one or more disorders. The one or more disorders may include epilepsy, depression, seizures, autism, attention deficit/hyperactivity disorder, bulimia, compulsive overeating, obesity, anorexia nervosa, traumatic brain injury, stroke, coma, migraine, neuropathic pain, ischemia, congestive heart failure, angina, sleep disorders, a dementia disorder, any other disorder, and/or any combination thereof.

For example, a first treatment protocol based on a patient having a seizure disorder may include charging first IMD 1310, third IMD 1314, and fourth IMD 1416 to provide one or more stimulations on a predetermined basis (e.g., 1 microsecond, 30 microseconds, 1 second, 5 seconds, 10 seconds, 15 seconds, 30 seconds, 1 minute, 5 minutes, 20 minutes, one hour, two hours, or any other time period) or responsive to feedback. The far field radiative signals used to charge the first IMD 1310, the third IMD 1314, and the fourth IMD 1316, respectively, may each have a different frequency, or one or more of the far field radiative signals may have a different frequency. In another example, the first treatment protocol may include initiating charging of the first IMD 1310 to provide a first stimulation at time T (e.g., reference point=0), initiating charging of the third IMD 1314 to provide a second stimulation at time T+X (e.g., where X may be 0 seconds, 10 seconds, 20 seconds, 1 minute, 5 minutes, 1 hour, or any other time period), and initiating charging of the fourth IMD 1316 to provide a third stimulation at time T+Y (e.g., where Y may be 0 seconds, 10 seconds, 20 seconds, 1 minute, 5 minutes, 1 hour, or any other time period).

The charge initiation and stimulation sequence may follow a predetermined order. For example, charging may be initiated at the first IMD 1310 followed by the third IMD 1314 and then the fourth IMD 1316. The stimulation sequence may follow the charge initiation sequence. In some embodiments, the stimulation sequence may be different from the charge initiation sequence. In some embodiments the charge initiation sequence for the multiple devices may be synchronized or not synchronized. For example, the charge initiation sequence may be simultaneous, staggered (e.g., a portion of the charging charge of one device may overlap or not overlap with another device), interleaved, random (e.g., random within a range), pseudorandom, predetermined (e.g., repeat the same predetermined sequence and/or different predetermined sequences), responsive to feedback from one or more sources (e.g., user, external device, one or more body parameters (e.g., sensed body parameters, such as heart rate, ECG, EEG, EMG, respiration, motion, temperature, blood oxygen level, or any other sensed or derived body parameter), time of day, determined patient activity and/or location), responsive to a received initiation code, or a combination thereof. In some embodiments, the charge initiation of the one or more implantable medical devices may operate independently from one another. In some embodiments, a first time interval between subsequent charge initiations of a first IMD may be different from a second time interval of subsequent charge initiations of a second IMD. For example, the first time interval may be a percentage of the second time interval (e.g., first time interval may be 40% of the second time interval), the first time interval and the second time interval may be a ratio (e.g., the first time interval may be equivalent to ten of the second time intervals) or may be a multiple of the other (e.g., the first time interval may be five times longer than the second time interval), or any other coordinated pattern or sequence. In some embodiments, the stimulation sequence for multiple devices may be synchronized or not synchronized. For example, the stimulation sequence for multiple devices may be simultaneous (e.g., two or more IMDs stimulate at approximately the same time), staggered (e.g., a portion of the stimulation deliver of one device may overlap or not overlap with another device), interleaved, random (e.g., random within a range), pseudorandom, predetermined (e.g., repeat the same predetermined sequence and/or in different predetermined sequences), responsive to feedback from one or more sources (e.g., user, external device, one or more body parameters (e.g., sensed body parameters, such as heart rate, ECG, EEG, EMG, respiration, motion, temperature, blood oxygen level, or any other sensed or derived body parameter), time of day, determined patient activity and/or location), responsive to a received initiation code, or a combination thereof. In some embodiments, the stimulation provided by the one or more implantable medical devices may operate independently from one another. In some embodiments, a first time interval between subsequent stimulations of a first IMD may be different from a second time interval of subsequent stimulations of a second IMD. For example, the first time interval may be a percentage of the second time interval (e.g., first time interval may be 40% of the second time interval), the first time interval and the second time interval may be a ratio (e.g., the first time interval may be equivalent to ten of the second time intervals) or may be a multiple of the other (e.g., the first time interval may be five times longer than the second time interval), or any other coordinated pattern or sequence. In another example, a first charge initiation and stimulation sequence may occur in the following order: the first IMD 1310, the third IMD 1314, and the fourth IMD 1316. After the first charge initiation and stimulation sequence has been implemented a predetermined number of times (e.g., 1 to N times) and/or based on one or more feedback signals, then a second charge initiation and stimulation sequence may be implemented. After the second charge initiation and stimulation sequence has been implemented a predetermined number of times (e.g., 1 to N times) and/or based on one or more feedback signals, then a third charge initiation and stimulation sequence may be implemented. After an Nth charge initiation and stimulation sequence has been implemented for a predetermined number of times (e.g., 1 to N times) and/or based on one or more feedback signals, then another charge initiation and stimulation sequence (e.g., first charge initiation and stimulation sequence, second charge initiation and stimulation sequence, third charge initiation and stimulation sequence, . . . and/or Nth charge initiation and stimulation sequence) may be implemented. The second charge initiation and stimulation sequence may occur in the following order: the third IMD 1314, the first IMD 1310, and the fourth IMD. The third charge initiation and stimulation sequence may occur in the following order: the fourth IMD 1316, the first IMD 1310, and the third IMD 1314. The one or more implantable medical devices may provide stimulation immediately after being charged (e.g., reaching a charge threshold, based on an initiation signal or code, or at any time thereafter.

In one example, the first treatment sequence may include stimulating with the second IMD 1312 at time 0, then stimulating with the third IMD 1314 one second later, and then stimulating with the fourth IMD 1316 one second later. The second treatment sequence may include stimulating with the second IMD 1312 at time 0, then stimulating with the third IMD 1314 five seconds later, and then stimulating with the fourth IMD 1316 one second later. The third treatment sequence may include stimulating with the second IMD 1312 at time 0, then stimulating with the fourth IMD 1316 one minute later, and then stimulating with the third IMD 1314 one minute later.

Figure 24:
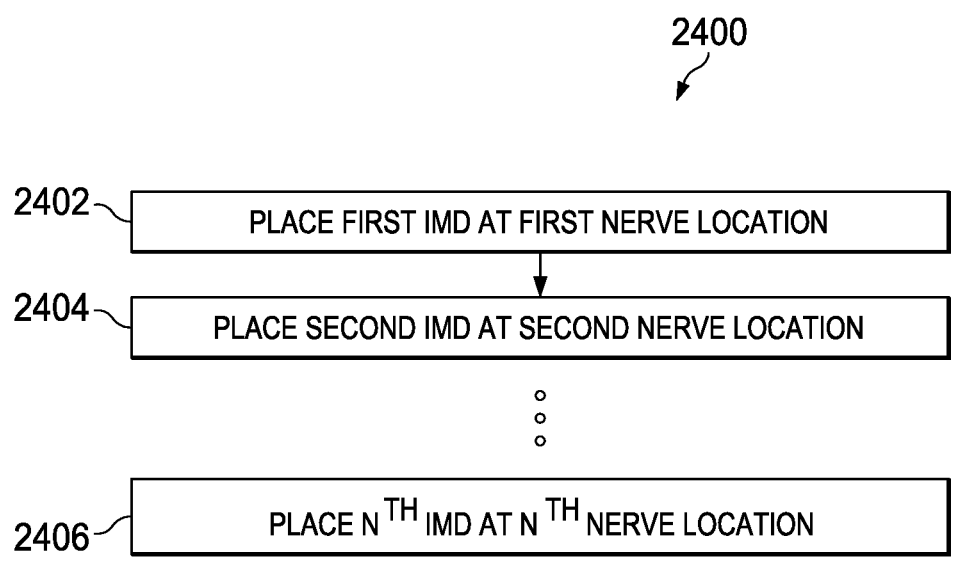
FIG. 24 is a flow diagram from an implanting procedure, according to one embodiment.

In FIG. 24, a flow diagram from an implanting procedure 2400 is shown, according to one embodiment. The method may include placing a first IMD at a first nerve location, at 2402. The method may include placing a second IMD at a second nerve location, at 2404. The method may include placing an Nth IMD at an Nth nerve location, at 2406. In another example, the method may include determining one or more locations to place one or more IMDs. In another example, the method may include determining one or more locations to place one or more IMDs based on one or more patient disorders, patient information (e.g., sex, health, body type, BMI, etc.), historical data, and/or any combination thereof.

In one embodiment, an implantable IMD system may include a first IMD at a first nerve location configured to receive a first far field radiative signal in a first frequency band via a first antenna and to receive a second far field radiative signal in a second frequency band via a second antenna. The first IMD may be configured to store charge from the first far field radiative signal and the second far field radiative signal. The first IMD may be configured to provide a first stimulation from a first IMD stored charge. The implantable IMD system may also include a second IMD at a second nerve location configured to receive a third far field radiative signal in a third frequency band via a third antenna. The second IMD may be configured to store charge from the third far field radiative signal. The second IMD may be configured to provide a second stimulation from a second IMD stored charge.

In one example, the first stimulation and the second stimulation may be provided on a treatment schedule based on a treatment protocol. In another example, the treatment protocol may be based on a disorder of a patient. In an example, the implantable IMD system may include one or more processors configured to obtain one or more treatment feedback signals. In another example, the first stimulation and the second stimulation may be provided on a treatment schedule based on a treatment protocol. In one example, one or more processors may modify the treatment schedule and/or the treatment protocol based on the one or more treatment feedback signals. In an example, the first stimulation and the second stimulation may be provided on two or more treatment schedules based on two or more treatment protocols. In another example, the two or more treatment protocols may be based on two or more disorders of the patient. The two or more disorders may include epilepsy, depression, seizures, autism, attention deficit/hyperactivity disorder, bulimia, compulsive overeating, obesity, anorexia nervosa, traumatic brain injury, stroke, coma, migraine, neuropathic pain, ischemia, congestive heart failure, angina, sleep disorders, and/or dementia disorder. In another example, the first far field radiative signal and the second far field radiative signal may each have a frequency in a frequency band centered at one of approximately 433 MHz and 900 MHz, respectively, approximately 433 MHz and 2.4 GHz, respectively, approximately 433 MHz and 5.8 GHz, respectively, approximately 900 MHz and 2.4 GHz, respectively, approximately 900 MHz and 5.8 GHz, respectively, and approximately 2.4 GHz and 5.8 GHz, respectively. Further, the third far field radiative signal may have a frequency in a frequency band centered at one of approximately 433 MHz, approximately 900 MHz, approximately 2.4 GHz, and approximately 5.8 GHz.

In one embodiment, a method may include charging a first IMD via one or more far field radiative signals at a first frequency band. The method may include charging a second IMD via one or more far field radiative signals at a second frequency band. The method may include providing one or more stimulations from the first IMD. The method may also include providing one or more stimulations from the second IMD.

In one example, the one or more stimulations from the first IMD may be at a first time. In another example, the one or more stimulations from the second IMD may be at the first time plus a delay period. In one example, the method may include charging a third IMD via one or more far field radiative signals at a third frequency band. The method may include delivering a first therapy in a first sequence based on a first therapy protocol. The first sequence may be as follows: one or more stimulations from the first IMD at a first time at a first target tissue; one or more stimulations from the second IMD at a second time at a second target tissue; and/or one or more stimulations from the third IMD at a third time at a third target tissue. In another example, the method may include delivering a second therapy in a second sequence after the first therapy has been implemented. The second therapy may be based on a second therapy protocol. The second sequence may be as follows: one or more stimulations from the third IMD at a fourth time to a third target tissue; one or more stimulations from the first IMD at a fifth time to the first target tissue; and/or one or more stimulations from the second IMD at a sixth time to a second target tissue.

In one embodiment, a method may include charging a first IMD via one or more far field radiative signals at a first frequency band. The method may include charging a second IMD via one or more far field radiative signals at a second frequency band. The method may include charging a third IMD via one or more far field radiative signals at a third frequency band. The method may include providing one or more stimulations from the first IMD to a first target tissue where the one or more stimulations from the first IMD occur at a first time. The method may include providing one or more stimulations from the second IMD to a second target tissue where the one or more stimulations from the second IMD occur at the first time plus a first delay period. The method may also include providing one or more stimulations from the third IMD to a third target tissue where the one or more stimulations from the third IMD occur at the first time plus a second delay period.

In one example, the method may include obtaining a first feedback signal and modifying one or more stimulations from the first IMD, one or more stimulations from the second IMD, and/or one or more stimulations from the third IMD based on the first feedback signal. In another example, the modification may include changing the first time, changing the first time plus the first delay, changing the first time plus the second delay, changing a first IMD stimulation characteristics, changing a second IMD stimulation characteristics, and/or changing a third IMD stimulation characteristics. In an example, the method may include obtaining a second feedback signal and returning to an original stimulation treatment protocol based on the second feedback signal.

Embodiments disclosed herein enable efficiently providing power to an implantable medical device over a relatively long distance. Further, embodiments disclosed herein enable the implantable medical device to be relatively small since a charge storage element of the implantable medical device only needs to be large enough to store enough energy for a single treatment or relatively small number of treatments. Such embodiments may provide effective screening tools to determine whether a particular type of treatment will be effective for a particular patient. For example, vagus nerve stimulation is believed to be effective on about half of a particular candidate patient population. Currently methods of providing vagus nerve stimulation typically involve implanting a medical device in a patient's chest area and running leads under the patient's skin to electrodes implanted in the patient's neck. Since implantable medical devices described herein can be relatively small and may be directly coupled to electrodes, less invasive surgical procedures can be used to implant the implantable medical devices. Thus, these implantable medical devices may be used as screening tools to determine whether vagus nerve stimulation will be effective on a particular patient.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A system comprising:
   a first implantable medical device configured to receive a first far field radiative signal at a first frequency from an external transmitter and to charge a first charge storage device using the first far field radiative signal, the first implantable medical device comprising:
      a first therapy delivery unit powered by the first charge storage device and configured to deliver a first therapy to a first target tissue of a patient, wherein the first therapy includes delivery of a first electrical stimulation signal to the first target tissue; and
      control circuitry configured to encode data by modulating energy backscattered responsive to the first far field radiative signal; and a second implantable medical device configured to receive a second far field radiative signal at a second frequency different from the first frequency from the external transmitter and to charge a second charge storage device using the second far field radiative signal, the second implantable medical device comprising a second therapy delivery unit powered by the second charge storage device and configured to deliver a second therapy to a second target tissue of the patient, wherein the second therapy includes delivery of a second electrical stimulation signal to the second target tissue.

2. The system of claim 1, wherein the first target tissue is a first nerve area of a cranial nerve and the second target tissue is a second nerve area of the cranial nerve.

3. The system of claim 1, wherein the first therapy delivery unit is further configured to modify the first electrical stimulation signal based on a feedback signal and to deliver the modified first electrical stimulation signal to the first target tissue of the patient.

4. The system of claim 1, further comprising a threshold detector coupled to the first charge storage device, wherein the threshold detector is configured to initiate delivery of the first electrical stimulation signal responsive to detecting that the charge stored at the first charge storage device satisfies a stimulation threshold.

5. The system of claim 1, wherein the first implantable medical device is configured to receive a stimulation initiation code via the first far field radiative signal and to enable the first therapy delivery unit to deliver the first electrical stimulation signal to the first target tissue of the patient responsive to the stimulation initiation code.

6. The system of claim 1, wherein delivery of the first electrical stimulation signal and delivery of the second electrical stimulation signal is one of a synchronized delivery, substantially simultaneous delivery, staggered delivery, or interleaved delivery.

7. The system of claim 1, wherein the first implantable medical device is configured to receive a charge initiation code via the first far field radiative signal and to enable charging of the first charge storage device responsive to the charge initiation code.

8. The system of claim 1, wherein the first far field radiative signal and the second far field radiative signal each have a frequency in a frequency band centered at one of approximately 433 MHz and 900 MHz, respectively, approximately 433 MHz and 2.4 GHz, respectively, approximately 433 MHz and 5.8 GHz, respectively, approximately 900 MHz and 2.4 GHz, respectively, approximately 900 MHz and 5.8 GHz, respectively, or approximately 2.4 GHz and 5.8 GHz, respectively.

9. The system of claim 1, wherein the first implantable medical device further comprising an antenna configured to receive the first far field radiative signal.

10. The system of claim 9, wherein the first implantable medical device further comprising a voltage rectifier configured to rectify the first far field radiative signal received by the antenna to provide a rectified voltage signal.

11. The system of claim 10, wherein the voltage rectifier comprises at least one Schottky diode.

12. The system of claim 10, wherein the voltage rectifier is a multi-stage rectifier.

13. The system of claim 10, wherein the first implantable medical device further comprising a flexible printed circuit board, wherein the voltage rectifier, the first charge storage device, and the first therapy delivery unit are integrated on the flexible printed circuit board.

14. The system of claim 10, wherein the first implantable medical device further comprising a DC-to-DC converter coupled to the voltage rectifier, wherein the DC-to-DC converter is configured to receive output of a voltage multiplier of the voltage rectifier.

15. The system of claim 1, wherein the encoded data is in a third order frequency harmonic component of the energy backscattered by the first implantable medical device using a nonlinear component, and wherein the nonlinear component is at least one of a high-Q frequency resonant circuit, a high-frequency amplifier, a diode or a far field transmitter.

16. A system comprising:
an external transmitter configured to transmit a first far field radiative signal at a first frequency and a second far field radiative signal at a second frequency different from the first frequency;
a first implantable medical device configured to receive the first far field radiative signal from an external transmitter and to charge a first charge storage device using the first far field radiative signal, the first implantable medical device comprising:
a first therapy delivery unit powered by the first charge storage device and configured to deliver a first therapy to a first target tissue of a patient, wherein the first therapy includes delivery of a first electrical stimulation signal to the first target tissue; and
control circuitry configured to encode data by modulating energy backscattered responsive to the first far field radiative signal; and
a second implantable medical device configured to receive a second far field radiative signal from the external transmitter and to charge a second charge storage device using the second far field radiative signal, the second implantable medical device comprising a second therapy delivery unit powered by the second charge storage device and configured to deliver a second therapy to a second target tissue of the patient, wherein the second therapy includes delivery of a second electrical stimulation signal to the second target tissue.

17. The system of claim 16, the external transmitter further comprising a first transmitter configured to transmit the first far field radiative signal and a second transmitter configured to transmit the second far field radiative signal.

18. The system of claim 16, wherein the external transmitter is configured to transmit the first far field radiative signal according to a first treatment protocol and to transmit the second far field radiative signal according to a second treatment protocol different from the first treatment protocol.

19. The system of claim 16, wherein at least one of the first far field radiative signal or the second far field radiative signal is a pulsed signal.

20. An external device comprising:
a first external transmitter configured to transmit a first far field radiative charging signal at a first frequency to a first implantable medical device according to a treatment protocol, the first far field radiative charging signal configured to charge the first implantable medical device to enable the first implantable medical device to deliver a first therapy to a first target tissue of a patient;
an external receiver to receive encoded data from the first implantable medical device, wherein the encoded data is encoded in energy backscattered by the first implantable medical device responsive to the first far field radiative charging signal; and a second external transmitter configured to transmit a second far field radiative charging signal at a second frequency different from the first frequency to a second implantable medical device according to the treatment protocol to enable the second far field radiative charging signal to charge the second implantable medical device, the second implantable medical device configured to deliver a second therapy to a second target tissue of the patient.

21. The external device of claim 20, wherein the first external transmitter is configured to generate the first far field radiative charging signal as a pulsed signal.

22. The external device of claim 20, wherein the first implantable medical device is further configured to determine when to transmit the first far field radiative charging signal according to the treatment protocol; and wherein the second implantable medical device is further configured to determine when to transmit the second far field radiative charging signal according to the treatment protocol.

23. The external device of claim 20, wherein transmission of the first far field radiative charging signal and transmission of the second far field radiative charging signal is one of a not synchronized transmission, random transmission, pseudorandom transmission, or transmitted at different time intervals.

* * * * *